US011833200B2

(12) United States Patent
Vezina et al.

(10) Patent No.: US 11,833,200 B2
(45) Date of Patent: *Dec. 5, 2023

(54) METHOD OF PREPARING PLANT-DERIVED PROTEINS

(75) Inventors: Louis-Philippe Vezina, Neuville (CA); Manon Couture, St. Augustin De Desmaures (CA); Dany Paquet, St. Jean Chrysostome (CA); Michele Dargis, Quebec (CA); Marc-Andre D'Aoust, Quebec (CA)

(73) Assignee: MEDICAGO INC., Quebec (CA)

( * ) Notice: Subject to any disclaimer, the term of this patent is extended or adjusted under 35 U.S.C. 154(b) by 0 days.

This patent is subject to a terminal disclaimer.

(21) Appl. No.: 13/497,767

(22) PCT Filed: Sep. 21, 2010

(86) PCT No.: PCT/CA2010/001489
§ 371 (c)(1),
(2), (4) Date: Mar. 22, 2012

(87) PCT Pub. No.: WO2011/035423
PCT Pub. Date: Mar. 31, 2011

(65) Prior Publication Data
US 2013/0067807 A1    Mar. 21, 2013

Related U.S. Application Data

(60) Provisional application No. 61/244,786, filed on Sep. 22, 2009.

(51) Int. Cl.
| C12N 7/00 | (2006.01) |
| C12N 15/82 | (2006.01) |
| A61K 39/145 | (2006.01) |
| A61K 39/12 | (2006.01) |
| A61K 39/00 | (2006.01) |

(52) U.S. Cl.
CPC ........... A61K 39/145 (2013.01); A61K 39/12 (2013.01); C12N 7/00 (2013.01); C12N 15/8203 (2013.01); C12N 15/8257 (2013.01); C12N 15/8258 (2013.01); A61K 2039/517 (2013.01); A61K 2039/5258 (2013.01); C12N 2760/16123 (2013.01); C12N 2760/16134 (2013.01)

(58) Field of Classification Search
None
See application file for complete search history.

(56) References Cited

U.S. PATENT DOCUMENTS

| 4,945,050 A | 7/1990 | Sanford |
| 5,036,006 A | 7/1991 | Sanford |
| 5,100,792 A | 3/1992 | Sanford |
| 5,166,068 A * | 11/1992 | Fujimura ............... A01H 4/00 435/421 |
| 5,232,833 A | 8/1993 | Sanders |
| 5,486,510 A | 1/1996 | Bouic |
| 5,625,136 A | 4/1997 | Koziel |
| 5,762,939 A | 6/1998 | Smith |
| 5,773,695 A * | 6/1998 | Thompson ........... C07K 14/415 435/320.1 |
| 5,858,368 A | 1/1999 | Smith |
| 5,958,422 A | 9/1999 | Lomonossoff |
| 6,020,169 A * | 2/2000 | Lee et al. .................... 435/70.1 |
| 6,042,832 A | 3/2000 | Koprowski et al. |
| 6,284,875 B1 * | 9/2001 | Turpen .................. C07K 14/57 530/334 |
| 6,326,470 B1 * | 12/2001 | Cosgrove ..................... 530/370 |
| 6,403,865 B1 | 6/2002 | Koziel |
| 6,489,537 B1 | 12/2002 | Rea |
| 7,125,978 B1 | 10/2006 | Vezina |
| 7,132,291 B2 | 11/2006 | Cardineau |
| 7,897,842 B2 | 3/2011 | Baker |
| 8,124,103 B2 | 2/2012 | Yusibov et al. |
| 9,452,210 B2 | 9/2016 | D'Aoust et al. |

(Continued)

FOREIGN PATENT DOCUMENTS

| AU | 2008278222 A1 | 1/2009 |
| AU | 2009202819 | 6/2009 |

(Continued)

OTHER PUBLICATIONS

Davey et al (Biotechnology Advances, 23, pp. 131-171, 2005); cited on IDS.*
Yigzaw et al (Biotechnol Prog, 22(1), pp. 286-296, 2006).*
Fischer et al (Journal of Immunological Methods, 226(1-2), pp. 1-10, 1999).*
Takahashi et al (The Plant Journal, 49, pp. 1030-1040, 2007).*
Power et al (Biochem J., 111(5), 33P, 1969).*
Waterhouse et al (Journal of Virological Methods, 1984, 8: 321-329).*
Siminis et al (Plant Physiol., 1994, 105:1375-1383).*
Martin et al (Journal of Bacteriology, 1981, 145(2): 980-983).*
Prakash et al (J. Biosci. 1997, 3:339-344).*
Schmidt et al (Plant Physiol., 1980, 66: 25-28).*

(Continued)

Primary Examiner — Charles Logsdon
(74) Attorney, Agent, or Firm — BALLARD SPAHR LLP

(57) ABSTRACT

Methods of preparing plant-derived proteins or suprastructure proteins, are provided. The method may comprise obtaining a plant, or plant matter comprising apoplast-localized proteins, or suprastructure proteins, producing a protoplast/spheroplast fraction and apoplast fraction from the plant or plant matter, and recovering the apoplast fraction. The apoplast fraction comprises plant-derived proteins or suprastructure proteins. Alternatively, the proteins, or suprastructure proteins, may be obtained from plant or plant matter comprising plant-derived proteins or suprastructure proteins, by digesting the plant matter using a cell wall degrading enzyme composition to produced a digested fraction. The digested fraction is filtered to produced a filtered fraction, and the plant-derived proteins or suprastructure proteins, are recovered from the filtered fraction.

11 Claims, 17 Drawing Sheets

Specification includes a Sequence Listing.

(56) References Cited

U.S. PATENT DOCUMENTS

| | | | |
|---|---|---|---|
| 9,459,470 B2 | 10/2016 | Hillis et al. | |
| 9,492,528 B2 | 11/2016 | D'Aoust et al. | |
| 9,815,873 B2* | 11/2017 | Couture | C07K 14/415 |
| 2001/0006950 A1 | 7/2001 | Punnonen | |
| 2004/0002061 A1 | 1/2004 | Kawaoka | |
| 2004/0268442 A1 | 12/2004 | Miller et al. | |
| 2005/0048074 A1 | 3/2005 | Cardineau | |
| 2006/0252132 A1 | 11/2006 | Yang | |
| 2006/0263804 A1 | 11/2006 | Robinson et al. | |
| 2007/0207526 A1 | 9/2007 | Coit et al. | |
| 2007/0286873 A1 | 12/2007 | Williams | |
| 2009/0117144 A1 | 5/2009 | Rasochova | |
| 2009/0191309 A1 | 7/2009 | Rastogi et al. | |
| 2009/0311669 A1 | 12/2009 | Kawaoka | |
| 2010/0167376 A1* | 7/2010 | Hogan | C12P 19/14 |
| | | | 435/209 |
| 2010/0239610 A1 | 9/2010 | D'Aoust | |
| 2010/0310604 A1 | 12/2010 | D'Aoust | |
| 2011/0191915 A1 | 8/2011 | Couture | |
| 2011/0293650 A1 | 12/2011 | D'Aoust | |
| 2012/0178149 A1 | 7/2012 | Vezina | |
| 2012/0189658 A1 | 7/2012 | Couture | |
| 2013/0067807 A1 | 3/2013 | Vezina | |
| 2013/0142826 A1 | 6/2013 | D'Aoust | |
| 2013/0183341 A1 | 7/2013 | D'Aoust | |
| 2013/0295609 A1 | 11/2013 | D'Aoust et al. | |

FOREIGN PATENT DOCUMENTS

| | | |
|---|---|---|
| AU | 2009202819 A1 | 6/2009 |
| AU | 2008278222 | 1/2010 |
| AU | 2009267759 | 1/2010 |
| AU | 2009267759 A1 | 1/2010 |
| AU | 2010265766 | 6/2010 |
| AU | 2010265766 | 2/2012 |
| AU | 2010300033 | 3/2012 |
| AU | 2010300033 A1 | 3/2012 |
| AU | 2010300034 | 3/2012 |
| AU | 2010300034 A1 | 3/2012 |
| AU | 2012231717 | 9/2013 |
| CA | 2615372 A1 | 1/2009 |
| CA | 2693956 | 1/2009 |
| CA | 2693956 A1 | 1/2009 |
| CA | 2707235 | 6/2009 |
| CA | 2707235 A1 | 6/2009 |
| CA | 2615372 | 1/2010 |
| CA | 2730185 | 1/2010 |
| CA | 2730185 A1 | 1/2010 |
| CA | 2772962 | 1/2010 |
| CA | 2762042 | 6/2010 |
| CA | 2772962 A1 | 3/2011 |
| CA | 2772964 | 3/2011 |
| CA | 2772964 A1 | 3/2011 |
| CN | 200880107072.9 | 6/2009 |
| CN | 200980109781.5 | 6/2009 |
| CN | 200980134868.8 | 1/2010 |
| CN | 201080042333.0 | 3/2011 |
| CU | 2010006 | 1/2009 |
| CU | D2010006 | 1/2009 |
| CU | 2010152 | 6/2009 |
| CU | D2010152 | 6/2009 |
| EA | 201001198 | 1/2010 |
| EG | 2010010061 | 1/2009 |
| EG | 1222/2010 | 6/2009 |
| EP | 2009793741 | 1/2009 |
| EP | 20080783201 | 1/2009 |
| EP | 2009700061 | 6/2009 |
| EP | 2173886 | 4/2010 |
| EP | 2010791119 | 6/2010 |
| EP | 2238253 | 10/2010 |
| EP | 2010818190 | 3/2011 |
| EP | 2010818191 | 3/2011 |
| EP | 2307549 | 4/2011 |
| EP | 2010791119 | 5/2012 |
| EP | 2480560 | 8/2012 |
| EP | 2480658 | 8/2012 |
| EP | 2570484 | 3/2013 |
| GE | 11920 | 6/2009 |
| ID | W-002010248 | 6/2009 |
| IL | 203018 | 1/2009 |
| IL | 210215 | 1/2009 |
| IL | 206967 | 6/2009 |
| IL | 210215 | 1/2010 |
| IL | 218393 | 3/2011 |
| IL | 218422 | 3/2011 |
| IL | 218393 | 4/2012 |
| IL | 218422 | 4/2012 |
| JP | 2010-516334 | 1/2009 |
| JP | 2011-516934 | 1/2009 |
| JP | 2010-542486 | 6/2009 |
| JP | 2010-516334 A | 5/2010 |
| JP | 2012516452 | 6/2010 |
| JP | 2012-530059 | 3/2011 |
| JP | 2012-530060 | 3/2011 |
| JP | 2011-516934 A | 5/2011 |
| JP | 2012-530059 A | 11/2012 |
| JP | 2012-530060 A | 11/2012 |
| KR | 1020107002538 | 1/2009 |
| KR | 1020117001798 | 1/2009 |
| KR | 1020107018343 | 6/2009 |
| KR | 1020117001798 | 1/2010 |
| KR | 1020107002538 | 3/2010 |
| KR | 1020107018343 | 11/2010 |
| MA | 2010000142 | 1/2009 |
| MA | 2010003442 | 6/2009 |
| MX | MX/a/2010/000525 | 1/2009 |
| MX | MX/a/2010/007962 | 6/2009 |
| MX | MX/a/2011/000459 | 1/2010 |
| MY | PI 2010000142 | 1/2009 |
| MY | PI 2010003442 | 6/2009 |
| NZ | 582360 | 1/2009 |
| NZ | 590144 | 1/2009 |
| NZ | 587108 | 6/2009 |
| NZ | 598481 | 3/2011 |
| NZ | 598508 | 3/2011 |
| NZ | 582360 A | 4/2012 |
| NZ | 590144 A | 11/2012 |
| NZ | 587108 A | 4/2013 |
| PH | 12012500565 | 3/2011 |
| PH | 12012500566 | 3/2011 |
| RU | 2011-105073 | 1/2010 |
| RU | 2012101946 | 6/2010 |
| RU | 2012-115661 | 3/2011 |
| RU | 2012-115996 | 3/2011 |
| RU | 2012-115996 | 10/2013 |
| SG | 201000090-9 | 1/2009 |
| SG | 201009568-5 | 1/2009 |
| SG | 158301 | 4/2012 |
| TH | 1201001223 | 3/2011 |
| TH | 1201001239 | 3/2011 |
| WO | WO 1986/003224 | 6/1986 |
| WO | WO-1986/003224 A1 | 6/1986 |
| WO | WO 2000/009725 | 2/2000 |
| WO | WO-2000/009725 A2 | 2/2000 |
| WO | WO 2000/037663 | 6/2000 |
| WO | WO-2000/037663 A2 | 6/2000 |
| WO | WO 2000/056906 | 9/2000 |
| WO | WO-2000/056906 A1 | 9/2000 |
| WO | WO 2000/063400 | 10/2000 |
| WO | WO-2000/063400 A2 | 10/2000 |
| WO | WO 2002/074795 | 9/2002 |
| WO | WO-2002/074795 A2 | 9/2002 |
| WO | WO 2003/025124 | 3/2003 |
| WO | WO-2003/025124 A2 | 3/2003 |
| WO | WO 2003/068163 | 8/2003 |
| WO | WO-2003/068163 A2 | 8/2003 |
| WO | WO 2003/068993 | 8/2003 |
| WO | WO-2003/068993 A1 | 8/2003 |
| WO | WO 2004/098530 | 11/2004 |
| WO | WO-2004/098530 A2 | 11/2004 |
| WO | WO 2004/098533 | 11/2004 |
| WO | WO-2004/098533 A2 | 11/2004 |
| WO | WO 2005/020889 | 3/2005 |

(56) References Cited

FOREIGN PATENT DOCUMENTS

| | | |
|---|---|---|
| WO | WO-2005/020889 A2 | 3/2005 |
| WO | WO 2006/016380 | 2/2006 |
| WO | WO-2006/016380 A2 | 2/2006 |
| WO | WO 2006/119516 | 11/2006 |
| WO | WO-2006/119516 A2 | 11/2006 |
| WO | WO 2007/011904 | 1/2007 |
| WO | WO-2007/011904 A2 | 1/2007 |
| WO | WO 2007/019094 | 2/2007 |
| WO | WO-2007/019094 A2 | 2/2007 |
| WO | WO 2007/047831 | 4/2007 |
| WO | WO-2007/047831 A2 | 4/2007 |
| WO | WO 2007/095318 | 8/2007 |
| WO | WO-2007/095318 A2 | 8/2007 |
| WO | WO 2007/130327 | 11/2007 |
| WO | WO-2007/130327 A2 | 11/2007 |
| WO | WO 2007/135480 | 11/2007 |
| WO | WO-2007/135480 A1 | 11/2007 |
| WO | WO 2008/054540 | 5/2008 |
| WO | WO-2008/054540 A2 | 5/2008 |
| WO | WO 2008/060669 | 5/2008 |
| WO | WO-2008/060669 A2 | 5/2008 |
| WO | WO 2008/087391 | 7/2008 |
| WO | WO-2008/087391 A1 | 7/2008 |
| WO | WO 2008/151440 | 12/2008 |
| WO | WO-2008/151440 A1 | 12/2008 |
| WO | WO 2009/008573 | 1/2009 |
| WO | WO-2009/008573 A1 | 1/2009 |
| WO | WO 2009/009876 | 1/2009 |
| WO | WO-2009/009876 A1 | 1/2009 |
| WO | WO 2009/026397 | 2/2009 |
| WO | WO-2009/026397 A2 | 2/2009 |
| WO | WO 2009/076778 | 6/2009 |
| WO | WO-2009/076778 A1 | 6/2009 |
| WO | WO 2010/003225 | 1/2010 |
| WO | WO-2010/003225 A1 | 1/2010 |
| WO | WO 2010/003235 | 1/2010 |
| WO | WO 2010/006452 | 1/2010 |
| WO | WO-2010/006452 A1 | 1/2010 |
| WO | WO 2010/025285 | 3/2010 |
| WO | WO-2010/025285 A1 | 3/2010 |
| WO | WO 2010/077712 | 7/2010 |
| WO | WO-2010/077712 A1 | 7/2010 |
| WO | WO 2010/148511 | 12/2010 |
| WO | WO-2010/148511 A1 | 12/2010 |
| WO | WO 2011/035422 | 3/2011 |
| WO | WO-2011/035422 A1 | 3/2011 |
| WO | WO 2011/035423 | 3/2011 |
| WO | WO-2011/035423 A1 | 3/2011 |
| WO | PCT/CA2012/050180 | 3/2012 |
| WO | WO 2012/061815 | 5/2012 |
| WO | WO-2012/061815 A2 | 5/2012 |
| WO | WO 2012/083445 | 6/2012 |
| WO | WO-2012/083445 A1 | 6/2012 |
| WO | WO 2012/126123 | 9/2012 |

OTHER PUBLICATIONS

Twyman et al (Trends in Biotechnology, 2003, 21(12): 570-578).*
Facchini et al (Plant Physiology, 1999, 120: 653-663).*
Hassan et al (PBJ, 2007, 6: 733-748).*
Chargelegue et al (American Society for Microbiology Infection and Immunity, 2005, 73(9): 5915-5922).*
Examination Report dated Jun. 27, 2012 by the Intellectual Property Office of New Zealand for NZ patent application 587108 filed on Jan. 12, 2009 (Medicago, Inc. // D'Aoust et al.) (2 pages).
Examination Report dated Jan. 28, 2013 by the Intellectual Property Office of New Zealand for NZ patent application 587108 filed on Jan. 12, 2009 (Medicago, Inc. // D'Aoust et al.) (2 pages).
Examination Report dated Nov. 8, 2010 by the Intellectual Property Office of New Zealand for NZ patent application 582360 filed on Jul. 11, 2008 (Medicago, Inc. // D'Aoust et al.) (9 pages).
Examination Report dated Apr. 15, 2011 by the Intellectual Property Office of New Zealand for NZ patent application 590144 filed on Jul. 2, 2009 (Medicago, Inc. // D'Aoust et al.) (3 pages).

Office Action dated Apr. 5, 2013 by the Russian Patent Office for RU patent application Ru 2011105073/10 (2 pages).
Singapore Written Opinion dated May 2, 2011 by the Danish Patent Office for SG patent application 201000090-9 filed on Jul. 11, 2008 (Medicago, Inc. // D'Aoust et al.) (16 pages).
Certificate of Grant of Patent dated Apr. 30, 2012 by the Intellectual Property Office of Singapore for application 201000090-9 filed on Jul. 11, 2008 (Medicago, Inc. // D'Aoust et al.) (2 pages).
Written Opinion dated Apr. 18, 2012 by the Intellectual Property Office of Singapore for application 201009568-5 filed on Jul. 11, 2008 (Medicago, Inc. // D'Aoust et al.) (20 pages).
U.S. Appl. No. 61/022,775, filed Jan. 22, 2008, M.A. D'Aoust.
U.S. Appl. No. 61/244,786, filed Sep. 22, 2009, L.P. Vezina.
U.S. Appl. No. 61/013,272, filed Dec. 12, 2007, M.A. D'Aoust.
U.S. Appl. No. 60/990,603, filed Nov. 27, 2007, M.A. D'Aoust.
U.S. Appl. No. 60/959,414, filed Jul. 13, 2007, M.A. D'Aoust.
U.S. Appl. No. 61/220,161, filed Jun. 24, 2009, Couture.
International Preliminary Report on Patentability dated Nov. 12, 2009 for PCT/CA2008/001281 filed Jul. 11, 2008 and published as WO 2009/009876 on Jan. 22, 2009 (Medicago, Inc. // D'Aoust et al.) (11 pages).
International Search Report and Written Opinion dated Oct. 7, 2008 for PCT/CA2008/001281 filed Jul. 11, 2008 and published as WO 2009/009876 on Jan. 22, 2009 (Medicago, Inc. // D'Aoust et al.) (15 pages).
International Preliminary Report on Patentability dated Nov. 11, 2011 for PCT/CA2009/000941 filed Jul. 7, 2009 and published as WO 2010/003235 on Jan. 14, 2010 (Medicago, Inc. // Couture et al.) (1 pages).
International Search Report and Written Opinion dated Sep. 10, 2009 for PCT/CA2009/000941 filed Jul. 7, 2009 and published as WO 2010/003235 on Jan. 14, 2010 (Medicago, Inc. // Couture et al.) (13 pages).
International Preliminary Report on Patentability dated Nov. 5, 2010 for application PCT/CA2009/001040 filed Jul. 15, 2009 and published as WO 2010/006452 (Medicago, Inc. // Couture et al.) (14 pages).
International Search Report and Written Opinion dated Nov. 10, 2009 for PCT/CA2009/001040 filed Jul. 15, 2009 and published as WO 2010/006452 on Jan. 14, 2010 (Medicago, Inc. // Couture et al.) (13 pages).
International Preliminary Report on Patentability dated Jul. 27, 2010 for PCT/CA2009/000032 filed Jan. 12, 2009 and published as WO 2009/076778 on Jun. 25, 2009 (Medicago, Inc. // D'Aoust et al.) (9 pages).
International Search Report and Written Opinion dated Apr. 30, 2009 for PCT/CA2009/000032 filed Jan. 12, 2009 and published as WO 2009/076778 on Jun. 25, 2009 (Medicago, Inc. // D'Aoust et al.) (17 pages).
International Preliminary Report on Patentability dated Nov. 5, 2010 for PCT/CA2009/000926 filed Jul. 2, 2009 and published as WO 2010/003225 on Jan. 14, 2010 (Medicago, Inc. // D'Aoust et al.) (15 pages).
International Search Report and Written Opinion dated Oct. 1, 2009 for PCT/CA2009/000926 filed Jul. 2, 2009 and published as WO 2010/003225 on Jan. 14, 2010 (Medicago, Inc. // D'Aoust et al.) (17 pages).
International Search Report dated Jan. 6, 2011 for PCT/CA2010/001488 filed Sep. 21, 2010 and published as WO 2011/035422 on Mar. 31, 2011 (Medicago, Inc. // Vezina et al.) (5 pages).
Written Opinion dated Jan. 6, 2011 for PCT/CA2010/001488 filed Sep. 21, 2010 and published as WO 2011/035422 on Mar. 31, 2011 (Medicago, Inc. // Vezina et al.) (6 pages).
International Preliminary Report on Patentability dated Mar. 27, 2012 for PCT/CA2010/001488 filed Sep. 21, 2010 and published as WO 2011/035422 on Mar. 31, 2011 (Medicago, Inc. // Vezina et al.) (7 pages).
International Search Report dated Nov. 30, 2010 for PCT/CA2010/001489 filed Sep. 21, 2010 and published as WO 2011/035423 on Mar. 31, 2011 (Medicago, Inc. // Vezina et al.) (4 pages).
Written Opinion dated Nov. 30, 2010 for PCT/CA2010/001489 filed Sep. 21, 2010 and published as WO 2011/035423 on Mar. 31, 2011 (Medicago, Inc. // Vezina et al.) (6 pages).

(56) References Cited

OTHER PUBLICATIONS

International Preliminary Report on Patentability dated Mar. 27, 2012 for PCT/CA2010/001489 filed Sep. 21, 2010 and published as WO 2011/035423 on Mar. 31, 2011 (Medicago, Inc. // Vezina et al.) (7 pages).
Air GM. Sequence relationships among the hemagglutinin genes of 12 subtypes of influenza A virus, Proc Natl Acad Sci USA 78, pp. 7639-7643 (1981).
Arntzen, et al. Plant-derived vaccines and antibodies: potential and limitations, Vaccine 23, pp. 1753-1756 (2005).
Ausubel, et al. Chapter 9: Transfection by Electroporation, Current Protocols in Molecular Biology, John Wiley & Sons, New York (1998 and Supplements in 2001).
Aymard-Henry M, et al. Influenzavirus neuraminidase and neuraminidase-inhibition test procedures. Bull. Org. mond. Sante. Bull. Wid Hith Org. 48, pp. 199-202 (1973).
Bao, et al. The influenza virus resource at the National Center for Biotechnology Information, J Virol 82, pp. 596-601 (2008).
Berger, et al. Plant sterols: factors affecting their efficacy and safety as functional food ingredients, Lipids in Health and Disease 3, pp. 1-19 (2004).
Berman, et al. Correspondence: announcing the worldwide Protein Data Bank, Nat Struct Biol 10, p. 980 (2003).
Bilang, et al. The 3'-terminal region of the hygromycin-B-resistance gene is important for its activity in *Escherichia coli* and Nicotiana tabacum, Gene 100, pp. 247-250 (1991).
Bollag, et al. Purified JC virus T antigen derived from insect cells preferentially interacts with replication site II of the viral core origin under replication conditions, Virology 218, pp. 81-93 (1996).
Borisjuk, et al. Expression of avian flu antigen for bird immunization, Plant Biology & Botany Abstract Search (1 page) (2007).
Bouic PJD, et al. Plant sterols and sterolins: a review of their immune-modulating properties, Alt Med Rev 4, pp. 170-177 (1999).
Bouic PJD. Sterols and sterolins: new drugs for the immune system?, Drug Discovery Today 7, pp. 775-778 (2002).
Bouic PJD. The role of phytosterols and phytosterolins in immune modulation: a review of the past 10 years, Curr Opin Clin Nutrition Metabolic Care 4, pp. 471-475 (2001).
Bright RA, et al. Impact of glycosylation on the immunogenicity of a DNA-based influenza H5 HA vaccine, Virology 308, pp. 270-278 (2003).
Bright RA, et al. Influenza virus-like particles elicit broader immune responses than whole virion inactivated influenza virus or recombinant hemagglutinin, Vaccine 25, pp. 3871-3878 (2007).
Brigneti, et al. Viral pathogenicity determinants are suppressors of transgene silencing in Nicotiana benthamiana, EMBO J 17, pp. 6739-6746 (1998).
Chandler GL. Influenza hemagglutinin expression in Nicotiana tabacum and Nicotiana benthamiana, Dissertation, Baylor University (70 pages) (2007).
Chandrasekaran, et al. Glycan topology determines human adaptation of avian H5N1 virus hemagglutinin, Nat Biotechnol 26, pp. 107-113 (2008).
Charland N, et al. An innovative VLP-based technology to respond to global influenza vaccine needs, Seasonal and Pandemic Influenza Conference (2 pages) (2008).
Chen BJ, et al. Influenza virus hemagglutinin and neuraminidase, but not the matrix protein, are required for assembly and budding of plasmid-derived virus-like particles, J Virol 81, pp. 7111-7123 (2007).
Chen, et al. Stabilizing the glycosylation pattern of influenza B hemagglutinin following adaptation to growth in eggs, Vaccine 26, pp. 361-371 (2008).
Chiba M, et al. Diverse suppressors of RNA silencing enhance agroinfection by a viral replicon, Virology 346, pp. 7-14 (2006).
Cosgrove, D. Loosening of Plant Cell Walls by Expansins, Nature, vol. 407, pp. 321-326 (2000).
Crawford, et al. Baculovirus-derived hemagglutinin vaccines protect against lethal influenza infections by avian H5 and H7 subtypes, Vaccine 17, pp. 2265-2274 (1999).
Cross, et al. Studies on influenza haemagglutinin fusion peptide mutants generated by reverse genetics, EMBO J 20, pp. 4432-4442 (2001).
D'Aoust MA, et al. Influenza virus-like particles produced by transient 1-38 expression in Nicotiana benthamiana induce a protective immune response against a lethal viral challenge in mice, Plant Biotechnol J 6, pp. 930-940 (2008).
D'Aoust MA, et al. The production of hemagglutinin-based virus-like 1-38 particles in plants: a rapid, efficient and safe response to pandemic influenza, Plant Biotechnol J 8, pp. 607-619 (2010).
Davey MR, et al. Plant protoplasts: status and biotechnological perspectives, Biotechnology Advances 23, pp. 131-171 (2005).
DeBlock M, et al. Transformation of *Brassica napus* and *Brassica oleracea* using Agrobacterium tumefaciens and the expression of the bar and neo genes in the transgenic plants, Plant Physiology 91, pp. 694-701 (1989).
Diaz-Vivancos P, et al. The apoplastic antioxidant system in Prunus: response to long-term plum pox virus infection, J Exp Bot 57, pp. 3813-3824 (2006).
Firek et al. Secretion of a functional single-chain Fv protein in transgenic tobacco plants and cell suspension cultures, Plant Molecular Biology, vol. 23, Issue 4, pp. 861-870 (1993).
Fischer R, et al. Affinity-purification of a TMV-specific recombinant full-size antibody from a transgenic tobacco suspension culture, J Immunol Meth 226, pp. 1-10 (1999).
Fischer, et al. Towards molecular farming in the future: moving form diagnostic protein and antibody production in microbes to plants, Biotechnology and Applied Biochemistry, vol. 30, pp. 101-108 (1999).
Flandorfer, et al. Chimeric influenza A viruses with a functional influenza B virus neuraminidase or hemagglutinin, J Virol 77, pp. 9116-9123 (2003).
Frugis G, et al. MsJ1, an alfalfa DnaJ-like gene, is tissue-specific and transcriptionally regulated during cell cycle, Plant Mol Biol 40, pp. 397-408 (1999).
Galarza, et al. Virus-like particle (VLP) vaccine conferred complete protection against a lethal influenza virus challenge, Viral Immunol 18, pp. 244-251 (2005).
Gallagher, et al. Addition of carbohydrate side chains at novel sites on influenza virus hemagglutinin can modulate the folding, transport, and activity of the molecule, J Cell Biol 107, pp. 2059-2073 (1988).
Gallagher, et al. Glycosylation requirements for intracellular transport and function of the hemagglutinin of influenza virus, J Virol 66, pp. 7136-7145 (1992).
Gamblin, et al. The structure and receptor binding properties of the 1918 influenza hemagglutinin, Science 303, pp. 1838-1842 (2004).
Garcea & Gissmann. Virus-like particles as vaccines and vessels for the delivery of small molecules, Pharmaceut Biotechnol 15, pp. 513-517 (2004).
Garten R, et al. Emergence of a novel swine-origin influenza A (H1N1) virus in humans, New Eng J Med 361, pp. 1-10 (2009).
Garten, et al. Antigenic and genetic characteristics of swine-origin 2009 A(H1N1) Influenza viruses circulating in Humans. Science, vol. 325, pp. 197-201 (2009).
Garten, et al. Emergence of a Novel Swine-Origin Influenza A (H1N1) Virus in Humans. New England Journal of Medicine, vol. 360, No. 25 (2009).
Garten. Influenza A Virus (A/Califomia/Apr. 2009 H1N1) segment 4 hamegglutinin (HA) gene, Genbank Acces. FJ966082 (2009).
Gillim-Ross, et al. Emerging respiratory viruses: challenges and vaccine strategies, Clin Microbiol Rev 19, pp. 614-636 (2006).
Giridhar G, et al. Increased protoplast yield from oat leaves and bean internodes by non-injurious mechanical perturbation, Protoplasma 151, pp. 151-157 (1989).
Giritch, et al. Rapid High-Yield Expression of Full-Size IgG Antibodies in Plants Coinfected with Noncompeting Viral Vectors, PNAS, vol. 103, No. 40, pp. 14701-14706 (2006).
Golovkin, et al. Expression of avian flu antigen for bird immunization, Plant Biol Bot, 1 page (2007) (Abstract).
Gomez-Puertas, et al. Efficient formation of influeza virus-like particles: dependence on the expression levels of viral proteins, J Gen Virol 80, pp. 1635-1645 (1999).

(56) References Cited

OTHER PUBLICATIONS

Gomez-Puertas, et al. Influenza virus matrix protein is the major driving force in virus budding, J Virol 74, pp. 11536-11547 (2000).
Gomord & Faye. Posttranslational modification of therapeutic proteins in plants, Curr Opin Plant Biol 7, pp. 171-181 (2004).
Gomord, et al. Biopharmaceutical Production in Plants: Problems, Solutions and Opportunities, Trends in Biotechnology, vol. 23, No. 11, pp. 559-565 (2005).
Greco R, et al. Production of recombinant HIV-1/HBV virus-like particles in Nicotiana tabacum and *Arabidopsis thaliana* plants for a bivalent plant-based vaccine, Vaccine 25, pp. 8228-8240 (2007).
Grgacic & Anderson. Virus-like particles: Passport to immune recognition, Methods 40, pp. 60-65 (2006).
Grierson & Covey. Chapter 7: Genetic Transformation of Plants by Agrobacterium, in Plant Molecular Biology (19 pages) (1988).
Grierson & Covey. Chapter 8: Plant Viruses, in Plant Molecular Biology (26 pages) (1988).
Grierson, et al. Chapter 9: Genetic Engineering of Plants, in Plant Molecular Biology (20 pages) (1988).
Guerche, et al. Direct gene transfer by electroporation in *Brassica napus*, Plant Science 52, pp. 111-116 (1987).
Gupta, et al. O-Glycbase version 4.0: a revised database of O-glycosylated proteins, Nucl Acids Res 27, pp. 370-372 (1999).
Hahn BS, et al. Expression of hemagglutinin-neuraminidase protein of Newcastle disease virus in transgenic tobacco, Plant Biotechnol Rep 1, pp. 85-92 (2007).
Hamilton A, et al. Two classes of short interfering RNA in RNA silencing, EMBO J 21, pp. 4671-4679 (2002).
Harbury, et al. A switch between the two-, three-, and four-stranded coiled coils in GCN4 leucine zipper mutants, Science 262, pp. 1401-1407 (1993).
Hartl FU. Molecular chaperones in cellular protein folding, Nature 381, pp. 571-580 (1996).
Hellwig, et al. Plant Cell Cultures for the Production of Recombinant Proteins, Nature Biotechnology, vol. 22, No. 11, pp. 1415-1422 (2004).
Horimoto, et al. Generation of influenza A viruses with chimeric (Type A/B) hemagglutinins, J Virol 77, pp. 8031-8038 (2003).
Horsch, et al. A simple and general method for transferring genes into plants, Science 227, pp. 1229-1231 (1985).
Houston, N., et al. Phylogenetic Analyses Identify 10 Classes of the Protein Disulfide Isomerase Family in Plants, Including Single-Domain Protein Disulfide Isomerase-Related Proteins. Plant Physiology, vol. 137, pp. 762-778 (2005).
Howell, et al. Cloned Cauliflower Mosaic Virus DNA infects turnips (*Brassica rapa*), Science 208, p. 1265 (1980).
Huang Z, et al. Virus-like particle expression and assembly in plants: 1-38 hepatitis Band Norwalk viruses, Vaccine 23, pp. 1851-1858 (2005).
Huang, et al. A DNA replicon system for rapid high-level production of virus-like particles in plants, Biotechnol Bioeng 103, 706-714 (2009).
Huang, et al. High Level Rapid Production of Full-Size Monoclonal Antibodies in Plants by a Single-Vector DNA Replicon System, Biotechnology System, Biotechnology and Bioengineering, vol. 106, No. 1, (19 pages) (2010).
Huang, et al. Plant-derived measles virus hemagglutinin protein induces neutralizing antibodies in mice, Vaccine 19, pp. 2163-2171 (2001).
Hull, et al. Human-Derived, Plant-Produced monoclonal Antibody for the Treatment of Anthrax, Vaccine 23, pp. 2082-2086 (2005).
Influenza A virus (A/California/Apr. 2009(H1N1)) segment 4 hemagglutinin (HA) gene, Complete DNA Sequence, GenBank (2 pages) (Aug. 2010).
Ito T, et al. Receptor specificity of Influenza A viruses correlates with the agglutination of erythrocytes from different animal species, Virology 227, pp. 493-499 (1997).
Johansen, et al. Silencing on the Spot. Induction and Suppression of RNA Silencing in the Agrobacterium-Mediated Transient Expression System, Plant Physiology, vol. 126, No. 3, pp. 930-938 (2001).

Johansson BE. Immunization with influenza A virus hemagglutinin and neuraminidase produced in recombinant baculovirus results in a balanced and broadened immune response superior to conventional vaccine, Vaccine 17, pp. 2073-2080 (1999).
Kanda Y, et al. Comparison of biological activity among nonfucosylated therapeutic IgG1 antibodies with three different N-linked Fc oligosaccharides: the high-mannose, hybrid, and complex types, Glycobiol 17, pp. 104-118 (2007).
Kang SM, et al. Influenza vaccines based on virus-like particles, Virus Res 143, pp. 140-146 (2009).
Kaufman PB, et al. Chapter 16: Gene Tranfer and Expression in Plants, in Handbook of Molecular and Cellular Methods in Biology and Medicine (29 pages) (1995).
Klein, et al. High-velocity microprojectiles for delivering nucleic acids into living cells, Nature 327, pp. 70-73 (1987).
Knossow, et al. Variation and infectivity neutralization in influenza, Immunology 119, pp. 1-7 (2006).
Kobayashi, et al. Chaperones Hsp70 and Hsp40 Suppress Aggregate Formation and Apoptosis in Cultured Neuronal Cells Expressing Truncated Androgen Receptor Protein with Expanded Polyglutamine Tract, J Biol.1 Chem., vol. 275, No. 12, pp. 8772-8778 (2000).
Latham, et al. Formation of wild-type and chimeric influenza virus-like particles following simultaneous expression of only four structural proteins, J Virol 75, pp. 6154-6165 (2001).
Lefebvre, et al. Characterization of lipid rafts from Medicago truncatula root plasma membranes: a proteomic study reveals the presence of a raft-associated redox system, Plant Physiol 144, pp. 402-418 (2007).
Lin, et al. Genomic analysis of the Hsp70 superfamily in *Arabidopsis thaliana*, Cell Stress & Chaperones, pp. 201-208 (2001).
Liu & Lomonossoff. Agroinfection as a rapid method for propagating Cowpea mosaic virus-based constructs, J Virol Meth 105, pp. 343-348 (2002).
Low D, et al. Future of antibody purification, J Chromatography B 848, pp. 48-63 (2007).
Ma, et al. The production of recombinant pharmaceutical proteins in plants, Nature Reviews Genetics, vol. 4, pp. 794-805 (2003).
Macala, et al. Analysis of brain lipids by high performance thin-layer chromatography and densitometry, J Lipid Res 24, pp. 1243-1250 (1983).
Macario, AJL. Heat-shock proteins and molecular chaperones: implications for pathogenesis, diagnostics, and therapeutics, Int J Clin Lab Res 25, pp. 59-70 (1995).
Mansour, et al. Plasma membrane lipid alterations induced by NaCl in winter wheat roots, Physiologia Plantarum 92, pp. 473-478 (1994).
Marozin S, et al. Antigenic and genetic diversity among swine influenza A H1N1 and H1N2 viruses in Europe, J Gen Virol 83, pp. 735-745 (2002).
Mason HS, et al. Expression of hepatitis B surface antigen in transgenic plants, Proc Natl Acad Sci USA 89, pp. 11745-11749 (1992).
Mason HS, et al. Expression of Norwalk Virus capsid protein in transgenic tobacco and potato and its oral immunogenicity in mice, Proc Natl Acad Sci USA 93, pp. 5335-5340 (1996).
Mattanovich, et al. Efficient transformation of *Agrobacterium* spp. by electroporation, Nucl Acids Res 17, p. 6747 (1989).
McCauley & Mahy. Structure and function of the influenza virus genome, Biochem J 211, pp. 281-294 (1983).
McCormick AA, et al. Rapid production of specific vaccines for lymphoma by expression of the tumor-derived single-chain FV epitopes in tobacco plants, Proc Natl Acad Sci USA 96, pp. 703-708 (1999).
Medeiros R, et al. Hemagglutinin residues of recent human A (H3N2) Influenza viruses that contribute to the inability to agglutinate chicken erythrocytes, Virology 289, pp. 74-85 (2001).
Mena I, et al. Rescue of a synthetic chloramphenicol acetyltransferase RNA into influenza virus-like particles obtained from recombinant plasmids, J Virol 70, pp. 5016-5024 (1996).
Mett, et al. A plant-produced influenza subunit vaccine protects ferrets against virus challenge, Influenza and Other Respiratory Viruses 2, pp. 33-40 (2008).

(56) References Cited

OTHER PUBLICATIONS

Miki & Iyer. Chapter 35: Fundamentals of Gene Transfer in Plants, in Plant Metabolism (23 pages) (1997).
Moehnke, et al. The expression of a mountain cedar allergen comparing plant-viral apoplastic and yeast expression systems, Biotechnol Lett 30, pp. 1259-1264 (2008).
Mongrand S, et al. Lipid rafts in higher plant cells: purification and characterization of Triton X-100-insoluble microdomains from Tobacco plasma membrane, J Bilo Chem 279, pp. 36277-36286 (2004).
Musiychuk K, et al. A launch vector for the production of vaccine antigens in plants, Influenza Other Resp Vir 1, pp. 19-25 (2007).
Nakahara, et al. Glycoconjugate Data Bank: Structures—an annotated glycan primary structure verification service, Nucl Acids Res 36, pp. D368-D371 (2008).
Nayak & Reichl. Neuraminidase activity assays for monitoring MDCK cell culture derived influenza virus, J Virol Meth 122, pp. 9-15 (2004).
Nemchinov, et al. Transient expression of the ectodomain of matrix protein 2 (M2e) of avian influenza A virus in plants. Protein Expression and Purification, vol. 56, pp. 153-159 (2007).
Neuhause G, et al. Transgenic rapeSeed plants obtained by the microinjection of DNA into microspore-derived embryoids, Theor Appl Genet 75, pp. 30-36 (1987).
Neumann, et al. Plasmid-driven formation of influenza virus-like particles, J Virol 74, pp. 547-551 (2000).
Newell JM, et al. Vacuole development in cultured evacuolated oat mesophyll protoplasts, J Exp Botany 49, pp. 817-827 (1998).
Nishimura, et al. Isolation of intact plastids from protoplasts from Castor Bean endosperm, Plant Physiol 62, pp. 40-43 (1978).
Nuttall, et al. ER-resident chaperone interactions with recombinant antibodies in transgenic plants, Eur J Biochem 269, pp. 6042-6051 (2002).
Olsen, et al. Immunogenicity and efficacy of baculovirus-expressed and DNA-based equine influenza virus hemagglutinin vaccines in mice, Vaccine 15, pp. 1149-1156 (1997).
Parsell DA & Lindquist S. The function of heat-shock proteins in stress tolerance: degradation and reactivation of damaged proteins, Ann Rev Genet 27, pp. 437-496 (1993).
Paszkowski & Saul. Direct Gene Transfer to Plants, in Methods for Plant Molecular Biology (19 pages) (1988).
Pereira-Leal JB, et al. The origins and evolution of functional modules: lessons from protein complexes, Philos Trans R Soc Lond B Biol Sci 361, pp. 507-517 (2006).
Petersen & Alfermann. Chapter 17: Plant Cell Cultures. Biotechnology Set, Second Edition, Section 1.3, pp. 578-580 (2008).
Plotkin, et al. Hemagglutinin sequence clusters and the antigenic evolution of influenza A virus, Proc Natl Acad Sci USA 99, pp. 6263-6268 (2002).
Potrykus I, et al. Protoplasts: Isolation, Culture, Plant Regeneration, in Methods for Plant Molecular Biology (31 pages) (1988).
Potter & Heller. Transfection by electroporation, Curr Prot Mol Biol (12 pages) (2003).
Power JB, et al. Fusion and Transformation of Plant Protoplasts, in Methods for Plant Molecular Biology (19 pages) (1988).
Pushko P, et al. Influenza virus-like particles comprised of the HA, NA, and M1 proteins of H9N2 influenza virus induce protective immune responses in BALB/c mice, Vaccine 23, pp. 5751-5759 (2005).
Pwee, et al. The pea plastocyanin promoter directs cell-specific but not full light-regulated expression in transgenic tobacco plants, Plant J 3, pp. 437-449 (1993).
Quan FS, et al. Virus-like particle vaccine induces protective immunity against homologous and heterologous strains of influenza virus, J Virol 81, pp. 3514-3524 (2007).
Razdan MK. Chapter 12: Somatic Hybridisation and Cybridisation, in Introduction to Plant Tissue Culture (30 pages) (2003).
Regnard, et al. High Level Protein Expression in Plants Through the Use of a Novel Autonomously Replicating Geminivirus Shuttle Vector, Plant Biotechnology Journal, vol. 8, pp. 38-46 (2010).
Rivard, et al. An in-built proteinase inhibitor system for the protection of recombinant proteins recovered from transgenic plants, Plant Biotechnology Journal, vol. 4, No. 3, pp. 359-368 (2006).
Rowe, et al. Detection of antibody to avian influenza A (H5N1) virus in human serum by using a combination of serologic assays, J Clin Microbiol 37, pp. 937-943 (1999).
Roy, et al. Virus-like particles as a vaccine delivery system: myths and facts, Human Vaccines 4, pp. 5-12 (2008).
Saelens, et al. Protection of Mice Against a Lethal Influenza Virus Challenge After Immunization with Yeast-Derived Secreted Influenza Virus Hemagglutinin, Eur. J. Biochem, vol. 260, pp. 166-175 (1999).
Sainsbury F & Lomonossoff GP. Extremely high-level and rapid transient protein production in plants without the use of viral replication, Plant Physiol 148, pp. 1212-1218 (2008).
Sainsbury F, et al. Expression of multiple proteins using full-length and deleted versions of cowpea mosaic virus RNA-2, Plant Biotechnol J 6, pp. 82-92 (2008).
Saint-Jore-Dupas C, et al. From planta to pharma with glycosylation in the toolbox, Trends in Biotechnol 25, pp. 317-323 (2007).
Selenko N, et al. CD20 antibody (C2B8)-induced apoptosis of lymphoma cells promotes phagocytosis by dendritic cells and cross-priming of CD8+ cytotoxic T cells, Leukemia 15, pp. 1619-1626 (2001).
Salzberg, et al. Genome analysis linking recent European and African influenza (H5N1) viruses, Emerg Infect Dis 13, pp. 713-718 (2007).
Santi L, et al. An efficient plant viral expression system generating orally immunogenic Norwalk virus-like particles, Vaccine 26, pp. 1846-1854 (2008).
Scheid OM, et al. Reversible inactivation of a transgene in *Arabidopsis thaliana*, Mol Gen Genet 228, pp. 104-112 (1991).
Schillberg S, et al. Apoplastic and cytosolic expression of full-size antibodies and antibody fragments in Nicotiana tabacum, Transgenic Res 8, pp. 255-263 (1999).
Schillberg S, et al. Molecular farming of recombinant antibodies in plants, Cell Mol Life Sci 60, pp. 433-445 (2003).
Schuler & Zielinski. Chapter 8: Transformation of Leaf Discs with Agrobacterium, in Methods in Plant Molecular Biology (14 pages) (1989).
Shoji Y, et al. Plant-expressed HA as a seasonal influenza vaccine candidate, Vaccine 26, pp. 2930-2934 (2008).
Shorrosh BS & Dixon RA. Molecular cloning of a putative plant endomembrane protein resembling vertebrate protein disulfide-isomerase and a phosphatidylinositol-specific phospholipase C, Proc Natl Acad Sci USA 88, pp. 10941-10945 (1991).
Shorrosh, B. et al. Sequence analysis and developmental expression of an alfalfa protein disulfide isomerase. Plant Molecular Biology, vol. 19, pp. 319-321 (1992).
Skehel & Wiley. Receptor binding and membrane fusion in virus entry: the influenza hemagglutinin, Ann Rev Biochem 69, pp. 531-569 (2000).
Smith ML, et al. Structural characterization of plant-derived hepatitis B surface antigen employed in oral immunization studies, Vaccine 21, pp. 4011-4021 (2003).
Spitsin, et al. Immunological assessment of plant-derived avian flu H5/HA1 variants, Vaccine, vol. 27, No. 9, pp. 1289-1292 (2009).
Squires B, et al. BioHealthBase: informatics support in the elucidation of influenza virus host-pathogen interactions and virulence, Nucl Acids Res 36, pp. D497-D503 (2008).
Sriraman, et al. Recombinant anti-hCG antibodies retained in the endoplasmic reticulum of transformed plants lack core-xylose and core-α(1,3)-fucose residues, Plant Biotechnol J 2, pp. 279-287 (2004).
Staehelin LA. The plant ER: a dynamic organelle composed of a large number of discrete functional domains, Plant J 11, pp. 1151-1165 (1997).
Suzuki Y. Sialobiology of influenza: molecular mechanism of host range variation of influenza viruses, Biol Pharm Bull 28, pp. 399-408 (2005).
Szyperski T, et al. Structure comparison of human glioma pathogenesis-related protein GliPR and the plant pathogenesis-related protein

(56) References Cited

OTHER PUBLICATIONS

P14a indicates a functional link between the human immune system and a plant defense system, Proc Natl Acad Sci 95, pp. 2262-2266 (1998).
Tacket CO, et al. Human immune responses to a novel Norwalk virus vaccine delivered in transgenic potatoes, J Infect Dis 182, pp. 302-305 (2000).
Toukach, et al. Sharing of worldwide distributed carbohydrate-related digital resources: online connection of the Bacterial Carbohydrate Structure DataBase and GLYCOSCIENCES.de, Nucl Acids Res 35, pp. D280-D286 (2007).
Treanor, et al. Safety and immunogenicity of a baculovirus-expressed hemagglutinin influenza vaccine: a randomized controlled trial, JAMA 297, pp. 1577-1582 (2007).
Vaccaro L, et al. Plasticity of influenza haemagglutinin fusion peptides and their interaction with lipid bilayers, Biophys J 88, pp. 25-36 (2005).
Van Ree R, et al. β(1,2)-xylose and α(1,3)-fucose residues have a strong contribution in IgE binding to plant glycoallergens, J Biol Chem 275, pp. 11451-11458 (2000).
Varsani, et al. Expression of Human papillomavirus type 16 major capsid protein in transgenic Nicotiana tabacum cv. Xanthi, Arch Viral 148, pp. 1771-1786 (2003).
Vezina, et al. Transient co-expression for fast and high-yield production of antibodies with human-like N-glycans in plants, Plant Biotechnol J 7, pp. 442-455 (2009).
Vigerust, et al. N-Linked Glycosylation Attenuates H3N2 Influenza Viruses, Journal of Virology, vol. 81, No. 16, pp. 8593-8600 (2007).
Voinnet O, et al. An enhanced transient expression system in plants based on suppression of gene silencing by the p19 protein of tomato bushy stunt virus, Plant J 33, pp. 949-956 (2003).
Wagner, et al. Interdependence of hemagglutinin glycosylation and neuraminidase as regulators of influenza virus growth: a study by reverse genetics, J Virol 74, pp. 6316-6323 (2000).
Wakefield, et al. RNA-binding properties of influenza A virus matrix protein M1, Nucl Acids Res 17, pp. 8569-8580 (1989).
Wang, et al. Expression and purification of an influenza hemagglutinin—one step closer to a recombinant protein-based influenza vaccine, Vaccine 24, pp. 2176-2185 (2006).
Wei, et al. Comparative efficacy of neutralizing antibodies elicited by recombinant hemagglutinin proteins from avian H5N1 influenza virus, J Virol 82, pp. 6200-6208 (2008).
Weldon, et al. Enhanced Immunogenicity of Stabilized Trimeric Soluble Influenza Hemagglutinin, PLOS One, vol. 5, No. 9, e12466, pp. 1-8 (2010).
Wilson IBH, et al. Core α1,3-fucose is a key part of the epitope recognized by antibodies reacting against plant N-linked oligosaccharides and is present in a wide variety of plant extracts, Glycobiol 8, pp. 651-661 (1998).
Wydro M, et al. Optimization of transient Agrobacterium-mediated gene expression system in leaves of Nicotania benthamiana, Acta Biochimica Polonica 53, pp. 289-298 (2006).
Preliminary Amendment filed Mar. 22, 2012 for U.S. Appl. No. 13/497,757, filed Sep. 21, 2010 (Vezina et al.) (4 pages).
Preliminary Amendment filed Jan. 23, 2013 for U.S. Appl. No. 13/748,531, filed Jan. 23, 2013 (D'Aoust et al.) (3 pages).
Requirement for Restriction/Election dated Mar. 25, 2013 for U.S. Appl. No. 13/748,531, filed Jan. 23, 2013 (D'Aoust et al.) (9 pages).
Response to Requirement for Restriction/Election filed Apr. 25, 2013 for U.S. Appl. No. 13/748,531, filed Jan. 23, 2013 (D'Aoust et al.) (3 pages).
Non-Final Rejection dated Sep. 23, 2013 for U.S. Appl. No. 13/748,531, filed Jan. 23, 2013 (D'Aoust et al.) (10 pages).
Preliminary Amendment filed Jan. 13, 2010 for U.S. Appl. No. 12/669,033, filed Jun. 11, 2010 (D'Aoust et al.) (7 pages).
Requirement for Restriction/Election dated Aug. 13, 2012 for U.S. Appl. No. 12/669,033, filed Jun. 11, 2010 (D'Aoust et al.) (8 pages).
Response to Requirement for Restriction/Election filed Sep. 11, 2012 for U.S. Appl. No. 12/669,033, filed Jun. 11, 2010 (D'Aoust et al.) (5 pages).
Non-Final Rejection dated Oct. 4, 2012 for U.S. Appl. No. 12/669,033, filed Jun. 11, 2010 (D'Aoust et al.) (10 pages).
Response to Non-Final Rejection filed Nov. 2, 2012 for U.S. Appl. No. 12/669,033, filed Jun. 11, 2010 (D'Aoust et al.) (2 pages).
Miscellaneous Communication dated May 21, 2012 for U.S. Appl. No. 12/669,033, filed Jun. 11, 2010 (D'Aoust et al.) (2 pages).
Notice of Abandonment dated Jul. 10, 2013 for U.S. Appl. No. 12/669,033, filed Jun. 11, 2010 (D'Aoust et al.) (2 pages).
Notice of Abandonment dated Jul. 25, 2013 for U.S. Appl. No. 12/863,772, filed Jul. 20, 2010 (D'Aoust et al.) (2 pages).
Non-Final Rejection dated Dec. 14, 2012 for U.S. Appl. No. 12/863,772, filed Jul. 20, 2010 (D'Aoust et al.) (8 pages).
Response to Requirement for Restriction/Election filed Oct. 29, 2012 for U.S. Appl. No. 12/863,772, filed Jul. 20, 2010 (D'Aoust et al.) (3 pages).
Requirement for Restriction/Election dated Sep. 27, 2012 for U.S. Appl. No. 12/863,772, filed Jul. 20, 2010 (D'Aoust et al.) (9 pages).
Preliminary Amendment filed Jul. 20, 2010 for U.S. Appl. No. 12/863,772, filed Jul. 20, 2010 (D'Aoust et al.) (7 pages).
1$^{st}$ Prelimianry Amendment filed Jan. 4, 2013 for U.S. Appl. No. 13/734,886, filed Jan. 4, 2013 (D'Aoust et al.) (3 pages).
2$^{nd}$ Prelimianry Amendment filed Mar. 22, 2013 for U.S. Appl. No. 13/734,886, filed Jan. 4, 2013 (D'Aoust et al.) (13 pages).
3$^{rd}$ Prelimianry Amendment filed Aug. 22, 2013 for U.S. Appl. No. 13/734,886, filed Jan. 4, 2013 (D'Aoust et al.) (5 pages).
Non-Final Rejection dated Nov. 25, 2013 for U.S. Appl. No. 13/734,886, filed Jan. 4, 2013 (D'Aoust et al.) (12 pages).
Preliminary Amendment filed Mar. 22, 2012 for U.S. Appl. No. 13/497,767, filed Mar. 22, 2012 (D'Aoust et al.) (4 pages).
Office Action dated May 21, 2013 by the Australian Intellectual Property Office for AU patent application No. 2008278222 filed on Jul. 11, 2008 (Medicago, Inc. // D'Aoust et al.) (3 pages).
Office Action dated Mar. 1, 2013 by the Canadian Intellectual Property Office for CA patent application No. 2,707,235 filed on Jan. 12, 209 (Medicago, Inc. // D'Aoust et al.) (2 pages).
Office Action dated Sep. 28, 2012 by the Canadian Intellectual Property Office for CA patent application No. 2,707,235 filed on Jan. 12, 2009 (Medicago, Inc. // D'Aoust et al.) (2 pages).
Office Action dated Jun. 7, 2012 by the Canadian Intellectual Property Office for CA patent application No. 2,707,235 filed on Jan. 12, 2009 (Medicago, Inc. // D'Aoust et al.) (3 pages).
Office Action dated Jun. 1, 2011 by the Canadian Intellectual Property Office for CA patent application No. 2,707,235 filed on Jan. 12, 2009 (Medicago, Inc. // D'Aoust et al.) (5 pages).
Office Action dated Mar. 1, 2013 by the Canadian Intellectual Property Office for CA patent application No. 2,693,956 filed on Jul. 11, 2008 (Medicago, Inc. // D'Aoust et al.) (2 pages).
Office Action dated Oct. 16, 2012 by the Canadian Intellectual Property Office for CA patent application No. 2,693,956 filed on Jul. 11, 2008 (Medicago, Inc. // D'Aoust et al.) (2 pages).
Office Action dated Jan. 20, 2012 by the Canadian Intellectual Property Office for CA patent application No. 2,693,956 filed on Jul. 11, 2008 (Medicago, Inc. // D'Aoust et al.) (2 pages).
Office Action dated Sep. 22, 2011 by the Canadian Intellectual Property Office for CA patent application No. 2,693,956 filed on Jul. 11, 2008 (Medicago, Inc. // D'Aoust et al.) (3 pages).
Office Action dated Jan. 26, 2011 by the Canadian Intellectual Property Office for CA patent application No. 2,693,956 filed on Jul. 11, 2008 (Medicago, Inc. // D'Aoust et al.) (3 pages).
Office Action dated Nov. 27, 2012 by the State Intellectual Property Office of People's Republic of China for CN patent application No. 200980109781.5 filed on Jan. 12, 2009 (Medicago, Inc. // D'Aoust et al.) (5 pages).
Office Action dated Jan. 21, 2012 by the State Intellectual Property Office of People's Republic of China for CN patent application No. 200980109781.5 filed on Jan. 12, 2019 (Medicago, Inc. // D'Aoust et al.) (9 pages).
Office Action dated Feb. 21, 2013 by the State Intellectual Property Office of People's Republic of China for CN patent application No. 200880107072.9 filed on Jan. 12, 2009 (Medicago, Inc. // D'Aoust et al.) (6 pages).

(56) References Cited

OTHER PUBLICATIONS

Office Action dated Jul. 24, 2012 by the State Intellectual Property Office of People's Republic of China for CN patent application No. 200880107072.9 filed on Jan. 12, 2009 (Medicago, Inc. // D'Aoust et al.) (10 pages).
Office Action dated Sep. 27, 2011 by the State Intellectual Property Office of People's Republic of China for CN patent application No. 200880107072.9 filed on Jan. 12, 2009 (Medicago, Inc. // D'Aoust et al.) (8 pages).
Office Action dated May 30, 2013 by the State Intellectual Property Office of People's Republic of China for CN patent application No. 200980134868.8 filed on Jul. 2, 2009 (Medicago, Inc. // D'Aoust et al.) (5 pages).
Office Action dated Jul. 16, 2012 by the State Intellectual Property Office of People's Republic of China for CN patent application No. 200980134868.8 filed on Jul. 2, 2009 (Medicago, Inc. // D'Aoust et al.) (6 pages).
Office Action dated Mar. 1, 2013 by the State Intellectual Property Office of People's Republic of China for CN patent application No. 201080042333.0 (Medicago, Inc. // D'Aoust et al.) (12 pages).
Office Action dated Dec. 13, 2011 by the Eurasian Patent Office for EA patent application No. 201000195/28 (Medicago, Inc. // D'Aoust et al.) (4 Pages).
Office Action dated Jun. 13, 2012 by the Eurasian Patent Office for application No. 201000195/28 (Medicago, Inc. // D'Aoust et al) (1 Page).
Office Action dated Aug. 28, 2012 by the Eurasian Patent Office for application No. 201001198 filed Feb. 7, 2009 (Medicago, Inc. // D'Aoust et al) (5 Pages).
Office Action dated Apr. 24, 2013 by the Eurasian Patent Office for application No. 201001198 filed Feb. 7, 2009 (Medicago, Inc. // D'Aoust et al) (3 Pages).
Office Action dated Nov. 18, 2011 by the Egyptian Patent Office for EG patent application No. PCT 1222/2010 filed on Jan. 12, 2009 (Medicago, Inc. // D'Aoust et al.) (9 pages).
Office Action dated Oct. 26, 2012 by the European Patent Office for EP patent application No. 2008783201.0 filed on Jul. 11, 2008 (Medicago, Inc. // D'Aoust et al.) (XX pages).
Decision to Grant dated Mar. 31, 2013 by the European Patent Office for EP patent application No. 2008783201.0 filed on Jul. 11, 2008 (Medicago, Inc. // D'Aoust et al.) (2 pages).
Extended European Search Report dated Sep. 13, 2010 by the European Patent Office for EP patent application No. 2008783201.0 filed on Jul. 11, 2008 (Medicago, Inc. // D'Aoust et al.) (9 pages).
European Search Report dated May 26, 2011 by the European Patent Office for EP patent application No. 2008783201.0 filed on Jul. 11, 2008 (Medicago, Inc. // D'Aoust et al.) (4 pages).
Extended European Search Report dated Mar. 7, 2011 by the European Patent Office for EP patent application No. 2009700061.6 filed on Jan. 12, 2019 (Medicago, Inc. // D'Aoust et al.) (11 pages).
Decision to Grant dated Aug. 17, 2012 by the European Patent Office for EP patent application No. 2009700061.6 filed on Jan. 12, 2009 (Medicago, Inc. // D'Aoust et al.) (1 page).
Extended European Search Report dated Aug. 9, 2011 by the European Patent Office for EP patent application No. 2009793741.1 filed on Jul. 2, 2009 (Medicago, Inc. // D'Aoust et al.) (9 pages).
Extended European Search Report dated Jan. 28, 2013 by the European Patent Office for EP patent application No. 10818190.0 filed on Sep. 21, 2010 (Medicago, Inc. // Vezina et al.) (6 pages).
Extended European Search Report dated Jan. 3, 2013 by the European Patent Office for EP patent application No. 108181918 filed on Sep. 21, 2010 (Medicago, Inc. // Vezina et al.) (5 pages).
Extended European Search Report dated Feb. 15, 2013 by the European Patent Office for EP patent application No. 121810774 filed on Jul. 2, 2009 (Medicago, Inc. // D'Aoust et al.) (8 pages).
Office Action dated Sep. 18, 2012 by the Indonesian Patent Office for ID application No. ID W-0020102481 filed Jul. 11, 2008 (Medicago, Inc. // D'Aoust et al.) (2 Pages).

Office Action dated Oct. 25, 2012 by the Registrar of Patents of Israel for IL patent application No. 210215 filed on Jul. 2, 2009 (Medicago, Inc. // D'Aoust et al.) (2 pages).
Office Action dated May 9, 2012 by the Registrar of Patents of Israel for IL patent application 206967 filed on Jan. 12, 2009 (Medicago, Inc. // D'Aoust et al.) (2 pages).
Office Action dated May 8, 2012 by the Registrar of Patents of Israel for IL patent application 203018 filed on Jan. 12, 2009 (Medicago, Inc. // D'Aoust et al.) (2 pages).
Office Action dated Mar. 6, 2013 by the Mexican Patent Office for MX patent application No. MX/a/2010/000525 filed on Jul. 11, 2008 (Medicago, Inc. // D'Aoust et al) (4 pages).
Office Action dated Mar. 6, 2013 by the Mexican Patent Office for MX patent application No. MX/a/2010/007962 filed on Jan. 12, 2009 (Medicago, Inc. // D'Aoust et al) (4 pages).
Office Action dated Mar. 6, 2013 by the Mexican Patent Office for MX application No. MX/a/2010/000459 filed on Jul. 22, 2009 (Medicago, Inc. // D'Aoust et al) (3 pages).
Examination Report dated Nov. 14, 2012 by the Intellectual Property Office of New Zealand for NZ patent application 598481 (2 pages).
Examination Report dated Nov. 15, 2012 by the Intellectual Property Office of New Zealand for NZ patent application 598508 (2 pages).
Examination Report dated Mar. 21, 2011 by the Intellectual Property Office of New Zealand for NZ patent application 587108 filed on Jan. 12, 2009 (Medicago, Inc. // D'Aoust et al.) (2 pages).
U.S. Appl. No. 13/380,346, filed Apr. 17, 2012, M. Couture.
U.S. Appl. No. 61/446,889, filed Mar. 23, 2011, M. Couture.
U.S. Appl. No. 14/066,552, filed Sep. 20, 2013, M. Couture.
Preliminary Amendment filed Sep. 20, 2013 for U.S. Appl. No. 14/006,552, filed Mar. 22, 2012 (D'Aoust et al.) (5 pages).
Decision regarding Petition mailed Nov. 26, 2013 for U.S. Appl. No. 13/380,346, filed Apr. 17, 2012 (Couture et al.) (3 pages).
Amendment in Response to Decision regarding Petition with renewed Petition filed Nov. 16, 2013 for U.S. Appl. No. 13/380,346, filed Apr. 17, 2012 (Couture et al.) (13 pages).
Non-Final Office Action dated Nov. 5, 2013 for U.S. Appl. No. 13/380,346, filed Apr. 17, 2012 (Couture et al.) (12 pages).
Decision regarding Petition mailed Oct. 10, 2013 for U.S. Appl. No. 13/380,346, filed Apr. 17, 2012 (Couture et al.) (3 pages).
Preliminary Amendment filed Aug. 20, 2013 for U.S. Appl. No. 13/380,346, filed Apr. 17, 2012 (Couture et al.) (26 pages).
Request for Participation in PPH Program filed Aug. 20, 2013 for U.S. Appl. No. 13/380,346, filed Apr. 17, 2012 (Couture et al.) (2 pages).
Preliminary Amendment filed Mar. 20, 2012 for U.S. Appl. No. 13/380,346, filed Apr. 17, 2012 (Couture et al.) (4 pages).
International Preliminary Report on Patentability dated Jan. 4, 2012 for PCT/CA2010/000983 filed Jun. 25, 2010 and published as WO 2010/148511 on Dec. 29, 2010 (Medicago, Inc. // Couture et al.) (9 pages).
International Search Report dated Dec. 29, 2010 for PCT/CA2010/000983 filed Jun. 25, 2010 and published as WO 2010/148511 on Dec. 29, 2010 (Medicago, Inc. // Couture et al.) (5 pages).
Written Opinion dated Sep. 14, 2010 for PCT/CA2010/000983 filed Jun. 25, 2010 and published as WO 2010/148511 on Dec. 29, 2010 (Medicago, Inc. // Couture et al.) (8 pages).
International Preliminary Report on Patentability dated Sep. 24, 2013 for PCT/CA2012/050180 filed Mar. 23, 2012 and published as WO 2012/126123 on Sep. 27, 2012 (Medicago, Inc. // Couture et al.) (8 pages).
International Search Report dated Sep. 27, 2012 for PCT/CA2012/050180 filed Mar. 23, 2012 and published as WO 2012/126123 on Sep. 27, 2012 (Medicago, Inc. // Couture et al.) (5 pages).
Written Opinion dated Jun. 11, 2012 for PCT/CA2012/050180 filed Mar. 23, 2012 and published as WO 2012/126123 on Sep. 27, 2012 (Medicago, Inc. // Couture et al.) (7 pages).
Requirement for Restriction/Election dated Sep. 27, 2012 by the USPTO for U.S. Appl. No. 12/863,772, filed Aug. 26, 2010 (1st Named Inventor—D'Aoust) (9 pages).

(56) References Cited

OTHER PUBLICATIONS

Non-final Rejection dated Dec. 14, 2012 by the USPTO for U.S. Appl. No. 12/863,772, filed Aug. 26, 2010 (1st Named Inventor—D'Aoust) (8 pages).
Non-final Rejection dated Oct. 4, 2012 by the USPTO for U.S. Appl. No. 12/669,033, filed Jun. 11, 2010 (1st Named Inventor—D'Aoust) (10 pages).
Requirement for Restriction/Election dated Mar. 25, 2013 by the USPTO for U.S. Appl. No. 13/748,531, filed Jan. 23, 2013 (1st Named Inventor—D'Aoust) (9 pages).
Garten. Influenza A Virus (A/California/Apr. 2009 H1N1) segment 4 hamegglutinin (HA) gene, Genbank Acces. FJ966082 (2009).
Abdel-Salam, et al., "Purification, serology and molecular detection of Egyptian isolates of banana bunchy top babuvirus and faba bean necrotic yellows nanovirus," Arab J. Biotech, 7(1), pp. 141-155, 2004.
Denis, et al., "Immunogenicity of papaya mosaic virus-like particles fused to a hepatitis C virus epitope: Evidence for the critical function of multimerization," Virology 363 (2007) pp. 59-68.
Liu, et al., "Cowpea mosaic virus-based systems for the production of antigens and antibodies in plants," Vaccine 23 (2005) pp. 1788-1792.
Takebe, et al., "Isolation of tobacco mesophyll cells in intact and active state," Plant and Cell Physiol., 9, 115-124 (1968).
Certificate of Grant dated Nov. 12, 2015 by the Australian Patent Office for AU 2010/300033 (1st Named Inventor—Couture; Applicant—Medicago Inc.) (1 page).
Communication pursuant to Article 94(3) EPC dated Nov. 17, 2015 for EP 10818191.8 (Applicant—Medicago, Inc.) (6 pages).
Translated Summary of Indonesian Office Action dated Dec. 3, 2015 for application W-00201201507 (Applicant—Medicago, Inc.) (1 page).
Fourth Office Action dated Nov. 26, 2015 by the State Intellectual Property Office of the People's Republic of China for application CN 201310021693.8 (Applicant—Medicago, Inc.) (7 pages—English Translation).
English Translation of Eurasian Office Action dated Oct. 1, 2015 for application EA201001198 (1st Named Inventor—Couture; Applicant—Medicago Inc.) (3 pages).
Notification of Allowability dated Sep. 18, 2015 for Indonesian application ID W-0020102481 (Applicant—Medicago Inc.) (2 pages).
Notice of Final Rejection dated Jan. 22, 2016 by the Korean Intellectual Property Office for Application No. 10-2010-7018343 (Applicant—Medicago Inc.) (4 pages // English Translation).
Advisory Action issued by the USPTO dated Nov. 3, 2015 for U.S. Appl. No. 13/734,886, filed Jan. 4, 2013 and published as US 2013/0183341 on Jul. 18, 2013 (1st Named Inventor—D'Aoust; Applicant—Medicago, Inc.) (3 pages).
Non-Final Office Action issued by the USPTO dated Feb. 12, 2016 for U.S. Appl. No. 13/734,886, filed Jan. 4, 2013 and published as US 2013/0183341 on Jul. 18, 2013 (1st Named Inventor—D'Aoust; Applicant—Medicago, Inc.) (13 pages).
Final Office Action issued by the USPTO dated Oct. 6, 2015 for U.S. Appl. No. 13/748,531, filed Jan. 23, 2013 and published as US 2013/0142826 on Jun. 6, 2013 (1st Named Inventor—D'Aoust; Applicant—Medicago, Inc.) (12 pages).
Non-Final Office Action issued by the USPTO dated Dec. 2, 2015 for U.S. Appl. No. 13/003,570, filed Apr. 26, 2011 and published as US 2011/10293650 on Dec. 1, 2011 (1st Named Inventor—D'Aoust; Applicant—Medicago, Inc.) (15 pages).
Communication pursuant to Article 94(3) EPC dated Jul. 26, 2016 for EP 10818191.8 (Applicant—Medicago, Inc.) (4 pages).
Fifth Office Action dated Aug. 12, 2016, by the State Intellectual Property Office of the People's Republic of China for application CN 201310021693.8 (Applicant—Medicago, Inc. (6 pages—English Translation).
GenBank Accession No. EF541394.1, Mar. 19, 2007, available at www.ncbi.nlm.nih.gov/nuccore/145284449?sat=12&satkey=4030144 (2 pages).

Naito, et al., "Involvement of Hsp90 in Assembly and Nuclear Import of Influenza Virus RNA Polymerase Subunits," Journal of Virology, 2007, pp. 1339-1349.
Non-Final Office Action issued by the USPTO dated Feb. 22, 2016, for U.S. Appl. No. 13/497,757, filed Mar. 22, 2012 and published as US 2012/0178149 on Jul. 12, 2012 (1st Named Inventor—Vezina; Applicant—Medicago, Inc.) (17 pages).
Notice of Allowance issued by the USPTO dated Jun. 29, 2016, for U.S. Appl. No. 13/003,570, filed Apr. 26, 2011 and published as US 2011/0293650 on Dec. 1, 2011 (1st Named Inventor—D'Aoust; Applicant—Medicago, Inc.) (18 pages).
Notice of Allowance issued by the USPTO dated May 26, 2016, for U.S. Appl. No. 13/748,531, filed Jan. 23, 2013 and published as US 2013/0142826 on Jun. 6, 2013 (1st Named Inventor—D'Aoust; Applicant—Medicago, Inc.) (27 pages).
Notice of Allowance issued by the USPTO dated May 31, 2016, for U.S. Appl. No. 13/734,886, filed Jan. 23, 2013 and published as US 2013/0183341 on Jul. 18, 2013 (1st Named Inventor—D'aoust; Applicant—Medicago, Inc.) (5 pages).
Notice of Ground for Refusal dated Sep. 29, 2016 by the Korean Intellectual Property Office for Application No. KR 10-2012-7009357 (Inventor—Vezina // Applicant—Medicago Inc.) (8 pages).
Notice of Grounds for Refusal dated Jun. 2, 2016, by the Korean Intellectual Property Office for Application No. 10-2010-7018343 (Inventor—D'Aoust // Applicant—Medicago Inc.) (18 pages).
Notification of Re-Examination dated May 26, 2016 by the State Intellectual Property Office of the People's Republic of China for application CN 201080042333.0 (Applicant—Medicago, Inc.) (4 pages—English Translation).
Notification of Re-Examination dated Sep. 20, 2016, by the State Intellectual Property Office of the People's Republic of China for application CN 201080042336.4 (Applicant—Medicago, Inc.) (11 pages—English Translation).
Office Action issued by the Egyptian Patent Office dated May 18, 2016, for Egyptian Application No. PCT/ 61/2010 (4 pages).
Office Action issued by the IP Office of the Philippines Bureau of Patents dated Jun. 28, 2016, for application 1-2012-500566 (Applicant—Medicago, Inc.) (4 pages).
Office Action dated Jul. 27, 2016 by the Registrar of Patents of Israel for Israeli application IL 218393 (Applicant—Medicago, Inc.) (4 pages—English Translation).
Office Action dated May 23, 2016, by the Registrar of Patents of Israel for Israeli application IL 218422 (Applicant—Medicago, Inc.) (2 pages—English Translation).
Office Action dated Mar. 31, 2016 by the Intellectual Property Corporation of Malaysia for Malaysian app PI2012001251 (Applicant—Medicago, Inc.) (3 pages).
Office Action dated Oct. 4, 2016, by th Canadian IP Office for application CA 2,772,964 (applicant—Medicago, Inc.) (4 pages).
Office Action dated Jul. 27, 2016 by the European Patent Office for EP patent application No. 10818190.0, filed on Sep. 21, 2010 (Applicant—Medicago, Inc. // Inventor—Vezina et al.) (5 pages).
Summary of Office Action issued by the IP Office of the Philippines Bureau of Patents dated Jun. 10, 2016 for application 1-2012-500565 (Applicant—Medicago, Inc.) (3 pages).
Summary of Office Action dated Jul. 25, 2016, for Indonesian Patent Application No. W-00201000109 (1 page).
Written Opinion dated May 17, 2016, by the IP Office of Singapore for application SG201201471-8, filed on Sep. 21, 2010 (Applicant—Medicago, Inc.) (11 pages).
Anonymous, Protoplast Preparation (from Plant Tissue). Dec. 1, 2006 (Jan. 12, 2006), Retrieved from internet URL: http://ivaan.com/protocls/128.html.
Attwood, T.K., Genomics. The Babel of Bioinformatics. Science. 2000; 290(5491):471-3.
Baker, D. and Sali, A., Protein Structure Prediction and Structural Genomics. Science. 2001; 294(5540):93-6 (24 pages).
Klopfleisch, R. et al., Neurotropism of Highly Pathogenic Avian Influenza Virus A/Chicken/Indonesia/2003 (H5N1) in Experimentally Infected Pigeons (*Columbia livia* f. *domestica*). Vet Pathol. 2006; 43(4):463-70.

(56) References Cited

OTHER PUBLICATIONS

Park, K.-H., Microbial Production of Yeast and Plant Cell Wall Lytic Enzyme. Research Report from the University of Seoul. 1988; pp. 1-64 (English-language Translation of Summary Only).
Valat, L. et al., Transgenic Grapevine Rootstock Clones Expressing the Coat Protein or Movement Protein Genes of *Grapevine fanleaf virus*: Characterization and Reaction to Virus Infection Upon Protoplast Electroporation. Plant Sci. 2006; 170:739-47.
Whitelam, G.C., The Production of Recombinant Proteins in Plants. J Sci Food Agri. 1995; 68(1):1-9.
Office Action dated Oct. 13, 2017 by the Canadian Patent Office for Patent Application No. 2,772,964, which was filed on Mar. 2, 2012 (Inventor—Vezina et al.; Applicant—Medicago, Inc.) (5 pages).
Office Action dated Nov. 13, 2017 by the Intellectual Property Office of India for Patent Application No. 2637/DELNP/2012, which was filed on Mar. 26, 2012 (Inventor—Vezina et al.; Applicant—Medicago, Inc.) (8 pages).
Notice of Allowance dated Aug. 1, 2017 by the Intellectual Property Office of the Philippines for Patent Application No. 1/2012/500565, which was filed on Mar. 20, 2012 (Inventor—Vezina et al.; Applicant—Medicago, Inc.) (1 page).
Non-Final Office Action dated Oct. 5, 2017 by the U.S. Patent and Trademark Office for U.S. Appl. No. 13/497,757, filed Mar. 22, 2012 and published as US 2012/0178149 on Jul. 12, 2012 (Inventor—Vezina et al.; Applicant—Medicago, Inc.;) (15 pages).
Non-Final Office Action dated Dec. 13, 2017 by the U.S. Patent and Trademark Office for U.S. Appl. No. 15/256,119, filed Sep. 2, 2016 and published as US 2017/0088848 on Mar. 30, 2017 (Inventor—D'Aoust et al.; Applicant—Medicago, Inc.) (11 pages).
Examination Report dated Nov. 10, 2016 by the Intellectual Property Office of Singapore for SG Application No. 201201471-8, which was filed on Sep. 21, 2010(Applicant—Medicago, Inc.) (11 pages).
Examination Report dated Oct. 28, 2016 by the Korean Intellectual Property Office for KR Application No. UAE/P/ 0287/2012 which was filed on Mar. 21, 2012 (Applicant—Medicago) (6 pages).
Examination Report dated Oct. 28, 2016 by the Korean Intellectual Property Office for KR Application No. UAE/P/ 0286/2012, which was filed on Mar. 21, 2012(Applicant—Medicago, Inc.) (9 pages).
Decision of Reexamination dated Dec. 21, 2016 by the State Intellectual Property Office of the People's Republic of China for CN Application No. 201080042333.0, which was filed on Sep. 31, 2010 and published as 102549148A on Jul. 4, 2012 (Applicant—Medicago Inc.) (1 page).
Communication under Rule 71(3) EPC dated Apr. 10, 2017 by the European Patent Office for EP Application No. EP 10818191.8, which was filed on Sep. 21, 2010 and published as EP 2480560 A1 on Aug. 1, 2012 (Applicant—Medicago Inc.) (5 pages).
Notice of Grounds for Refusal dated Mar. 15, 2017 by the Korean Patent Office for KR Application No. KR 20127010044, which was filed on Sep. 21, 2010 and published as KR 20120093223 A on Aug. 22, 2012 (Applicant—Medicago Inc.) (Original—5 pages // Translation—8 pages).
Communication under Rule 71(3) EPC dated Apr. 6, 2017 by the European Patent Office for EP Application No. EP10818190.0, which was filed on Sep. 21, 2010 and published as EP 2480658 A1 on Aug. 1, 2012 (Applicant—Medicago Inc.) (5 pages).
Decision to Grant a European patent pursuant to Article 97(1) EPC dated Aug. 10, 2017 by the European Patent Office for EP Application No. EP10818190.0, which was filed on Sep. 21, 2010 and published as EP 2480658 A1 on Aug. 1, 2012 (Applicant—Medicago Inc.) (5 pages).
Examination Report dated Oct. 28, 2016 by the Korean Patent Office for KR Application No. UAE/P/0043/2010, which was filed on Jan. 13, 2010 (Applicant—Medicago Inc.) (7 pages).
Sixth Office Action dated Mar. 28, 2017 by the SIPO for CN Application No. 201310021693, which was filed on Jan. 12, 2009 and published as CN 103122354 A on May 29, 2013 (Applicant—Medicago Inc.) (Original—5 pages // Translation—5 pages).

Notification of Reasons for Refusal dated Dec. 26, 2016 by the Japanese Patent Office for JP Application No. 2016000233, which was filed on Jan. 4, 2016 and published as JP 2016052331 A on Apr. 14, 2016 (Applicant—Medicago Inc.) (Original—5 pages // Translation—3 pages).
Non Final Rejection dated Apr. 6, 2017 by the USPTO for U.S. Appl. No. 15/256,119, filed Sep. 2, 2016 and published as US 2017-0088848 A1 on Mar. 30, 2017 (Applicant—Medicago Inc.; Inventor—Marc-Andre D'Aoust) (8 pages).
Riazunnisa, K. et al., Preparation of *Arabidopsis mesophyll* Protoplasts with High Rates of Photosynthesis. Physiol Plant. 2007; 129(4):879-86.
Siminis, C.I. et al., Catalase is Differentially Expressed in Dividing and Nondividing Protoplasts. Plant Physiol. 1994; 105:1375-83.
Office Action dated Oct. 13, 2017 by the Eurasian Intellectual Property Office for Patent Application No. 201001198 (Inventor—Vezina et al.; Applicant—Medicago, Inc.) (Translation Only—2 pages).
Office Action dated Nov. 14, 2017 by the Intellectual Property Office of Egypt for Patent Application PCT 61/2010 (Inventor—Vezina et al.; Applicant—Medicago, Inc.) (Translation Summary Only—1 page).
Office Action dated Jan. 18, 2018 by the Intellectual Property Office of India for Patent Application No. 2591/DELNP/2012 (Inventor—Vezina et al.; Applicant—Medicago, Inc.) (6 pages).
Decision of Final Rejection dated Jan. 26, 2018 by the Korean Intellectual Property Office for Patent Application No. 10-2012-7010044 (Inventor—Vezina et al.; Applicant—Medicago, Inc.) (Translation Only—7 pages).
Decision of Final Rejection dated Jan. 30, 2018 by the Korean Intellectual Property Office for Patent Application No. 10-2016-7010959 (Inventor—Vezina et al.; Applicant—Medicago, Inc.) (Translation Only—6 pages).
Notice of Allowance dated Feb. 28, 2018 by the Intellectual Property Office of the Philippines for Patent Application No. 1/2012/500566, which was filed on Mar. 20, 2012 (Inventor—Vezina et al.; Applicant—Medicago, Inc.) (1 page).
Examination Report dated Mar. 16, 2018 by the Korean Intellectual Property Office for Patent Application No. UAE/P/0768/2010 (Inventor—Vezina et al.; Applicant—Medicago, Inc.) (10 pages).
Notice of Grounds for Preliminary Rejection dated Apr. 5, 2018 by the Korean Intellectual Property Office for Patent Application No. 10-2018-7005775, which was filed on Feb. 27, 2018 (Inventor—Vezina et al.; Applicant—Medicago, Inc.) (Translation Only—8 pages).
Final Office Action dated Jun. 15, 2018 by the U.S. Patent and Trademark Office for U.S. Appl. No. 13/497,757, filed Mar. 22, 2012 and published as US 2012/0178149 on Jul. 12, 2012 (Inventor—Vezina et al.; Applicant—Medicago, Inc.;) (15 pages).
Abtahi, S. and Aminlari, M., Effect of Sodium Sulfite, Sodium Bisulfite, Cysteine, and pH on Protein Solubility and Sodium Dodecyl Sulfate—Polyacrylamide Gel Electrophoresis of Soybean Milk Base. J Agric Food Chem. 1997; 45:4768-72.
Facchini, P.J. et al., Decreased Cell Wall Digestibility in Canola Transformed with Chimeric Tyrosine Decarboxylase Genes from Opium Poppy. Plant Physiol. 1999; 120:653-63.
Non-Final Office Action dated Jan. 11, 2019 by the U.S. Patent and Trademark Office for U.S. Appl. No. 13/497,757, filed Mar. 22, 2012 and published as US 2012/0178149 on Jul. 12, 2012 (Inventor—Vezina et al.; Applicant—Medicago, Inc.;) (22 pages).
Final Office Action dated Aug. 22, 2019 by the U.S. Patent and Trademark Office for U.S. Appl. No. 13/497,757, filed Mar. 22, 2012 and published as US 2012/0178149 A1 on Jul. 12, 2012 (Inventor—Louis-Philippe Vezina) (18 pages).
Asenjo, J.A., et al. Selective Release of Recombinant Protein Particles (VLPs) from Yeast Using a Pure Lytic glucanase Enzyme. Nation Biotechnology, 1993, pp. 1-7.
Biemelt, et al., "Production of Human Papillomavirus Type 16 Virus-Like particles in Transgenic Plants", J. of Virology, Sep. 2003, pp. 9211-9220.
Ellis, "The molecular chaperone concept", Seminars in Cell Biology, 1990 (1):1-9 (abstract only).

(56) References Cited

OTHER PUBLICATIONS

"Novel Swine-Origin Influenza A (H1N1) Virus Investigation Team. Emergence of a Novel Swine-Origin Influenza A (H1N1) Virus in Humans", The New England Journal of Medicine, 2009, vol. 360:25. pp 2605-2615.
Power, et al., "A Simple Method for the Isolation of Very Large Numbers of Leaf Protoplasts by using Mixtures of Cellulase and Pectinase", Biochem J., 111(5), 1969, p. 33P.
Sorensen, "Advanced genetic strategies for recombinant protein expression in *Escherichia coli*", Journal of Biotechnology 115 (2005) pp. 113-128.
Takahashi, et al., "A high-throughput screen of cell-death-inducing factors in Nitotiana benthamiana identifies a novel MAPKK that mediates INF1-induced cell death signaling and non-host resistance to Pseudomonas cichorii", The Plant Journal (2007) 49, pp. 1030-1040.
Wang, et al., "Role of plant heat-shock proteins and molecular chaperones in the abiotic stress response" Trends in Plant Science, vol. 9:5, 2004, pp. 244-252.
Webby, et al., "Purification of the NY-RMV and NY-SGV Isolates of Varley Yellow Dwarf Virus and the Production and Properties of their Antibodies", Plant Disease, Nov. 1992 pp. 1125-1132.
Wickramasinghe, et al., "Tangential Flow Microfiltration and Ultrafiltration for Human Influenza A Virus Concentration and Purification", Biotechnology and Bioengineering, vol. 92:2, Oct. 20, 2005, pp. 199-208.
Yigzaw, et al., "Exploitation of the Adsorptive Properties of Depth Filters for Host Cell Protein Removal during Monoclonal Antibody Purification", Biotechnol. Prog. 2006, vol. 22, pp. 288-296.
Yokoyama, et al., "Co-expression of human chaperone Hsp70 and Hsdj or Hsp40 co-factor increases solubility of overexpressed target proteins in insect cells", Biochimica et Biophysica Acta 1493 (2000) pp. 119-124.
Notice of Acceptance issued by the Australian Intellectual Property Office dated Dec. 17, 2014 for application 2010300033, filed on Dec. 10, 2014 (Applicant—Medicago, Inc. // Inventor—Vezina, et al.) (3 pages).
Exam Report issued by the Australian Intellectual Property Office dated Dec. 24, 2014 for application 2010300034 (Applicant—Medicago, Inc. // Inventor—Vezina, et al.) (4 pages).
Notice of Allowance issued by the Canadian Intellectual Property Office dated Jun. 1, 2015 for CA 2,730,185, filed on Jul. 2, 2009 (Applicant—Medicago, Inc. // Inventor—Vezina, et al.) (1 page).
Third Office Action dated May 26, 2015 by the State Intellectual Property Office of the People's Republic of China for application CN 201310021693.8 (Applicant—Medicago, Inc.
Office Action dated Nov. 15, 2014 by the State Intellectual Property Office of the People's Republic of China for application CN 201080042336.4 (Applicant—Medicago, Inc. . (11 pages—English Translation).
Decision on Rejection dated May 28, 2015 by the State Intellectual Property Office of the People's Republic of China for application CN 201080042336.4 (Applicant—Medicago, Inc. . (7 pages—English Translation).
Office Action dated Sep. 23, 2014 by the State Intellectual Property Office of the People's Republic of China for application CN 201310021693.8 (Applicant—Medicago, Inc. (16 pages—English Translation).
Office Action dated Sep. 3, 2014 ny the Eurasian IP Office for application EA 201001198 (2 pages—English Translation).
Office Action dated Sep. 3, 2014 by the Egyptian Patent Office for EG patent application No. PCT 122212010 filed on 01/12109 (Applicant—Medicago, Inc. // Inventor—D'Aoust, et al.) (15 pages).
Office Action dated Oct. 6, 2014 by the European Patent Office for EP patent application No. 10818190.0, filed on Sep. 21, 2010 (Applicant—Medicago, Inc. // Inventor—Vezina et al.) (5 pages).
Office Action dated Sep. 20, 2015 by the European Patent Office for EP patent application No. 10818190.0, filed on Sep. 21, 2010 (Applicant—Medicago, Inc. // Inventor—Vezina et al.) ( 5 pages).
Office Action dated Sep. 22, 2014 by the Indonesian Patent Office for ID application No. ID W-0020102481, filed Jul. 11, 2008 (Applicant—Medicago, Inc. // Inventor—D'Aoust, et al.) (3 Pages—English Summary and Indonesian Original).
Office Action dated Jan. 9, 2015 by the Indonesian Patent Office for ID application No. ID W-0020102481, filed Jul. 11, 2008 (Applicant—Medicago, Inc. // Inventor—D'Aoust, et al.) (5 Pages—English Summary and Indonesian Original).
Certificate of Grant dated May 27, 2015 by the Registrar of Patents of Israel for IL patent application 203018 filed on 01/12109 (Medicago, Inc. II D'Aoust et al.) (2 pages).
Office Action dated Jan. 13, 2015 by the Patent Office of Japan for application JP 2011-516934 (Applicant—Medicago, Inc.) (10 pages—English Translation).
Office Action dated Sep. 28, 2015 by the Registrar of Patents of Israel for Israeli application IL 218393 (Applicant—Medicago, Inc.) (2 pages—English Translation).
Office Action dated Oct. 21, 2014 by the Registrar of Patents of Israel for Israeli application IL 218422 (Applicant—Medicago, Inc.) (2 pages—English Translation).
Exam Report dated Aug. 6, 2015 by the Patent Office of India for application 212/DELNP/2010, filed on Jan. 12, 2010 (Applicant—Medicago, Inc.) (2 pages).
Office Action dated May 27, 2015 by the Patent Office of Japan for application JP 2014-039035 (Applicant—Medicago, Inc.) (7 pages—English Translation).
Office Action dated Dec. 22, 2014 by the Korean Intellectual Property Office for Application No. 10-2010-7002538 (Inventor—D'Aoust // Applicant—Medicago Inc.) (7 pages—Korean Original and English Translation).
Decision to Grant dated Jul. 20, 2015 by the Korean Intellectual Property Office for Application No. 10-2010-7002538 (Inventor—D'Aoust // Applicant—Medicago Inc.) (4 pages—Korean Original and English Translation).
Notice of Grounds for Refusal dated May 21, 2015 by the Korean Intellectual Property Office for Application No. 10-2010-7018343 (Inventor—D'Aoust // Applicant—Medicago Inc.) (30 pages—Korean Original and English Translation).
Office Action dated Sep. 15, 2014 by the Intellectual Property Corporation of Malaysia for Malaysian app PI2010000142, filed Jul. 11, 2008 (Applicant—Medicago, Inc.) (3 pages).
Office Action dated Feb. 16, 2015 by the Mexican Patent Office for patent application No. MX/a/2012/003373 (Applicant—Medicago, Inc. // Inventor—D'Aoust, et al.) ( 2 pages).
Office Action dated Sep. 29, 2015 by the Federal Service for Intellectual Property of the Russian Federation for application RU 2012115661 (8 pages—English Translation).
Office Action dated Jun. 24, 2015 by the Federal Service for Intellectual Property of the Russian Federation for application RU 2012115661 (2 pages—English Translation).
Office Action dated Nov. 12, 2014 by the Federal Service for Intellectual Property of the Russian Federation for application RU 012115996 (3 pages—Translation).
Notice of Allowance dated May 5, 2015 by the Federal Service for Intellectual Property of the Russian Federation for application RU 012115996 (9 pages—Translation).
Certificate of Grant dated Aug. 26, 2014 by the Registry of Patents of Singapore for application SG 187500, filed on Jan. 12, 2009 (Applicant—Medicago, Inc. // Inventor—D'Aoust, et al.) ( 2 pages).
Final Office Action issued by the USPTO dated Dec. 5, 2015 for U.S. Appl. No. 13/734,886, filed Jan. 23, 2013 and published as US 2013/0183341 on Jul. 18, 2013 (1st Named Inventor—D'Aoust; Applicant—Medicago, Inc.) (12 pages).
Final Office Action issued by the USPTO dated Jun. 25, 2015 for U.S. Appl. No. 13/734,886, filed Jan. 23, 2013 and published as US 2013/0183341 on Jul. 18, 2013 (1st Named Inventor—D'aoust; Applicant—Medicago, Inc.) (34 pages).
Non-Final Office Action issued by the USPTO dated Jan. 5, 2015 for U.S. Appl. No. 13/748,531, filed Jan. 23, 2013 and published as US 2013/0142826 on Jun. 6, 2013 (1st Named Inventor—D'Aoust; Applicant—Medicago, Inc.) (21 pages).
Final Office Action issued by the USPTO dated Jun. 23, 2015 for U.S. Appl. No. 13/748,531, filed Jan. 23, 2013 and published as US

(56) References Cited

OTHER PUBLICATIONS

2013/0142826 on Jun. 6, 2013 (1st Named Inventor—D'aoust; Applicant—Medicago, Inc.) (12 pages).
Non-Final Office Action issued by the USPTO dated Feb. 11, 2015 for U.S. Appl. No. 13/003,570, filed Apr. 26, 2011 and published as US 2011/0293650 on Dec. 1, 2011 (1st Named Inventor—D'Aoust; Applicant—Medicago, Inc.) (30 pages).
Non-Final Office Action issued by the USPTO dated Aug. 28, 2014 for U.S. Appl. No. 13/497,757, filed Mar. 22, 2012 and published as US 2012/0178149 on Jul. 12, 2012 (1st Named Inventor—Vezina; Applicant—Medicago, Inc.) (60 pages).
Final Office Action issued by the USPTO dated Jun. 25, 2015 for U.S. Appl. No. 13/497,757, filed Mar. 22, 2012 and published as US 2012/0178149 on Jul. 12, 2012 (1st Named Inventor—Vezina; Applicant—Medicago, Inc.) (22 pages).
Non-Final Office Action dated Jun. 1, 2020 by the U.S. Patent and Trademark Office for U.S. Appl. No. 13/497,757, filed Mar. 22, 2012 and published as US 2012/0178149 A1 on Jul. 12, 2012 (Inventor—Louis-Philippe Vezina) (28 pages).
Waterhouse et al. "Purification of particles of subterranean clover red leaf virus using an industrial-grade cellulose." J. of Virological Methods. 1984, 8:321-329.

* cited by examiner

Figure 2A

TTAATTAAGAATTCGAGCTCCACCGCGGAAACCTCCTCGGATTCCATTGCCCAGCTATCTGTCACTTTA
TTGAGAAGATAGTGGAAAAGGAAGGTGGCTCCTACAAATGCCATCATTGCGATAAAGGAAAGGCCATC
GTTGAAGATGCCTCTGCCGACAGTGGTCCCAAAGATGGACCCCCACCCACGAGGAGCATCGTGGAAAA
AGAAGACGTTCCAACCACGTCTTCAAAGCAAGTGGATTGATGTGATATCTCCACTGACGTAAGGGATG
ACGCACAATCCCACTATCCTTCGCAAGACCCTTCCTCTATATAAGGAAGTTCATTTCATTTGGAGAGGT
ATTAAAATCTTAATAGGTTTTGATAAAAGCGAACGTGGGGAAACCCGAACCAAACCTTCTTCTAAACTC
TCTCTCATCTCTCTTAAAGCAAACTTCTCTCTTGTCTTTCTTGCGTGAGCGATCTTCAACGTTGTCAGAT
CGTGCTTCGGCACCAGTACAACGTTTTCTTTCACTGAAGCGAAATCAAAGATCTCTTTGTGGACACGTA
GTGCGGCGCCATTAAATAACGTGTACTTGTCCTATTCTTGTCGGTGTGGTCTTGGGAAAAGAAAGCTTG
CTGGAGGCTGCTGTTCAGCCCCATACATTACTTGTTACGATTCTGCTGACTTTCGGCGGGTGCAATATC
TCTACTTCTGCTTGACGAGGTATTGTTGCCTGTACTTCTTTCTTCTTCTTGCTGATTGGTTCTATAA
GAAATCTAGTATTTTCTTTGAAACAGAGTTTTCCCGTGGTTTTCGAACTTGGAGAAAGATTGTTAAGCT
TCTGTATATTCTGCCCAAATTTGTCGGGCCCATGGAGAAAATAGTGCTTCTTCTTGCAATAGTCAGTCT
TGTTAAAAGTGATCAGATTTGCATTGGTTACCATGCAAACAATTCAACAGAGCAGGTTGACACAATCA
TGGAAAAGAACGTTACTGTTACACATGCCCAAGACATACTGGAAAAGACACACAACGGGAAGCTCTGC
GATCTAGATGGAGTGAAGCCTCTAATTTTAAGAGATTGTAGTGTAGCTGGATGGCTCCTCGGGAACCC
AATGTGTGACGAATTCATCAATGTACCGGAATGGTCTTACATAGTGGAGAAGGCCAATCCAACCAATG
ACCTCTGTTACCCAGGGAGTTTCAACGACTATGAAGAACTGAAACACCTATTGAGCAGAATAAACCAT
TTTGAGAAAATTCAAATCATCCCCAAAAGTTCTTGGTCCGATCATGAAGCCTCATCAGGAGTTAGCTCA
GCATGTCCATACCTGGGAAGTCCCTCCTTTTTTAGAAATGTGGTATGGCTTATCAAAAAGAACAGTACA
TACCCAACAATAAAGAAAAGCTACAATAATACCAACCAAGAGGATCTTTTGGTACTGTGGGGAATTCA
CCATCCTAATGATGCGGCAGAGCAGACAAGGCTATATCAAAACCCAACCACCTATATTTCCATTGGGA
CATCAACACTAAACCAGAGATTGGTACCAAAAATAGCTACTAGATCCAAAGTAAACGGGCAAAGTGGA
AGGATGGAGTTCTTCTGGACAATTTTAAAACCTAATGATGCAATCAACTTCGAGAGTAATGGAAATTTC
ATTGCTCCAGAATATGCATACAAAATTGTCAAGAAAGGGGACTCAGCAATTATGAAAAGTGAATTGGA
ATATGGTAACTGCAACACCAAGTGTCAAACTCCAATGGGGGCGATAAACTCTAGTATGCCATTCCACA
ACATACACCCTCTCACCATCGGGGAATGCCCCAAATATGTGAAATCAAACAGATTAGTCCTTGCAACA
GGGCTCAGAAATAGCCCTCAAAGAGAGAGCAGAAGAAAAAAGAGAGGACTATTTGGAGCTATAGCAG
GTTTTATAGAGGGAGGATGGCAGGGAATGGTAGATGGTTGGTATGGGTACCACCATAGCAATGAGCAG
GGGAGTGGGTACGCTGCAGACAAAGAATCCACTCAAAAGGCAATAGATGGAGTCACCAATAAGGTCA
ACTCAATCATTGACAAAATGAACACTCAGTTTGAGGCCGTTGGAAGGGAATTTAATAACTTAGAAAGG
AGAATAGAGAATTTAAACAAGAAGATGGAAGACGGGTTTCTAGATGTCTGGACTTATAATGCCGAACT
TCTGGTTCTCATGGAAAATGAGAGAACTCTAGACTTTCATGACTCAAATGTTAAGAACCTCTACGACAA
GGTCCGACTACAGCTTAGGGATAATGCAAAGGAGCTGGGTAACGGTTGTTTCGAGTTCTATCACAAAT
GTGATAATGAATGTATGGAAAGTATAAGAAACGGAACGTACAACTATCCGCAGTATTCAGAAGAAGCA
AGATTAAAAAGAGAGGAAATAAGTGGGGTAAAATTGGAATCAATAGGAACTTACCAAATACTGTCAAT
TTATTCAACAGTGGCGAGTTCCCTAGCACTGGCAATCATGATGGCTGGTCTATCTTTATGGATGTGCTC
CAATGGATCGTTACAATGCAGAATTTGCATTTAAAGGCCTATTTTCTTTAGTTTGAATTTACTGTTATTC
GGTGTGCATTTCTATGTTTGGTGAGCGGTTTTCTGTGCTCAGAGTGTGTTTATTTTATGTAATTTAATTT
CTTTGTGAGCTCCTGTTTAGCAGGTCGTCCCTTCAGCAAGGACACAAAAAGATTTTAATTTTATTAAAA
AAAAAAAAAAAAAGACCGGGAATTCGATATCAAGCTTATCGACCTGCAGATCGTTCAAACATTTGGC
AATAAAGTTTCTTAAGATTGAATCCTGTTGCCGGTCTTGCGATGATTATCATATAATTTCTGTTGAATT
ACGTTAAGCATGTAATAATTAACATGTAATGCATGACGTTATTTATGAGATGGGTTTTTATGATTAGAG
TCCCGCAATTATACATTTAATACGCGATAGAAAACAAAATATAGCGCGCAAACTAGGATAAATTATCG
CGCGCGGTGTCATCTATGTTACTAGATTCTAGAGTCTCAAGCTTGGCGCGCC

Figure 2B

MEKIVLLLAIVSLVKSDQICIGYHANNSTEQVDTIMEKNVTVTHAQDILEKTHNGKLCDLDGVKPLILRDCS
VAGWLLGNPMCDEFINVPEWSYIVEKANPTNDLCYPGSFNDYEELKHLLSRINHFEKIQIIPKSSWSDHEASS
GVSSACPYLGSPSFFRNVVWLIKKNSTYPTIKKSYNNTNQEDLLVLWGIHHPNDAAEQTRLYQNPTTYISIG
TSTLNQRLVPKIATRSKVNGQSGRMEFFWTILKPNDAINFESNGNFIAPEYAYKIVKKGDSAIMKSELEYGN
CNTKCQTPMGAINSSMPFHNIHPLTIGECPKYVKSNRLVLATGLRNSPQRESRRKKRGLFGAIAGFIEGGWQ
GMVDGWYGYHHSNEQGSGYAADKESTQKAIDGVTNKVNSIIDKMNTQFEAVGREFNNLERRIENLNKKM
EDGFLDVWTYNAELLVLMENERTLDFHDSNVKNLYDKVRLQLRDNAKELGNGCFEFYHKCDNECMESIR
NGTYNYPQYSEEARLKREEISGVKLESIGTYQILSIYSTVASSLALAIMMAGLSLWMCSNGSLQCRICI

Figure 5

AGAGGTACCCCGGGCTGGTATATTTATATGTTGTCAAATAACTCAAAAACCATAAAAGTTTAAGTTAGC
AAGTGTGTACATTTTTACTTGAACAAAAATATTCACCTACTACTGTTATAAATCATTATTAAACATTAG
AGTAAAGAAATATGGATGATAAGAACAAGAGTAGTGATATTTTGACAACAATTTTGTTGCAACATTTG
AGAAAATTTTGTTGTTCTCTCTTTTCATTGGTCAAAAACAATAGAGAGAGAAAAAGGAAGAGGGAGAA
TAAAAACATAATGTGAGTATGAGAGAGAAAGTTGTACAAAAGTTGTACCAAAATAGTTGTACAAATAT
CATTGAGGAATTTGACAAAAGCTACACAAATAAGGGTTAATTGCTGTAAATAAATAAGGATGACGCAT
TAGAGAGATGTACCATTAGAGAATTTTTGGCAAGTCATTAAAAAGAAAGAATAAATTATTTTTAAAAT
TAAAAGTTGAGTCATTTGATTAAACATGTGATTATTTAATGAATTGATGAAAGAGTTGGATTAAAGTTG
TATTAGTAATTAGAATTTGGTGTCAAATTTAATTTGACATTTGATCTTTTCCTATATATTGCCCCATAGA
GTCAGTTAACTCATTTTTATATTTCATAGATCAAATAAGAGAAATAACGGTATATTAATCCCTCCAAAA
AAAAAAAACGGTATATTTACTAAAAAATCTAAGCCACGTAGGAGGATAACAGGATCCCCGTAGGAGGA
TAACATCCAATCCAACCAATCACAACAATCCTGATGAGATAACCCACTTTAAGCCCACGCATCTGTGGC
ACATCTACATTATCTAAATCACACATTCTTCCACACATCTGAGCCACACAAAAACCAATCCACATCTTT
ATCACCCATTCTATAAAAAATCACACTTTGTGAGTCTACACTTTGATTCCCTTCAAACACATACAAAGA
GAAGAGACTAATTAATTAATTAATCATCTTGAGAGAAAATGGAGAAAATAGTGCTTCTTCTTGCAATA
GTCAGTCTTGTTAAAAGTGATCAGATTTGCATTGGTTACCATGCAAACAATTCAACAGAGCAGGTTGAC
ACAATCATGGAAAAGAACGTTACTGTTACACATGCCCAAGACATACTGGAAAAGACACACAACGGGAA
GCTCTGCGATCTAGATGGAGTGAAGCCTCTAATTTTAAGAGATTGTAGTGTAGCTGGATGGCTCCTCGG
GAACCCAATGTGTGACGAATTCATCAATGTACCGGAATGGTCTTACATAGTGGAGAAGGCCAATCCAA
CCAATGACCTCTGTTACCCAGGGAGTTTCAACGACTATGAAGAACTGAAACACCTATTGAGCAGAATA
AACCATTTTGAGAAAATTCAAATCATCCCCAAAAGTTCTTGGTCCGATCATGAAGCCTCATCAGGAGTT
AGCTCAGCATGTCCATACCTGGGAAGTCCCTCCTTTTTAGAAATGTGGTATGGCTTATCAAAAGAAC
AGTACATACCCAACAATAAAGAAAAGCTACAATAATACCAACCAAGAGGATCTTTTGGTACTGTGGGG
AATTCACCATCCTAATGATGCGGCAGAGCAGACAAGGCTATATCAAAACCCAACCACCTATATTTCCAT
TGGGACATCAACACTAAACCAGAGATTGGTACCAAAAATAGCTACTAGATCCAAAGTAAACGGGCAAA
GTGGAAGGATGGAGTTCTTCTGGACAATTTTAAAACCTAATGATGCAATCAACTTCGAGAGTAATGGA
AATTTCATTGCTCCAGAATATGCATACAAAATTGTCAAGAAGGGGACTCAGCAATTATGAAAAGTGA
ATTGGAATATGGTAACTGCAACACCAAGTGTCAAACTCCAATGGGGGCGATAAACTCTAGTATGCCAT
TCCACAACATACACC TCTCACCATCGGGGAATGCCCCAAATATGTGAAATCAAACAGATTAGTCCTTG
CAACAGGGCTCAGAAATAGCCCTCAAAGAGAGAGCAGAAGAAAAAGAGAGGACTATTTGGAGCTAT
AGCAGGTTTTATAGAGGGAGGATGGCAGGGAATGGTAGATGGTTGGTATGGGTACCACCATAGCAATG
AGCAGGGGAGTGGGTACGCTGCAGACAAAGAATCCACTCAAAAGGCAATAGATGGAGTCACCAATAA
GGTCAACTCAATCATTGACAAAATGAACACTCAGTTTGAGGCCGTTGGAAGGGAATTTAATAACTTAG
AAAGGAGAATAGAGAATTTAAACAAGAAGATGGAAGACGGGTTTCTAGATGTCTGGACTTATAATGCC
GAACTTCTGGTTCTCATGGAAAATGAGAGAACTCTAGACTTTCATGACTCAAATGTTAAGAACCTCTAC
GACAAGGTCCGACTACAGCTTAGGGATAATGCAAAGGAGCTGGGTAACGGTTGTTTCGAGTTCTATCA
CAAATGTGATAATGAATGTATGGAAAGTATAAGAAACGGAACGTACAACTATCCGCAGTATTCAGAAG
AAGCAAGATTAAAAAGAGAGGAAATAAGTGGGGTAAAATTGGAATCAATAGGAACTTACCAAATACT
GTCAATTTATTCAACAGTGGCGAGTTCCCTAGCACTGGCAATCATGATGGCTGGTCTATCTTTATGGAT
GTGCTCCAATGGATCGTTACAATGCAGAATTTGCATTTAAGAGCTCTAAGTTAAAATGCTTCTTCGTCT
CCTATTTATAATATGGTTTGTTATTGTTAATTTTGTTCTTGTAGAAGAGCTTAATTAATCGTTGTTGTTA
TGAAATACTATTTGTATGAGATGAACTGGTGTAATGTAATTCATTTACATAAGTGGAGTCAGAATCAG
AATGTTTCCTCCATAACTAACTAGACATGAAGACCTGCCGCGTACAATTGTCTTATATTTGAACAACTA
AAATTGAACATCTTTTGCCACAACTTTATAAGTGGTTAATATAGCTCAAATATATGGTCAAGTTCAATA
GATTAATAATGGAAATATCAGTTATCGAAATTCATTAACAATCAACTTAACGTTATTAACTACTAATTT
TATATCATCCCCTTTGATAAATGATAGTACA

```
CACTTTGTGAGTCTACACTTTGATTCCCTTCAAACACATACAAAGAGAAGAGACT
AATTAATTAATTAATCATCTTGAGAGAAAATGGATTTTCAGGTGCAGATTATCAG
CTTCCTGCTAATCAGTGCTTCAGTCATAATGTCCAGAGGACAAATTGTTCTCTCC
CAGTCTCCAGCAATCCTGTCTGCATCTCCAGGGGAGAAGGTCACAATGACTTGCA
GGGCCAGCTCAAGTGTAAGTTACATCCACTGGTTCCAGCAGAAGCCAGGATCCTC
CCCCAAACCCTGGATTTATGCCACATCCAACCTGGCTTCTGGAGTCCCTGTTCGC
TTCAGTGGCAGTGGGTCTGGGACTTCTTACTCTCTCACAATCAGCAGAGTGGAGG
CTGAAGATGCTGCCACTTATTACTGCCAGCAGTGGACTAGTAACCCACCCACGTT
CGGAGGGGGGACCAAGCTGGAAATCAAACGTACGGTGGCTGCACCATCTGTCTTC
ATCTTCCCGCCATCTGATGAGCAGTTGAAATCTGGAACTGCCTCTGTTGTGTGCC
TGCTGAATAACTTCTATCCCAGAGAGGCCAAAGTACAGTGGAAGGTGGATAACGC
CCTCCAATCGGGTAACTCCCAGGAGAGTGTCACAGAGCAGGACAGCAAGGACAGC
ACCTACAGCCTCAGCAGCACCCTGACGCTGAGCAAAGCAGACTACGAGAAACACA
AAGTCTACGCCTGCGAAGTCACCCATCAGGGCCTGAGCTCGCCCGTCACAAAGAG
CTTCAACAGGGGAGAGTGTTGAGACGTCGTTAAAATGCTTCTTCGTCTCCTATTT
ATAATATGGTTTGTTATTGTTAATTTTGTTCTTGTAGAAGAGCTTAATTAATCGT
TGTTGTTATGAAATACTATTTGTATGAGATGAACTGGTGTAATGTAATTCATTTA
CATAAGTGGAGTCAGAATCAGAATGTTTCCTCCATAACTAACTAGACATGAAGAC
CTGCCGCGTACAATTGTCTTATATTTGAACAACTAAAATTGAACATCTTTTGCCA
CAACTTTATAAGTGGTTAATATAGCTCAAATATATGGTCAAGTTCAATAGATTAA
TAATGGAAATATCAGTTATCGAAATTCATTAACAATCAACTTAACGTTATTAACT
ACTAATTTTATATCATCCCCTTTGATAAATGATAGTACACCAATTAGGAAGGAGA
ATTC
```

590 (LC fragment; SEQ ID NO.15).

Figure 9

```
CACTTTGTGAGTCTACACTTTGATTCCCTTCAAACACATACAAAGAGAAGAGACTAATTAATTAA
TTAATCATCTTGAGAGAAAATGGGTTGGAGCCTCATCTTGCTCTTCCTTGTCGCTGTTGCTACGC
GTGTCCTGTCCCAGGTACAACTGCAGCAGCCTGGGGCTGAGCTGGTGAAGCCTGGGGCCTCAGTG
AAGATGTCCTGCAAGGCTTCTGGCTACACATTTACCAGTTACAATATGCACTGGGTAAAACAGAC
ACCTGGTCGGGGCCTGGAATGGATTGGAGCTATTTATCCCGGAAATGGTGATACTTCCTACAATC
AGAAGTTCAAAGGCAAGGCCACATTGACTGCAGACAAATCCTCCAGCACAGCCTACATGCAGCTC
AGCAGCCTGACATCTGAGGACTCTGCGGTCTATTACTGTGCAAGATCGACTTACTACGGCGGTGA
CTGGTACTTCAATGTCTGGGGCGCAGGGACCACGGTCACCGTCTCTGCAGCTAGCACCAAGGGCC
CATCGGTCTTCCCCCTGGCACCCTCCTCCAAGAGCACCTCTGGGGGCACAGCGGCCCTGGGCTGC
CTGGTCAAGGACTACTTCCCCGAACCGGTGACGGTGTCGTGGAACTCAGGCGCCCTGACCAGCGG
CGTGCACACCTTCCCGGCTGTCCTACAGTCCTCAGGACTCTACTCCCTCAGCAGCGTGGTGACCG
TGCCCTCCAGCAGCTTGGGCACCCAGACCTACATCTGCAACGTGAATCACAAGCCCAGCAACACC
AAGGTGGACAAGAAAGTTGAGCCCAAATCTTGTGACAAAACTCACACATGCCCACCGTGCCCAGC
ACCTGAACTCCTGGGGGGACCGTCAGTCTTCCTCTTCCCCCCAAAACCCAAGGACACCCTCATGA
TCTCCCGGACCCCTGAGGTCACATGCGTGGTGGTGGACGTGAGCCACGAAGACCCTGAGGTCAAG
TTCAACTGGTACGTGGACGGCGTGGAGGTGCATAATGCCAAGACAAAGCCGCGGGAGGAGCAGTA
CAACAGCACGTACCGTGTGGTCAGCGTCCTCACCGTCCTGCACCAGGACTGGCTGAATGGCAAGG
AGTACAAGTGCAAGGTCTCCAACAAAGCCCTCCCAGCCCCCATCGAGAAAACCATCTCCAAAGCC
AAAGGGCAGCCTAGGGAACCACAAGTGTACACTCTTCCACCATCTAGGGATGAGCTTACTAAGAA
CCAAGTTTCTCTTACTTGTCTTGTGAAGGGATTTTATCCATCTGACATCGCCGTGGAATGGGAAT
CCAACGGACAACCAGAGAACAATTACAAGACTACTCCACCAGTTCTTGATTCTGATGGATCCTTC
TTTCTTTATTCCAAGCTTACTGTTGATAAGTCCAGATGGCAGCAAGGAAATGTGTTCTCTTGTTC
TGTTATGCACGAAGCTCTTCATAATCATTATACTCAAAAGTCCCTTTCTCTTTCTCCTGGAAAGT
GAGACGTCGTTAAAATGCTTCTTCGTCTCCTATTTATAATATGGTTTGTTATTGTTAATTTTGTT
CTTGTAGAAGAGCTTAATTAATCGTTGTTGTTATGAAATACTATTTGTATGAGATGAACTGGTGT
AATGTAATTCATTTACATAAGTGGAGTCAGAATCAGAATGTTTCCTCCATAACTAACTAGACATG
AAGACCTGCCGCGTACAATTGTCTTATATTTGAACAACTAAAATTGAACATCTTTTGCCACAACT
TTATAAGTGGTTAATATAGCTCAAATATATGGTCAAGTTCAATAGATTAATAATGGAAATATCAG
TTATCGAAATTCATTAACAATCAACTTAACGTTATTAACTACTAATTTTATATCATCCCCTTTGA
TAAATGATAGTACACCAATTAGGAAGGAGAATTC
```

592 (HC fragment; SEQ ID NO :16).

Figure 10

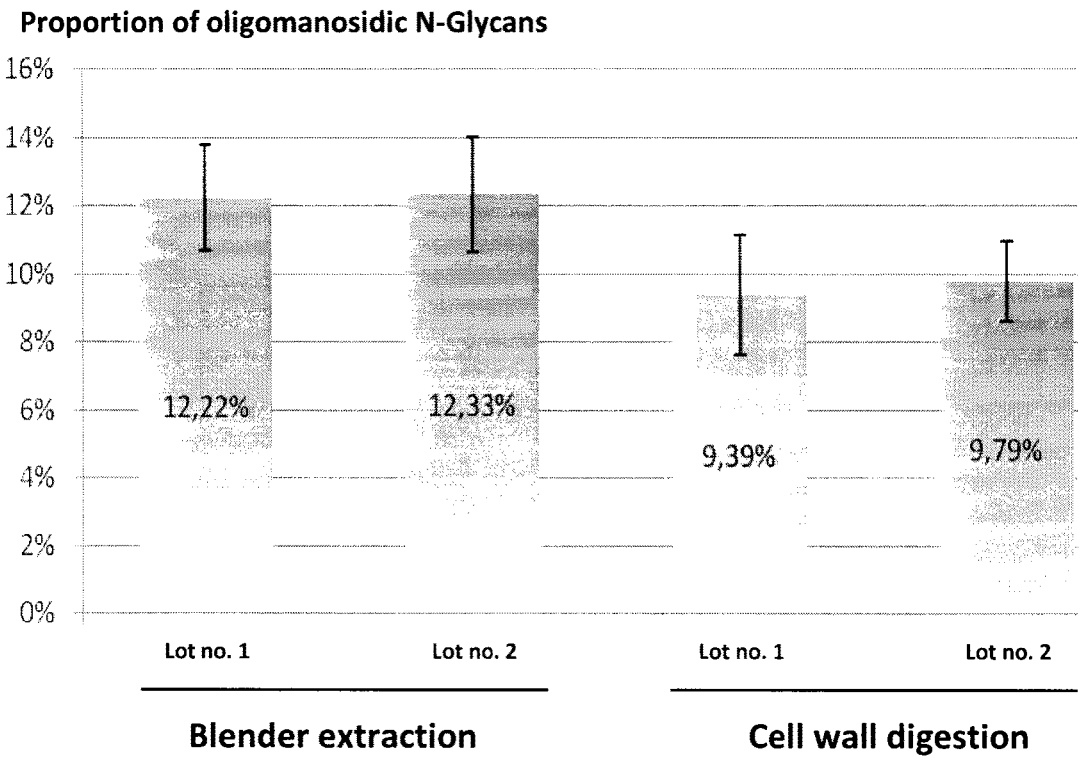

Statistical analysis

| p-value | Blender, Lot no. 1 | Digestion, Lot no. 1 | Blender, Lot no. 2 |
|---|---|---|---|
| Digestion, lot no. 1 | $3,3.10^{-4}$ (***) | | |
| Blender, Lot no. 2 | 1 (identical) | $1,9.10^{-4}$ (***) | |
| Digestion, lot no. 2 | $2,39.10^{-3}$ () | 1 (identical) | $1,41.10^{-3}$ () |

**: The difference in the proportion of oligomannosidic N-glycans is very significant (p-value between 0.01 and 0.1).
***: The difference in the proportion of oligomannosidic N-glycans is highly significant (p-value between 0 and 0.01).

Figure 13A

SEQUENCE LISTING

```
<160> NUMBER OF SEQ ID NOS: 16

<210> SEQ ID NO 1
<211> LENGTH: 3067
<212> TYPE: DNA
<213> ORGANISM: Artificial Sequence
<220> FEATURE:
<223> OTHER INFORMATION: Synthesized construct 685

<400> SEQUENCE: 1
ttaattaaga attcgagctc caccgcggaa acctcctcgg attccattgc ccagctatct      60
gtcactttat tgagaagata gtggaaaagg aaggtggctc ctacaaatgc catcattgcg     120
ataaaggaaa ggccatcgtt gaagatgcct ctgccgacag tggtcccaaa gatggacccc     180
cacccacgag gagcatcgtg gaaaagaag acgttccaac cacgtcttca aagcaagtgg     240
attgatgtga tatctccact gacgtaaggg atgacgcaca atcccactat ccttcgcaag     300
acccttcctc tatataagga agttcatttc atttggagag gtattaaaat cttaataggt     360
tttgataaaa gcgaacgtgg ggaaacccga accaaacctt cttctaaact ctctctcatc     420
tctcttaaag caaacttctc tcttgtcttt cttgcgtgag cgatcttcaa cgttgtcaga     480
```

```
tcgtgcttcg gcaccagtac aacgttttct ttcactgaag cgaaatcaaa gatctctttg    540
tggacacgta gtgcggcgcc attaaataac gtgtacttgt cctattcttg tcggtgtggt    600
cttgggaaaa gaaagcttgc tggaggctgc tgttcagccc catacattac ttgttacgat    660
tctgctgact ttcggcgggt gcaatatctc tacttctgct tgacgaggta ttgttgcctg    720
tacttctttc ttcttcttct tgctgattgg ttctataaga aatctagtat tttctttgaa    780
acagagtttt cccgtggttt tcgaacttgg agaaagattg ttaagcttct gtatattctg    840
cccaaatttg tcgggcccat ggagaaaata gtgcttcttc ttgcaatagt cagtcttgtt    900
aaaagtgatc agatttgcat tggttaccat gcaaacaatt caacagagca ggttgacaca    960
atcatggaaa agaacgttac tgttacacat gcccaagaca tactggaaaa gacacacaac    1020
gggaagctct gcgatctaga tggagtgaag cctctaattt taagagattg tagtgtagct    1080
ggatggctcc tcgggaaccc aatgtgtgac gaattcatca atgtaccgga atggtcttac    1140
atagtggaga aggccaatcc aaccaatgac ctctgttacc cagggagttt caacgactat    1200
gaagaactga acacctatt gagcagaata aaccattttg agaaaattca aatcatcccc    1260
aaaagttctt ggtccgatca tgaagcctca tcaggagtta gctcagcatg tccatacctg    1320
ggaagtccct cctttttag aaatgtggta tggcttatca aaaagaacag tacatacccca   1380 acaataaaga aaagctacaa taataccaac caagaggatc ttttggtact gtggggaatt    1440
caccatccta atgatgcggc agagcagaca aggctatatc aaaacccaac cacctatatt    1500
tccattggga catcaacact aaaccagaga ttggtaccaa aaatagctac tagatccaaa    1560
gtaaacgggc aaagtggaag gatggagttc ttctggacaa ttttaaaacc taatgatgca    1620
atcaacttcg agagtaatgg aaatttcatt gctccagaat atgcatacaa aattgtcaag    1680
aaaggggact cagcaattat gaaaagtgaa ttggaatatg gtaactgcaa caccaagtgt    1740
caaactccaa tggggcgat aaactctagt atgccattcc acaacataca ccctctcacc    1800 atcgggaat gccccaaata tgtgaaatca aacagattag tccttgcaac agggctcaga    1860
aatagccctc aaagagagag cagaagaaaa agagaggac tatttggagc tatagcaggt    1920
tttatagagg gaggatggca gggaatggta gatggttggt atgggtacca ccatagcaat    1980
gagcagggga gtgggtacgc tgcagacaaa gaatccactc aaaaggcaat agatggagtc    2040
accaataagg tcaactcaat cattgacaaa atgaacactc agtttgaggc cgttggaagg    2100
gaatttaata acttagaaag gagaatagag aatttaaaca agaagatgga agacgggttt    2160
ctagatgtct ggacttataa tgccgaactt ctggttctca tggaaaatga gagaactcta    2220
gactttcatg actcaaatgt taagaacctc tacgacaagg tccgactaca gcttagggat    2280
aatgcaaagg agctgggtaa cggttgtttc gagttctatc acaaatgtga taatgaatgt    2340
atggaaagta taagaaacgg aacgtacaac tatccgcagt attcagaaga agcaagatta    2400
aaaagagagg aaataagtgg ggtaaaattg gaatcaatag gaacttacca aatactgtca    2460
atttattcaa cagtggcgag ttccctagca ctggcaatca tgatggctgg tctatcttta    2520
tggatgtgct ccaatggatc gttacaatgc agaatttgca tttaaaggcc tattttcttt    2580
agtttgaatt tactgttatt cggtgtgcat ttctatgttt ggtgagcggt tttctgtgct    2640
cagagtgtgt ttattttatg taatttaatt tctttgtgag ctcctgttta gcaggtcgtc    2700
ccttcagcaa ggcacaaaaa agattttaat tttattaaaa aaaaaaaaaa aaagaccgg    2760 gaattcgata tcaagcttat cgacctgcag atcgttcaaa catttggcaa taaagtttct    2820
```

-continued

```
taagattgaa tcctgttgcc ggtcttgcga tgattatcat ataatttctg ttgaattacg    2880
ttaagcatgt aataattaac atgtaatgca tgacgttatt tatgagatgg gtttttatga    2940
ttagagtccc gcaattatac atttaatacg cgatagaaaa caaaatatag cgcgcaaact    3000
aggataaatt atcgcgcgcg gtgtcatcta tgttactaga ttctagagtc tcaagcttcg    3060
gcgcgcc                                                              3067
```

<210> SEQ ID NO 2
<211> LENGTH: 568
<212> TYPE: PRT
<213> ORGANISM: Artificial Sequence
<220> FEATURE:
<223> OTHER INFORMATION: Synthesized amino acid encoded by Seq Id No: 1

<400> SEQUENCE: 2

```
Met Glu Lys Ile Val Leu Leu Leu Ala Ile Val Ser Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45

Leu Glu Lys Thr His Asn Gly Lys Leu Cys Asp Leu Asp Gly Val Lys
    50                  55                  60

Pro Leu Ile Leu Arg Asp Cys Ser Val Ala Gly Trp Leu Leu Gly Asn
65                  70                  75                  80

Pro Met Cys Asp Glu Phe Ile Asn Val Pro Glu Trp Ser Tyr Ile Val
                85                  90                  95

Glu Lys Ala Asn Pro Thr Asn Asp Leu Cys Tyr Pro Gly Ser Phe Asn
            100                 105                 110

Asp Tyr Glu Glu Leu Lys His Leu Leu Ser Arg Ile Asn His Phe Glu
        115                 120                 125

Lys Ile Gln Ile Ile Pro Lys Ser Ser Trp Ser Asp His Glu Ala Ser
    130                 135                 140

Ser Gly Val Ser Ser Ala Cys Pro Tyr Leu Gly Ser Pro Ser Phe Phe
145                 150                 155                 160

Arg Asn Val Val Trp Leu Ile Lys Lys Asn Ser Thr Tyr Pro Thr Ile
                165                 170                 175

Lys Lys Ser Tyr Asn Asn Thr Asn Gln Glu Asp Leu Leu Val Leu Trp
            180                 185                 190

Gly Ile His His Pro Asn Asp Ala Ala Glu Gln Thr Arg Leu Tyr Gln
        195                 200                 205

Asn Pro Thr Thr Tyr Ile Ser Ile Gly Thr Ser Thr Leu Asn Gln Arg
    210                 215                 220

Leu Val Pro Lys Ile Ala Thr Arg Ser Lys Val Asn Gly Gln Ser Gly
225                 230                 235                 240

Arg Met Glu Phe Phe Trp Thr Ile Leu Lys Pro Asn Asp Ala Ile Asn
                245                 250                 255

Phe Glu Ser Asn Gly Asn Phe Ile Ala Pro Glu Tyr Ala Tyr Lys Ile
            260                 265                 270

Val Lys Lys Gly Asp Ser Ala Ile Met Lys Ser Glu Leu Glu Tyr Gly
        275                 280                 285

Asn Cys Asn Thr Lys Cys Gln Thr Pro Met Gly Ala Ile Asn Ser Ser
    290                 295                 300

Met Pro Phe His Asn Ile His Pro Leu Thr Ile Gly Glu Cys Pro Lys
305                 310                 315                 320
```

```
Tyr Val Lys Ser Asn Arg Leu Val Leu Ala Thr Gly Leu Arg Asn Ser
            325                 330                 335

Pro Gln Arg Glu Ser Arg Arg Lys Arg Gly Leu Phe Gly Ala Ile
            340                 345                 350

Ala Gly Phe Ile Glu Gly Gly Trp Gln Gly Met Val Asp Gly Trp Tyr
            355                 360                 365

Gly Tyr His His Ser Asn Glu Gln Gly Ser Gly Tyr Ala Ala Asp Lys
    370                 375                 380

Glu Ser Thr Gln Lys Ala Ile Asp Gly Val Thr Asn Lys Val Asn Ser
385                 390                 395                 400

Ile Ile Asp Lys Met Asn Thr Gln Phe Glu Ala Val Gly Arg Glu Phe
                405                 410                 415

Asn Asn Leu Glu Arg Arg Ile Glu Asn Leu Asn Lys Lys Met Glu Asp
            420                 425                 430

Gly Phe Leu Asp Val Trp Thr Tyr Asn Ala Glu Leu Leu Val Leu Met
            435                 440                 445

Glu Asn Glu Arg Thr Leu Asp Phe His Asp Ser Asn Val Lys Asn Leu
    450                 455                 460

Tyr Asp Lys Val Arg Leu Gln Leu Arg Asp Asn Ala Lys Glu Leu Gly
465                 470                 475                 480

Asn Gly Cys Phe Glu Phe Tyr His Lys Cys Asp Asn Glu Cys Met Glu
                485                 490                 495

Ser Ile Arg Asn Gly Thr Tyr Asn Tyr Pro Gln Tyr Ser Glu Glu Ala
            500                 505                 510

Arg Leu Lys Arg Glu Glu Ile Ser Gly Val Lys Leu Glu Ser Ile Gly
            515                 520                 525

Thr Tyr Gln Ile Leu Ser Ile Tyr Ser Thr Val Ala Ser Ser Leu Ala
    530                 535                 540

Leu Ala Ile Met Met Ala Gly Leu Ser Leu Trp Met Cys Ser Asn Gly
545                 550                 555                 560

Ser Leu Gln Cys Arg Ile Cys Ile
                565

<210> SEQ ID NO 3
<211> LENGTH: 24
<212> TYPE: DNA
<213> ORGANISM: Artificial Sequence
<220> FEATURE:
<223> OTHER INFORMATION: Synthesized oligonucleotide pBinPlus.2613c

<400> SEQUENCE: 3
aggaagggaa gaaagcgaaa ggag                                    24

<210> SEQ ID NO 4
<211> LENGTH: 56
<212> TYPE: DNA
<213> ORGANISM: Artificial Sequence
<220> FEATURE:
<223> OTHER INFORMATION: Synthesized oligonucleotide Mut-ATG115.r

<400> SEQUENCE: 4
gtgccgaagc acgatctgac aacgttgaag atcgctcacg caagaaagac aagaga   56

<210> SEQ ID NO 5
<211> LENGTH: 52
<212> TYPE: DNA
<213> ORGANISM: Artificial Sequence
<220> FEATURE:
```

<223> OTHER INFORMATION: Synthesized oligonucleotide Mut-ATG161.c

<400> SEQUENCE: 5
gttgtcagat cgtgcttcgg caccagtaca acgttttctt tcactgaagc ga    52

<210> SEQ ID NO 6
<211> LENGTH: 25
<212> TYPE: DNA
<213> ORGANISM: Artificial Sequence
<220> FEATURE:
<223> OTHER INFORMATION: Synthesized oligonucleotide LC-C5-1.110r

<400> SEQUENCE: 6
tctcctggag tcacagacag ggtgg    25

<210> SEQ ID NO 7
<211> LENGTH: 39
<212> TYPE: DNA
<213> ORGANISM: Artificial Sequence
<220> FEATURE:
<223> OTHER INFORMATION: Synthesized oligonucleotide ApaI-H5 (A-Indo).1c

<400> SEQUENCE: 7
tgtcgggccc atggagaaaa tagtgcttct tcttgcaat    39

<210> SEQ ID NO 8
<211> LENGTH: 37
<212> TYPE: DNA
<213> ORGANISM: Artificial Sequence
<220> FEATURE:
<223> OTHER INFORMATION: Synthesized oligonucleotide H5 (A-Indo)-
      StuI.1707r

<400> SEQUENCE: 8
aaataggcct ttaaatgcaa attctgcatt gtaacga    37

<210> SEQ ID NO 9
<211> LENGTH: 3111
<212> TYPE: DNA
<213> ORGANISM: Artificial Sequence
<220> FEATURE:
<223> OTHER INFORMATION: Synthesized oligonucleotide contruct 660

<400> SEQUENCE: 9
agaggtaccc cgggctggta tatttatatg ttgtcaaata actcaaaaac cataaaagtt    60
taagttagca agtgtgtaca ttttacttg aacaaaaata ttcacctact actgttataa    120
atcattatta aacattagag taaagaaata tggatgataa gaacaagagt agtgatattt    180
tgacaacaat tttgttgcaa catttgagaa aattttgttg ttctctcttt tcattggtca    240 aaacaatag agagaaaa aggaagaggg agaataaaaa cataatgtga gtatgagaga    300
gaaagttgta caaaagttgt accaaaatag ttgtacaaat atcattgagg aatttgacaa    360
aagctacaca ataagggtt aattgctgta aataataag gatgacgcat tagagagatg    420
taccattaga gaattttttgg caagtcatta aaagaaaga ataaattatt tttaaaatta    480
aaagttgagt catttgatta aacatgtgat tatttaatga attgatgaaa gagttggatt    540
aaagttgtat tagtaattag aatttggtgt caaatttaat ttgacatttg atctttttcct    600 atatattgcc ccatagagtc agttaactca ttttatatt tcatagatca aataagagaa    660
ataacggtat attaatccct ccaaaaaaaa aaacggtat atttactaaa aaatctaagc    720
cacgtaggag gataacagga tccccgtagg aggataacat ccaatccaac caatcacaac    780

```
aatcctgatg agataaccca ctttaagccc acgcatctgt ggcacatcta cattatctaa    840
atcacacatt cttccacaca tctgagccac acaaaaacca atccacatct ttatcaccca    900
ttctataaaa aatcacactt tgtgagtcta cactttgatt cccttcaaac acatacaaag    960
agaagagact aattaattaa ttaatcatct tgagagaaaa tggagaaaat agtgcttctt   1020
cttgcaatag tcagtcttgt taaaagtgat cagatttgca ttggttacca tgcaaacaat   1080
tcaacagagc aggttgacac aatcatggaa agaacgtta ctgttacaca tgcccaagac   1140
atactggaaa agacacacaa cgggaagctc tgcgatctag atggagtgaa gcctctaatt   1200
ttaagagatt gtagtgtagc tggatggctc ctcgggaacc caatgtgtga cgaattcatc   1260
aatgtaccgg aatggtctta catagtggag aaggccaatc caaccaatga cctctgttac   1320
ccagggagtt tcaacgacta tgaagaactg aaacacctat tgagcagaat aaaccatttt   1380
gagaaaattc aaatcatccc caaaagttct tggtccgatc atgaagcctc atcaggagtt   1440
agctcagcat gtccatacct gggaagtccc tcctttttta gaaatgtggt atggcttatc   1500
aaaaagaaca gtacataccc aacaataaag aaaagctaca ataataccaa ccaagaggat   1560
cttttggtac tgtggggaat tcaccatcct aatgatgcgg cagagcagac aaggctatat   1620
caaaacccaa ccacctatat ttccattggg acatcaacac taaaccagag attggtacca   1680
aaaatagcta ctagatccaa agtaaacggg caaagtggaa ggatggagtt cttctggaca   1740
attttaaaac ctaatgatgc aatcaacttc gagagtaatg gaaatttcat tgctccagaa   1800
tatgcataca aaattgtcaa gaaagggac tcagcaatta tgaaaagtga attggaatat   1860
ggtaactgca acaccaagtg tcaaactcca atgggggcga taaactctag tatgccattc   1920
cacaacatac accctctcac catcggggaa tgccccaaat atgtgaaatc aaacagatta   1980
gtccttgcaa cagggctcag aaatagccct caaagagaga gcagaagaaa aaagagagga   2040
ctatttggag ctatagcagg ttttatagag ggaggatggc agggaatggt agatggttgg   2100
tatgggtacc accatagcaa tgagcagggg agtgggtacg ctgcagacaa agaatccact   2160
caaaaggcaa tagatggagt caccaataag gtcaactcaa tcattgacaa aatgaacact   2220
cagtttgagg ccgttggaag ggaatttaat aacttagaaa ggagaataga gaatttaaac   2280
aagaagatgg aagacgggtt tctagatgtc tggacttata atgccgaact tctggttctc   2340
atggaaaatg agagaactct agactttcat gactcaaatg ttaagaacct ctacgacaag   2400
gtccgactac agcttaggga taatgcaaag gagctgggta acggttgttt cgagttctat   2460
cacaaatgtg ataatgaatg tatggaaagt ataagaaacg gaacgtacaa ctatccgcag   2520
tattcagaag aagcaagatt aaaaagagag gaaataagtg gggtaaaatt ggaatcaata   2580
ggaacttacc aaatactgtc aatttattca acagtggcga gttccctagc actggcaatc   2640
atgatggctg gtctatcttt atggatgtgc tccaatggat cgttacaatg cagaatttgc   2700
atttaagagc tctaagttaa aatgcttctt cgtctcctat ttataatatg gtttgttatt   2760
gttaattttg ttcttgtaga agagcttaat taatcgttgt tgttatgaaa tactatttgt   2820
atgagatgaa ctggtgtaat gtaattcatt tacataagtg gagtcagaat cagaatgttt   2880
cctccataac taactagaca tgaagacctg ccgcgtacaa ttgtcttata tttgaacaac   2940
taaaattgaa catcttttgc cacaacttta taagtggtta atatagctca aatatatggt   3000
caagttcaat agattaataa tggaaatatc agttatcgaa attcattaac aatcaactta   3060
acgttattaa ctactaattt tatatcatcc cctttgataa atgatagtac a            3111
```

```
<210> SEQ ID NO 10
<211> LENGTH: 26
<212> TYPE: PRT
<213> ORGANISM: Medicago sativa

<400> SEQUENCE: 10

Met Ala Lys Asn Val Ala Ile Phe Gly Leu Leu Phe Ser Leu Leu Leu
1               5                   10                  15

Leu Val Pro Ser Gln Ile Phe Ala Glu Glu
            20                  25

<210> SEQ ID NO 11
<211> LENGTH: 25
<212> TYPE: DNA
<213> ORGANISM: Artificial sequence
<220> FEATURE:
<223> OTHER INFORMATION: Synthesized oligonucleotide Plasto-443c

<400> SEQUENCE: 11
gtattagtaa ttagaatttg gtgtc                                         25

<210> SEQ ID NO 12
<211> LENGTH: 34
<212> TYPE: DNA
<213> ORGANISM: Artificial sequence
<220> FEATURE:
<223> OTHER INFORMATION: Synthesized oligonucleotide supP19-plasto.r

<400> SEQUENCE: 12
ccttgtatag ctcgttccat tttctctcaa gatg                               34

<210> SEQ ID NO 13
<211> LENGTH: 20
<212> TYPE: DNA
<213> ORGANISM: Artificial sequence
<220> FEATURE:
<223> OTHER INFORMATION: Synthesized oligonucleotide supP19-1c

<400> SEQUENCE: 13
atggaacgag ctatacaagg                                               20

<210> SEQ ID NO 14
<211> LENGTH: 32
<212> TYPE: DNA
<213> ORGANISM: Artificial sequence
<220> FEATURE:
<223> OTHER INFORMATION: Synthesized oligonucleotide SupP19-SacI.r

<400> SEQUENCE: 14
agtcgagctc ttactcgctt tcttttttcga ag                                32

<210> SEQ ID NO 15
<211> LENGTH: 1214
<212> TYPE: DNA
<213> ORGANISM: Artificial sequence
<220> FEATURE:
<223> OTHER INFORMATION: Synthesized LC fragment of C2B8

<400> SEQUENCE: 15
cactttgtga gtctacactt tgattccctt caaacacata caaagagaag agactaatta   60
attaattaat catcttgaga gaaaatggat tttcaggtgc agattatcag cttcctgcta  120
atcagtgctt cagtcataat gtccagagga caaattgttc tctcccagtc tccagcaatc  180
ctgtctgcat ctccagggga aaggtcaca atgacttgca gggccagctc aagtgtaagt  240
```

| | |
|---|---|
| tacatccact ggttccagca gaagccagga tcctcccca aaccctggat ttatgccaca | 300 |
| tccaacctgg cttctggagt ccctgttcgc ttcagtggca gtgggtctgg gacttcttac | 360 |
| tctctcacaa tcagcagagt ggaggctgaa gatgctgcca cttattactg ccagcagtgg | 420 |
| actagtaacc cacccacgtt cggagggggg accaagctgg aaatcaaacg tacggtggct | 480 |
| gcaccatctg tcttcatctt cccgccatct gatgagcagt tgaaatctgg aactgcctct | 540 |
| gttgtgtgcc tgctgaataa cttctatccc agagaggcca agtacagtg gaaggtggat | 600 |
| aacgccctcc aatcgggtaa ctcccaggag agtgtcacag agcaggacag caaggacagc | 660 |
| acctacagcc tcagcagcac cctgacgctg agcaaagcag actacgagaa acacaaagtc | 720 |
| tacgcctgcg aagtcaccca tcagggcctg agctcgcccg tcacaaagag cttcaacagg | 780 |
| ggagagtgtt gagacgtcgt taaaatgctt cttcgtctcc tatttataat atggtttgtt | 840 |
| attgttaatt ttgttcttgt agaagagctt aattaatcgt tgttgttatg aaatactatt | 900 |
| tgtatgagat gaactggtgt aatgtaattc atttacataa gtggagtcag aatcagaatg | 960 |
| tttcctccat aactaactag acatgaagac ctgccgcgta caattgtctt atatttgaac | 1020 |
| aactaaaatt gaacatcttt tgccacaact ttataagtgg ttaatatagc tcaaatatat | 1080 |
| ggtcaagttc aatagattaa taatgaaat atcagttatc gaaattcatt aacaatcaac | 1140 |
| ttaacgttat taactactaa ttttatatca tccccttga taaatgatag tacaccaatt | 1200 |
| aggaaggaga attc | 1214 |

<210> SEQ ID NO 16
<211> LENGTH: 1919
<212> TYPE: DNA
<213> ORGANISM: Artificial Sequence
<220> FEATURE:
<223> OTHER INFORMATION: Synthesized HC fragment of C2B8

<400> SEQUENCE: 16

| | |
|---|---|
| cactttgtga gtctacactt tgattcccctt caaacacata caaagagaag agactaatta | 60 |
| attaattaat catcttgaga gaaaatgggt tggagcctca tcttgctctt ccttgtcgct | 120 |
| gttgctacgc gtgtcctgtc ccaggtacaa ctgcagcagc ctggggctga gctggtgaag | 180 |
| cctggggcct cagtgaagat gtcctgcaag gcttctggct acacatttac cagttacaat | 240 |
| atgcactggg taaacagac acctggtcgg ggcctggaat ggattggagc tatttatccc | 300 |
| ggaaatggtg atacttccta caatcagaag ttcaaaggca aggccacatt gactgcagac | 360 |
| aaatcctcca gcacagccta catgcagctc agcagcctga catctgagga ctctgcggtc | 420 |
| tattactgtg caagatcgac ttactacggc ggtgactggt acttcaatgt ctggggcgca | 480 |
| gggaccacgg tcaccgtctc tgcagctagc accaagggcc catcggtctt ccccctggca | 540 |
| ccctcctcca agagcacctc tgggggcaca gcggccctgg gctgcctggt caaggactac | 600 |
| ttccccgaac cggtgacggt gtcgtggaac tcaggcgccc tgaccagcgg cgtgcacacc | 660 |
| ttcccggctg tcctacagtc ctcaggactc tactccctca gcagcgtggt gaccgtgccc | 720 |
| tccagcagct tgggcaccca gacctacatc tgcaacgtga atcacaagcc cagcaacacc | 780 |
| aaggtggaca gaaagttga gcccaaatct tgtgacaaaa ctcacacatg cccaccgtgc | 840 |
| ccagcacctg aactcctggg gggaccgtca gtcttcctct tccccccaaa acccaaggac | 900 |
| accctcatga tctcccggac ccctgaggtc acatgcgtgg tggtggacgt gagccacgaa | 960 |
| gaccctgagg tcaagttcaa ctggtacgtg gacggcgtgg aggtgcataa tgccaagaca | 1020 |
| aagccgcggg aggagcagta caacagcacg taccgtgtgg tcagcgtcct caccgtcctg | 1080 |

```
caccaggact ggctgaatgg caaggagtac aagtgcaagg tctccaacaa agccctccca    1140
gcccccatcg agaaaaccat ctccaaagcc aaagggcagc ctagggaacc acaagtgtac    1200
actcttccac catctaggga tgagcttact aagaaccaag tttctcttac ttgtcttgtg    1260
aagggatttt atccatctga catcgccgtg gaatgggaat ccaacggaca accagagaac    1320
aattacaaga ctactccacc agttcttgat tctgatggat ccttctttct ttattccaag    1380
cttactgttg ataagtccag atggcagcaa ggaaatgtgt tctcttgttc tgttatgcac    1440
gaagctcttc ataatcatta tactcaaaag tccctttctc tttctcctgg aaagtgagac    1500
gtcgttaaaa tgcttcttcg tctcctattt ataatatggt ttgttattgt taattttgtt    1560
cttgtagaag agcttaatta atcgttgttg ttatgaaata ctatttgtat gagatgaact    1620
ggtgtaatgt aattcattta cataagtgga gtcagaatca gaatgtttcc tccataacta    1680
actagacatg aagacctgcc gcgtacaatt gtcttatatt tgaacaacta aaattgaaca    1740
tcttttgcca caactttata agtggttaat atagctcaaa tatatggtca agttcaatag    1800
attaataatg gaaatatcag ttatcgaaat tcattaacaa tcaacttaac gttattaact    1860
actaatttta tatcatcccc tttgataaat gatagtacac caattaggaa ggagaattc    1919
```

METHOD OF PREPARING PLANT-DERIVED PROTEINS

CROSS REFERENCE TO RELATED APPLICATIONS

The present application is a National Phase Application of International Application No. PCT/CA2010/001489, filed Sep. 21, 2010, which claims the benefit of U.S. Patent Applications No. 61/244,786, filed Sep. 22, 2009, which applications are incorporated herein fully by this reference.

FIELD OF INVENTION

The present invention relates to methods of preparing plant-derived proteins. More specifically, the present invention provides methods to obtain proteins, including protein suprastructures, from plants and plant tissues.

BACKGROUND OF THE INVENTION

Current recombinant expression strategies in host cells such as *E. coli*, insect cell culture, and mammalian cell culture express and secrete proteins at very high level in the culture media. Using these systems high levels of expression, proper protein folding and post-translational modification of proteins, is achieved. Furthermore, purification of the expressed protein is simplified since intracellular proteins may be readily segregated from other components (DNA, vesicle, membranes, pigments, and so on). For plant or yeast expression systems, the cell wall prevents secretion of expressed protein into the culture media.

Different approaches are widely used in science to generate cell-extracts. Mechanical approaches to disrupt cell wall and liberate its content are not usually selective for certain class of protein or cellular components. Directing expression of a protein of interest into the cell culture media, allowing intracellular contaminants to be removed by centrifugation or by filtration, allow simple and fast enrichment of the protein of interest. It may also be desirable to separate the a protein or a protein suprastructure of interest, including protein rosettes, nanoparticles, large protein complexes, antibodies or virus-like particles (VLPs), and the like, from some, or all of the proteins, DNA, membrane fragments, vesicles, pigments, carbohydrates, etc. present in the plant or plant matter before the protein suprastructure of interest is used in vaccine formulation.

Immunoglobulins (IgGs) are complex heteromultimeric proteins with characteristic affinity for specific antigenic counterparts of various natures. Today, routine isolation of IgG-producing cell lines, and the advent of technologies for IgG directed evolution and molecular engineering have profoundly impacted their evolution as biotherapeutics and in the general life science market. Therapeutic monoclonal IgG (monoclonal antibodies, mAbs) dominate the current market of new anti-inflammatory and anti-cancer drugs and hundreds of new candidates are currently under research and clinical development for improved or novel applications. The annual market demand for mAbs ranges from a few grams (diagnostics), a few kilograms (anti-toxin) to up to one or several hundreds of kilograms (bio-defense, anti-cancer, anti-infectious, anti-inflammatory). Methods to produce modified glycoproteins from plants is described in WO 2008/151440 (which is incorporated herein by reference).

A method for extracting protein from the intercellular space of plants, comprising a vacuum and centrifugation process to provide an interstitial fluid extract comprising the protein of interest is described in PCT Publication WO 00/09725 (to Turpen et al.). This approach is suitable for small proteins (of 50 kDa or smaller) that pass through network of microfibers under vacuum and centrifugation, but is not suitable for larger proteins, superstructure proteins, protein rosettes, nanoparticles, large protein complexes, such as antibodies or VLPs.

McCormick et al 1999 (Proc Natl Acad Sci USA 96:703-708) discloses use of a rice amylase signal peptide fused to a single-chain Fv (scFv) epitope to target the expressed protein to the extracellular compartment, followed by vacuum infiltration of leaf and stem tissue for recovery of the scFv polypeptides. Moehnke et al., 2008 (Biotechnol Lett 30:1259-1264) describes use of the vacuum infiltration method of McCormick to obtain a recombinant plant allergen from tobacco using an apoplastic extraction. PCT Publication WO 2003/025124 (to Zhang et al) discloses expression of scFv immunoglobulins in plants, targeting to the apoplastic space using murine signal sequences.

Virus-like particles (VLPs) may be employed to prepare influenza vaccines. Suprastructures such as VLPs mimic the structure of the viral capsid, but lack a genome, and thus cannot replicate or provide a means for a secondary infection. VLPs offer an improved alternative to isolated (soluble) recombinant antigens for stimulating a strong immune response. VLPs are assembled upon expression of specific viral proteins and present an external surface resembling that of their cognate virus but, unlike true viral particle, do not incorporate genetic material. The presentation of antigens in a particulate and multivalent structure similar to that of the native virus achieves an enhanced stimulation of the immune response with balanced humoral and cellular components. Such improvement over the stimulation by isolated antigens is believed to be particularly true for enveloped viruses as enveloped VLPs present the surface antigens in their natural membrane-bound state (Grgacic and Anderson, 2006, Methods 40, 60-65). Furthermore, Influenza VLPs, with their nanoparticle organization, have been shown to be better vaccine candidates compared to recombinant hemagglutinin HA (i.e. monomeric HA, or HA organized into rosettes; assembly of 3-8 trimers of HA), and they are able to activate both humoral and cellular immune response. (Bright, R. A., et. al., 2007, *Vaccine* 25, 3871-3878).

Influenza VLPs have been obtained in cultured mammalian cells from the co-expression of all 10 influenza proteins (Mena et al., 1996, *J. Virol.* 70, 5016-5024). Several viral proteins are dispensable for the production of VLPs, and influenza VLPs in vaccine development programs have been produced from the co-expression of the 2 major antigenic envelope proteins (HA and NA) with M1 or from the co-expression of HA and M1 only (Kang et al., 2009, Virus Res. 143, 140-146). Chen et al. (2007, *J. Virol.* 81, 7111-7123) have shown that HA alone is capable of driving VLP formation and budding and M1 co-expression could be omitted in their system. However, since HA was found to bind to sialylated glycoproteins on the surface of the mammalian cells producing the VLPs, a viral sialidase was co-expressed to allow the release of VLPs from the producing cell after budding.

PCT Publication WO 2006/119516 (to Williamson and Rybicki) discloses expression of full length and truncated human-codon optimized H5 HA of Influenza A/Vietnam/1194/2004 in plants. The truncated construct lacks the membrane anchoring domain. The highest accumulation of HA protein was obtained with constructs that targeted to the ER. Constructs lacking a membrane targeting domain did not yield detectable HA. The production of VLPs was not reported.

The production of influenza HA VLPs that comprise a lipid envelope has been previously described by the inventors in WO 2009/009876 and WO 2009/076778 (to D'Aoust et al.; both of which are incorporated herein by reference). For enveloped viruses, it may be advantageous for a lipid layer or membrane to be retained by the virus. The composition of the lipid may vary with the system (e.g. a plant-produced enveloped virus would include plant lipids or phytosterols in the envelope), and may contribute to an improved immune response.

The assembly of enveloped VLPs in transgenic tobacco expressing the HBV surface antigen (HBsAg) was described by Mason et al. (1992, Proc. Natl. Acad. Sci. USA 89, 11745-11749). Plant-produced HBV VLPs were shown to induce potent B- and T-cell immune responses in mice when administered parenterally (Huang et al., 2005, Vaccine 23, 1851-1858) but oral immunization through feeding studies only induced a modest immune response (Smith et al., 2003, Vaccine 21, 4011-4021). Greco (2007, Vaccine 25, 8228-8240) showed that human immunodeficiency virus (HIV) epitopes in fusion with HBsAg accumulated as VLP when expressed in transgenic tobacco and Arabidopsis, creating a bivalent VLP vaccine.

Expression of the viral capsid protein (NVCP) in transgenic tobacco and potato plants resulted in the assembly of non-enveloped VLPs (Mason et al., 1996, Proc. Natl. Acad. Sci. USA 93, 5335-5340). NVCP VLPs have been produced in agroinfiltrated N. benthamiana leaves (Huang et al. 2009, Biotechnol. Bioeng. 103, 706-714) and their immunogenicity upon oral administration demonstrated in mice (Santi et al., 2008, Vaccine 26, 1846-1854). Administration of 2 or 3 doses of raw potatoes containing 215-751 µg of NVCP in the form of VLPs to healthy adult volunteers resulted in development of an immune response in and 95% of the immunized volunteers (Tacket et al. 2000, J. Infect. Dis. 182, 302-305). Non-enveloped VLPs have also been obtained from the expression of HBV core antigen (HBcAg; Huang et al., 2009, Biotechnol. Bioeng. 103, 706-714), and the human papillomavirus (HPV) major capsid protein L1 (Varsani et al., 2003, Arch. Virol. 148, 1771-1786).

A simpler protein, or protein suprastructure production system, for example, one that relies on the expression of only one or a few proteins is desirable. Production of proteins, or protein suprastructures, for example but not limited to protein rosettes, nanoparticles, large protein complexes such as antibodies or VLPs, in plant systems is advantageous, in that plants may be grown in a greenhouse or field, and do not require aseptic tissue culture methods and handling.

Methods of preparing the proteins, or proteins, or suprastructure proteins, that are substantially free of, or easily separated from plant proteins, yet retain the structural and characteristics of the protein are desired.

SUMMARY OF THE INVENTION

The present invention relates to methods of preparing plant-derived proteins. More specifically, the present invention provides methods to obtain proteins, including protein suprastructures from plants and plant tissues.

It is an object of the invention to provide an improved method of preparing plant-derived proteins.

The present invention provides a method (A) of preparing plant-derived proteins, or proteins, or suprastructure proteins, comprising obtaining a plant or plant matter comprising the plant-derived proteins, or suprastructure proteins, localized within the apoplast; producing a protoplast and an apoplast fraction, the apoplast fraction comprising plant-derived proteins, or suprastructure proteins; and recovering the apoplast fraction. The method may further comprise a step of purifying the plant derived proteins, or proteins, or suprastructure proteins, from the apoplast fraction. The plant-derived proteins, or proteins, or suprastructure proteins, may be a chimeric plant-derived proteins, or suprastructure protein. The plant-derived proteins, or proteins, or suprastructure proteins, may be heterologous to the plant. The plant derived proteins, or proteins, or suprastructure proteins, may include a protein rosette, a protein complex, a proteasome, a metabolon, a transcription complex, a recombination complex, a photosynthetic complex, a membrane transport complex, a nuclear pore complex, a protein nanoparticle, a glycoprotein, an antibody, a polyclonal antibody, a monoclonal antibody, a single chain monoclonal antibody, a virus like particle, a viral envelope protein, a viral structural protein, a viral capsid protein, and a viral coat protein, a chimeric protein, a chimeric protein complex, a chimeric protein nanoparticle, a chimeric glycoprotein, a chimeric antibody, a chimeric monoclonal antibody, a chimeric single chain monoclonal antibody, a chimeric hemagglutinin, a viral envelope protein, a viral structural protein, a viral capsid protein, and a viral coat protein. The plant derived monoclonal antibody may comprise a chimeric mouse human monoclonal antibody, for example but not limited to C2B8. The plant derived VLPs may comprise influenza hemagglutinin.

The apoplast and protoplast fractions may be produced by treatment of the plant or plant matter by an enzyme composition. The enzyme composition may comprise one or more than one pectinase, one or more than one cellulase, or one or more than one pectinase and one or more than one cellulase. Furthermore, if desired, the enzyme composition does not include a lipase or protease, or the composition does not include an added lipase or protease.

Plant or plant matter may be obtained by growing, harvesting or growing and harvesting the plant. The plant matter may comprise some or all of the plant, one or more than one plant cell, leaves, stems, roots or cultured plant cells.

The present invention provides a method of preparing plant derived proteins, or proteins, or suprastructure proteins, as described above (Method A), wherein a nucleic acid encoding the proteins, or suprastructure proteins, is introduced into the plant in a transient manner. Alternatively, the nucleic acid is stably integrated within a genome of the plant.

The present invention provides a method of preparing plant derived proteins, or suprastructure proteins, as described above (Method A) further comprising a step of purifying the plant derived proteins, or suprastructure proteins, from the apoplast fraction. The step of purifying may comprise filtering the apoplast fraction using depth filtration to produce a clarified extract, followed by chromatography of the clarified extract using a cation exchange resin, affinity chromatography, size exclusion chromatography, or a combination thereof.

Without wishing to be bound by theory, proteins obtained from the apoplast are more homogenous, as the intermediate forms of post-translationally modified proteins, or proteins comprising other types of processing that occurs in various intracellular compartments, for example the mitochondria, chloroplast, and other organelles are not co-extracted. A higher degree of homogeneity of a recombinant protein typically results in a higher quality of a preparation comprising the protein, and may result in a product with beneficial properties including higher potency, longer half-life, or better immunogenic capacity. For example, blood proteins containing high-mannose glycosylation are eliminated in blood circulation more rapidly than proteins comprising complex glycosylation. A glycosylated protein produce in the apoplastic fraction exhibits more complex-type glycosylation. Therefore, an apoplast-derived protein prepared using the methods described herein, involving cell-wall digestion, exhibit, for example, a better half life in circulation.

The plant derived proteins, or suprastructure proteins, may include protein rosettes, protein complexes, protein nanoparticles, antibodies, monoclonal antibodies, VLPs. The VLPs may comprise one or more influenza HA polypeptides. The suprastructure protein may be a chimeric suprastructure protein, for example, the monoclonal antibody may be a chimeric monoclonal antibody, or the influenza HA polypeptide, may be a chimeric HA polypeptide. If the suprastructure protein is a VLP, then the plant-derived VLP may further comprise hemagglutinating activity. Plant or plant matter may be obtained by growing, harvesting or growing and harvesting the plant. The plant matter may comprise some or all of the plant, or one or more than one plant cell, leaves, stems, roots or cultured cells.

The present invention also provides a method (B) of preparing plant derived proteins, or suprastructure proteins, comprising obtaining a plant or plant matter comprising plant-derived proteins, or suprastructure proteins, digesting the plant matter using a cell wall degrading enzyme composition to produced a digested fraction, and filtering the digested fraction to produced a filtered fraction and recovering the plant-derived proteins, or suprastructure proteins, from the filtered fraction.

The enzyme composition may comprise one or more than one pectinase, one or more than one cellulase, or one or more than one pectinase and one or more than one cellulase. Furthermore, if desired, the enzyme composition does not include a lipase or protease, or the composition does not include an added lipase or protease. The plant-derived suprastructure protein may be a chimeric plant-derived suprastructure protein. The plant derived protein suprastructure may include a protein rosette, a protein complex, a proteasome, a metabolon, a transcription complex, a recombination complex, a photosynthetic complex, a membrane transport complex, a nuclear pore complex, a protein nanoparticle, a glycoprotein, an antibody, a polyclonal antibody, a monoclonal antibody, a single chain monoclonal antibody, a virus like particle, a viral envelope protein, a viral structural protein, a viral capsid protein, and a viral coat protein, a chimeric protein, a chimeric protein complex, a chimeric protein nanoparticle, a chimeric glycoprotein, a chimeric antibody, a chimeric monoclonal antibody, a chimeric single chain monoclonal antibody, a chimeric hemagglutinin, a viral envelope protein, a viral structural protein, a viral capsid protein, and a viral coat protein. The plant derived monoclonal antibody may comprise a chimeric mouse human monoclonal antibody, for example but not limited to C2B8. The plant derived VLPs may comprise influenza hemagglutinin.

The present invention provides a method of preparing plant derived proteins, or suprastructure proteins, as described above (Method B), wherein a nucleic acid encoding the proteins, or suprastructure proteins, is introduced into the plant in a transient manner. Alternatively, the nucleic acid is stably integrated within a genome of the plant.

The present invention provides a method of preparing plant derived VLPs as described above (Method B) further comprising a step of separating the proteins, or suprastructure proteins, in the filtered fraction from the cellular debris and insoluble materials. The step of separating may be performed by centrifugation, by depth filtration, or bother centrifugation and depth filtration to produce a clarified fraction. The plant derived proteins, or suprastructure proteins, may be further purified by chromatography, for example, the clarified extract may be purified using a cation exchange resin, an affinity resin, size exclusion chromatograph, or a combination thereof.

The plant derived proteins, or suprastructure proteins, may include protein rosettes, protein complexes, protein nanoparticles, glycoproteins, antibodies, monoclonal antibodies, VLPs. The VLPs may comprise one or more influenza HA polypeptides. The suprastructure protein may be a chimeric suprastructure protein, for example, the monoclonal antibody may be a chimeric monoclonal antibody, or the influenza HA polypeptide, may be a chimeric HA polypeptide. If the suprastructure protein is a VLP, then the plant-derived VLP may further comprise hemagglutinating activity.

Without wishing to be bound by theory, plant-made VLPs comprising plant derived lipids, may induce a stronger immune reaction than VLPs made in other manufacturing systems and that the immune reaction induced by these plant-made VLPs is stronger when compared to the immune reaction induced by live or attenuated whole virus vaccines.

The composition of a protein extract obtained from a host cell is complex and typically comprises intercellular and intracellular components along with a protein or suprastructure of interest that is to be isolated. Preparation of an apoplastic fraction, followed by a step to segregate the intracellular proteins and components is advantageous since the protein or suprastructure of interest can be enriched and increase efficiency within a manufacturing process. Having a simpler process, comprising fewer efficient steps, may result in significant yield increases, and cost reduction. It has also been found that the process of digesting the cell wall using cell wall degrading enzymes increases suprastructure protein yield even if protoplasts do not remain intact during the extraction procedure. Without wishing to be bound by theory, the step of cell wall digestion may loosen the polymeric components of the cells wall and assist in release of the proteins, or suprastructure proteins, otherwise associated within the cell wall. This protocol may also minimize contamination of the proteins, or suprastructure proteins, within intracellular components.

Methods to digest plant cell-wall are known, and enzyme cocktail mixtures that digest cell walls may vary. The present invention is not limited by the cell wall digestion method used.

The methods described herein result in less disruption, and contamination of a plant-derived suprastructure protein extract when compared to methods for preparing plant-derived suprastructure protein involving homogenization, blending or grinding. The methods described herein provide an apoplast fraction of the plant tissue and that may maintain the integrity of protoplasts and their components. The method as described herein is effective in purifying proteins, or suprastructure proteins, even if the protoplasts, or a portion of the protoplasts, lose their integrity and are no longer intact.

These methods provide a higher yield of proteins, or suprastructure proteins, when compared to methods of suprastructure protein extraction involving standard tissue disruption techniques, for example, homogenization, blending or grinding. The greater yield may be due to, in part, a reduction of the shearing forces that disrupt the structural integrity of the proteins, or suprastructure proteins, and in the case of VLPs, the lipid envelope. Preparation of proteins, or suprastructure proteins, from an apoplastic fraction may be advantageous, as apoplastic fractions are significantly reduced, or free of, cytoplasmic proteins. Therefore, separation of the suprastructure protein from other proteins and matter, including monomers, dimmers, trimers or fragments of the suprastructure protein, in the apoplastic fraction is easily carried out. However, increased yields of proteins, or suprastructure proteins, may also be obtained using the methods described herein, even if the protoplast preparation, or a portion of the protoplast preparation, is not intact.

Glycoproteins, including suprastructure glycoproteins, for example monoclonal antibodies, that are secreted into the apoplast comprises a higher percentage of N-glycans that have completed their maturation and comprise terminal N-acetylglucosamine or galactose residues (complex N-glycans), compared to extraction methods that do not digest the cell wall, for example blender extracted plants. Suprastructure glycoproteins, for example monoclonal antibodies, comprising complex N glycans have been found to exhibit the beneficial property of increased half life in the blood stream when compared to monoclonal antibodies comprising terminal mannose residues (immature N glycans).

Using enzymatic digestion of the cells wall, it may be possible to liberate a pool of apoplastic antibodies comprising N-glycans that have completed their maturation. This method of extraction may allow the recovery of an enriched population, or a homogeneous population of glycosylated antibodies bearing complex N-glycans, separating the immature forms of the glycosylated antibodies in the protoplast fraction. If the pool of antibodies bearing immature N-glycans is desired, the protoplast fraction can be retained and antibodies purified from the protoplast fraction.

The VLPs of the present invention are also characterized as exhibiting a greater hemagglutinating activity than those obtained using standard tissue disruption techniques. This improved hemagglutinating activity may result from a greater yield of intact VLPs (fewer HA monomers or trimers free in solution), a greater yield of intact VLPs with intact lipid envelopes, or a combination thereof.

Vaccines made using VLPs provide the advantage, when compared to vaccines made of whole viruses, that they are non-infectious. Therefore, biological containment is not an issue and it is not required for production. Plant-made VLPs provide a further advantage by allowing the expression system to be grown in a greenhouse or field, thus being significantly more economical and suitable for scale-up.

Additionally, plants do not comprise enzymes involved in synthesizing and adding sialic acid residues to proteins. VLPs may be produced in the absence of neuraminidase (NA), and there is no need to co-express NA, or to treat the producing cells or extract with sialidase (neuraminidase), to ensure VLP production in plants.

This summary of the invention does not necessarily describe all features of the invention.

BRIEF DESCRIPTION OF THE DRAWINGS

These and other features of the invention will become more apparent from the following description in which reference is made to the appended drawings wherein:

FIG. 2 shows sequences. FIG. 2A shows the nucleic acid sequence (SEQ ID NO. 1) of a portion of construct for expressing H5/Indo (construct number 685) from PacI (upstream of the 35S promoter) to AscI (immediately downstream of the NOS terminator). Coding sequence of H5 from A/Indonesia/5/2005 is underlined. FIG. 2B shows the amino acid sequence (SEQ ID NO. 2) of H5 A/Indonesia/5/05 hemagglutinin encoded by construct number 685.

FIG. 3 shows characterization of hemagglutinin (HA)-containing structures by size exclusion chromatography (SEC). Following centrifugation of the digested plant extract, the pellet was resuspended and fractionated by SEC.

FIG. 5 shows the nucleic acid sequence (SEQ ID NO: 9) of an HA expression cassette comprising alfalfa plastocyanin promoter and 5' UTR, hemagglutinin coding sequence of H5 from A/Indonesia/5/2005 (Construct #660), alfalfa plastocyanin 3' UTR and terminator sequences.

FIG. 9 shows the sequence of the DNA fragment synthesized for the assembly of construct #590 (LC fragment; (SEQ ID NO.15).

FIG. 10 shows the sequence of the DNA fragment synthesized for the assembly of construct #592 (HC fragment) (SEQ ID NO.16).

FIG. 13A shows a comparison of the proportion of oligomannosidic N-glycans on C2B8 purified by mechanical disruption (blender extraction) and enzymatic digestion of cell walls.

DETAILED DESCRIPTION

Figure 1:
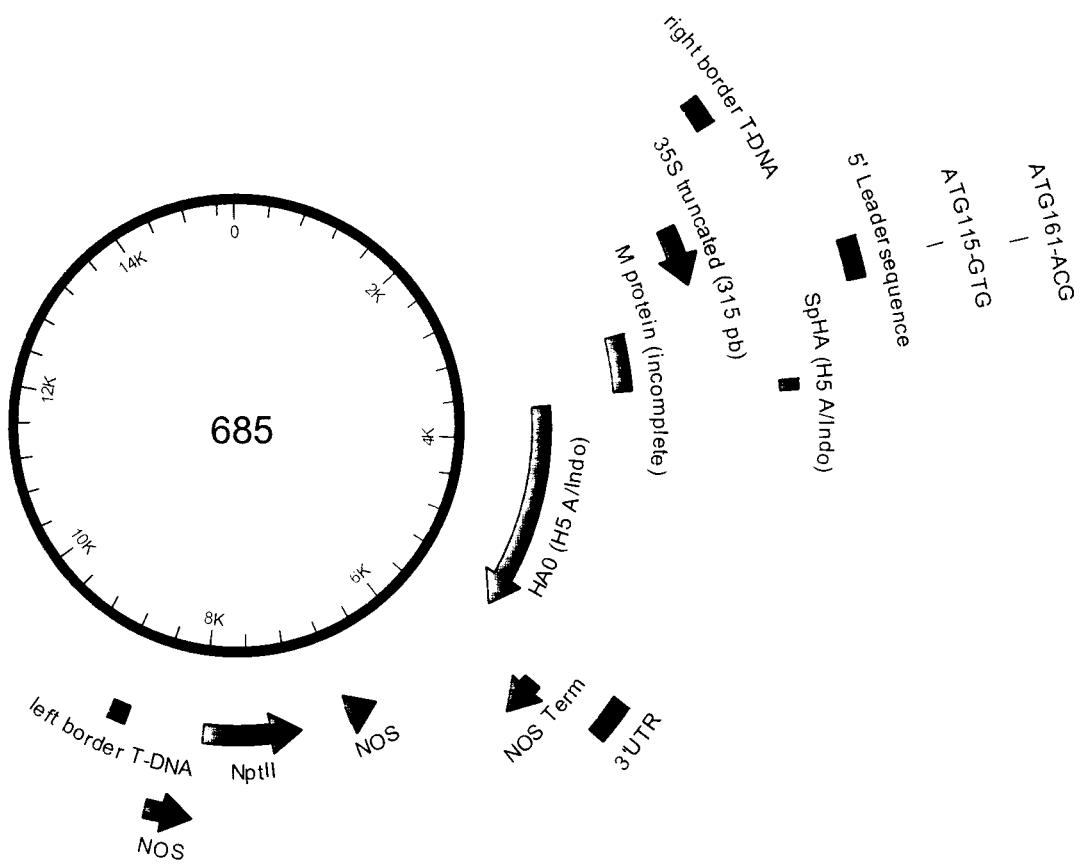
FIG. 1 shows a schematic representation of CPMVHT-based expression cassette (construct 685) for the expression of H5 A/Indonesia/5/05 hemagglutinin.
Figure 3A:
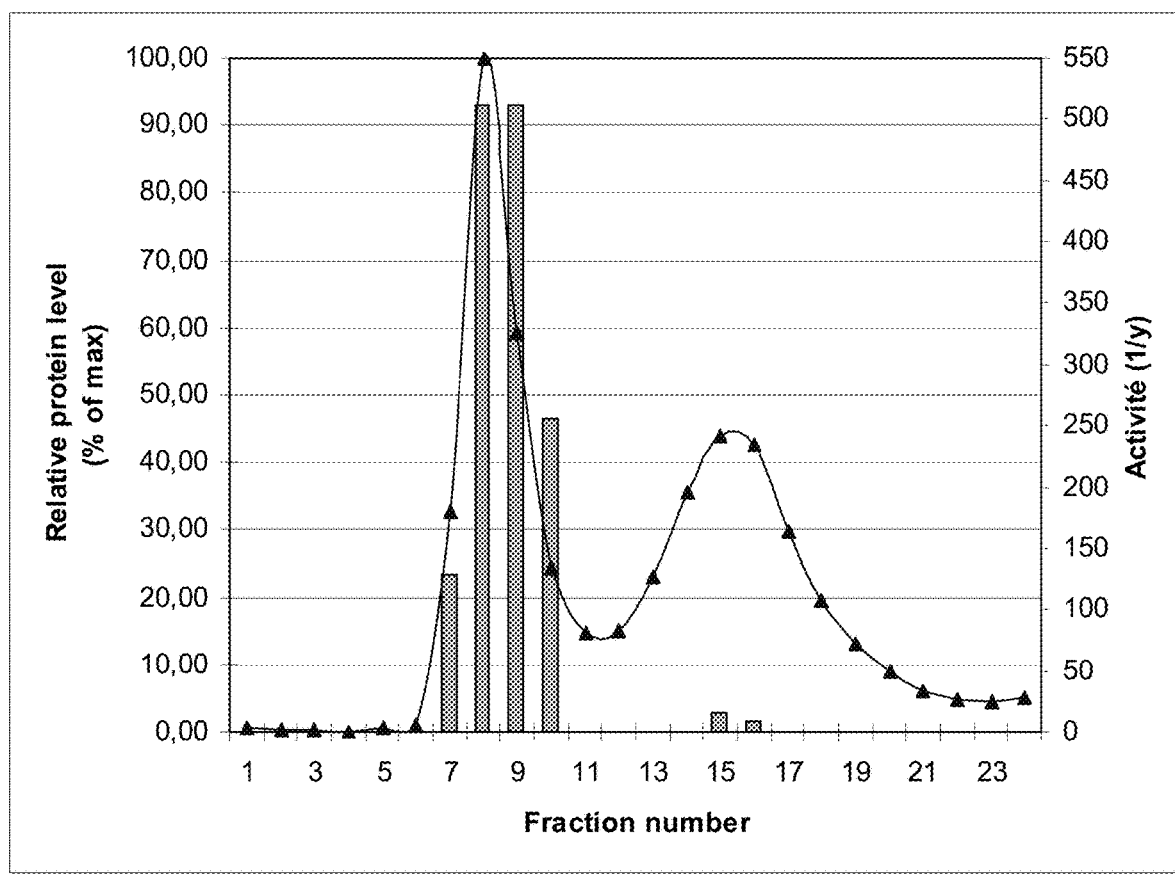
FIG. 3A shows the total soluble protein content per fraction (solid triangles; % of maximum, left-side Y-axis; determined using the Bradford method). The hemagglutinating activity of the collected fractions (solid bars; right-side Y axis) is also shown.
Figure 3B:
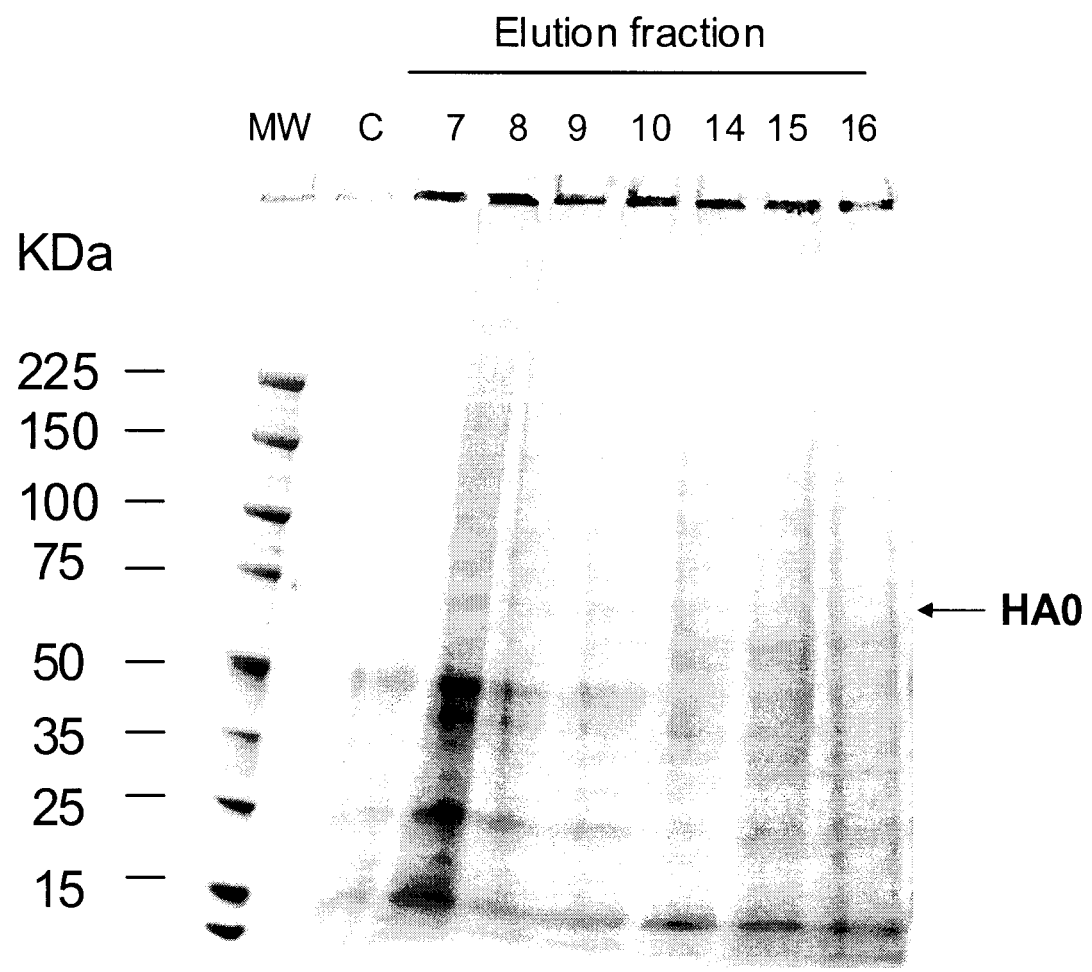
FIG. 3B shows SDS-PAGE analysis of SEC eluted fractions. Fractions were precipitated by acetone and re-suspended in 1/40 volume of reducing sample loading buffer prior to analysis. Gel was stained with 0.1% Coomassie R-250 solution. Purified VLPs were run as a control. The band corresponding to the HA0 monomer is indicated by an arrow. MW—Molecular weight standards (kDa); C—Purified VLPs (control); lanes 7 through 10 and 14 through 16 correspond to fractions number eluted from SEC analysis, shown in FIG. 3A.
Figure 4:
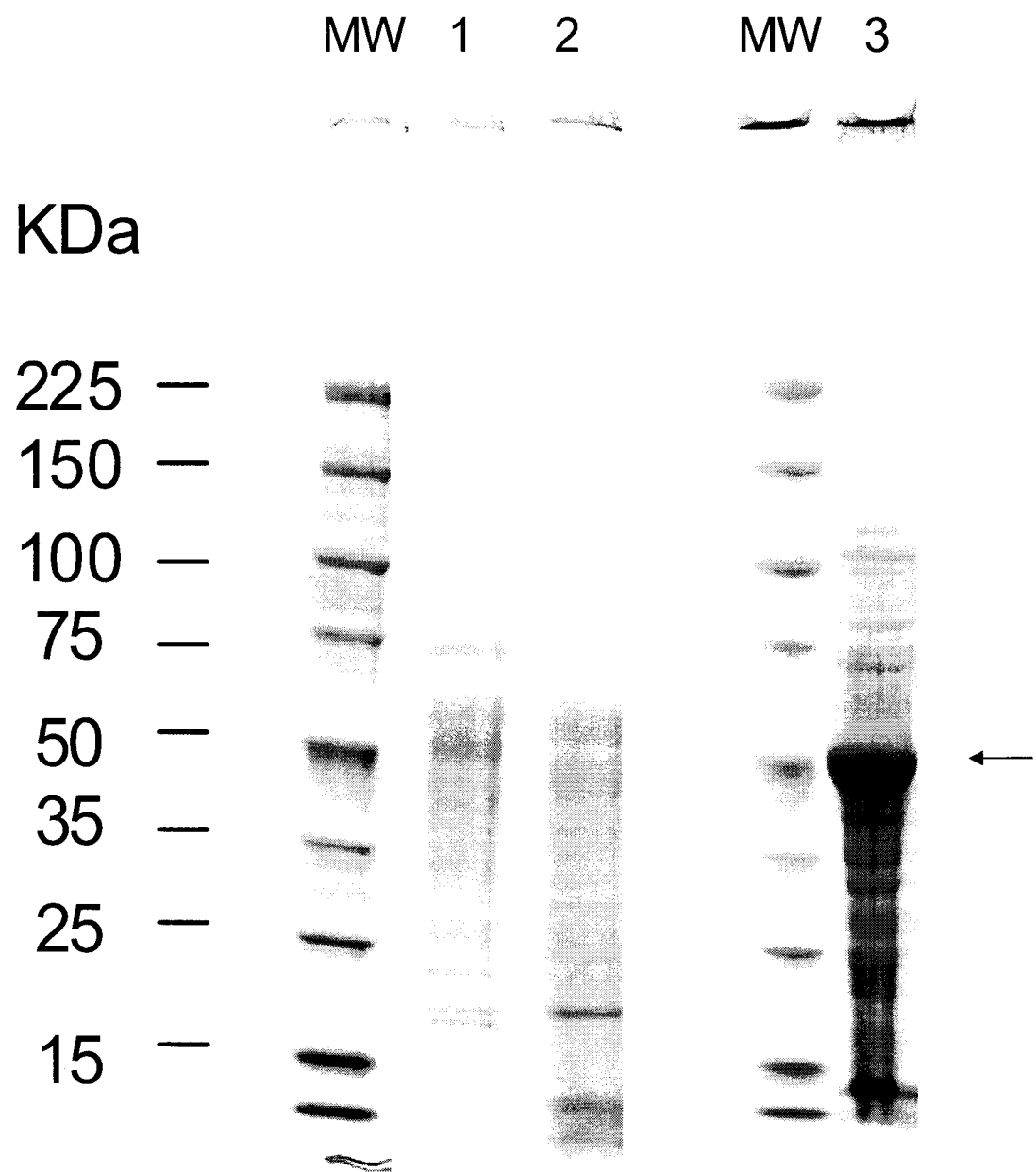
FIG. 4 shows a comparison of protein profiles obtained after enzymatic digestion and by mechanical homogenization using a Comitrol™ homogenizer. Samples were treated in denaturing sample loading buffer and proteins were separated by SDS-PAGE analysis of elution fractions. Gels were stained with 0.1% Coomassie R-250 solution. MW—Molecular weight standards (kDa); lane 1-25 µl enzyme mixture; lane 2-25 µl enzymatic digestion of plant tissue and lane 3-5 µl extract obtained with the Comitrol homogenizer.
Figure 6:
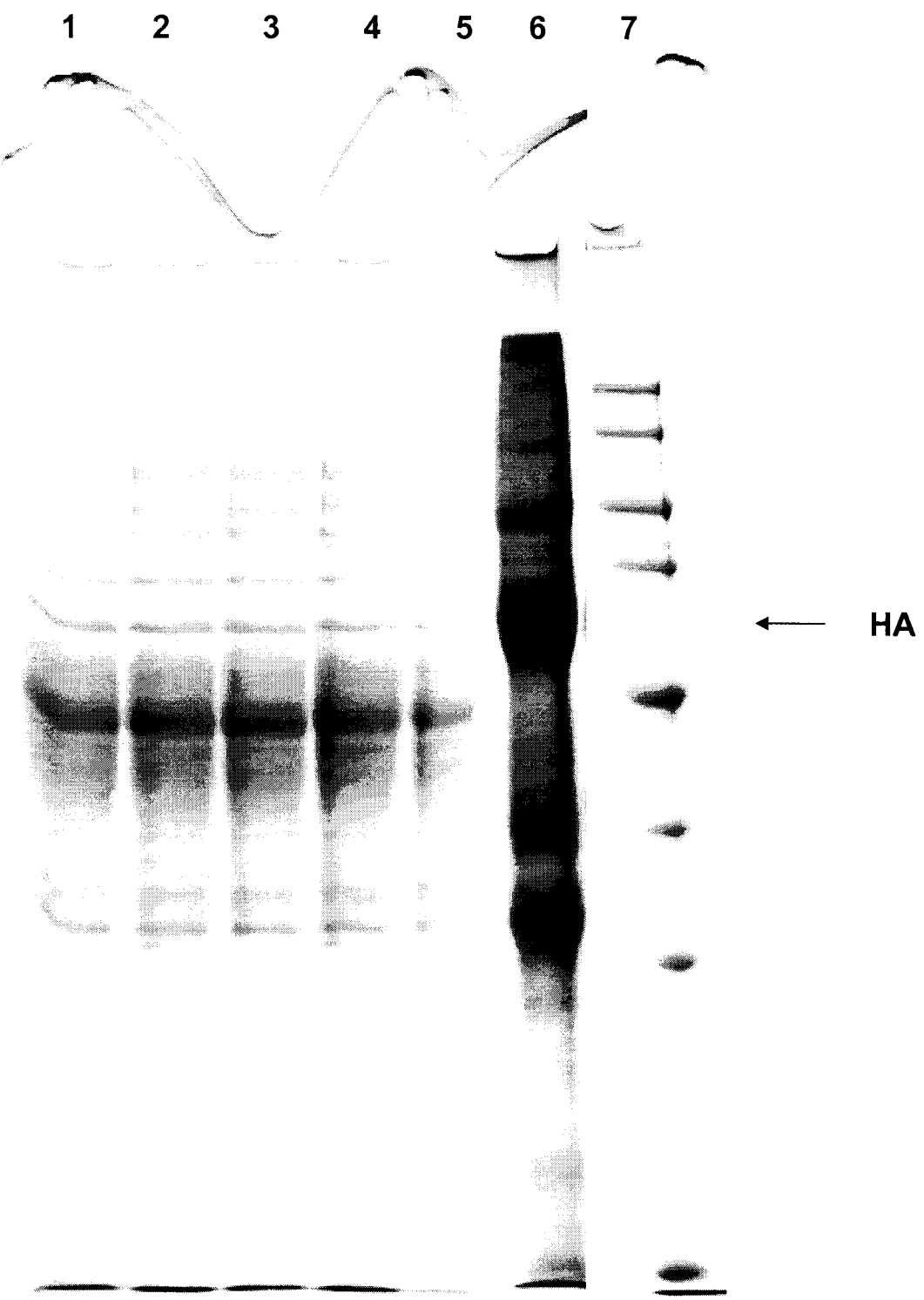
FIG. 6 shows the capture of HA-VLP on cationic exchange resin directly form separation of HA-VLP in the apoplastic fraction. Samples were treated in non-reducing, denaturing sample loading buffer and proteins were separated by SDS-PAGE. Gels were stained with 0.1% Coomassie R-250 solution. Lane 1: Apoplastic fraction after centrifugation, Lane 2-3: Apoplastic fraction after successive microfiltration; Lane 4: Load of the cationic exchange; Lane 5: Flow through fraction of the cationic exchange. Lane 6; elution from cationic exchange, concentrated 10×; Lane 7: Molecular weight standards (kDa).

The present invention relates to methods of preparing plant-derived proteins. More specifically, the present invention provides methods to obtain proteins, or proteins, or proteins, or suprastructure proteins, from plants and plant tissues.

The following description is of a preferred embodiment.

The present invention provides a method for obtaining a protein, or protein suprastructure of interest. The protein of interest may be present in the apoplast or extracellular compartment, corresponding to the plant cell portion excluding the protoplast/spheroplast compartment. The method involves removing, digesting or both digesting and removing the cellulosic plant cell wall that surrounds plant cells. By digesting the cell wall the polymeric components of the cell wall are loosened, and the protein or proteins, or proteins, or suprastructure proteins, of interest may be more readily released. By using this method, the protein or proteins, or proteins, or suprastructure proteins, of interest is enriched since the protoplast/spheroplast compartment that contains a majorly host-cell proteins and components is segregated from the apoplast. As noted below, the method as provided herein is still effective in obtaining a protein or protein suprastructure of interest, if during the process the integrity of the protoplast/spheroplast compartment is lost, if the protoplast/spheroplast compartment is not intact, and if a portion of host cell proteins and components from the protoplast/spheroplast compartment are present in the apoplast fraction. Using the methods described below, if the integrity of the protoplast/spheroplast compartment is lost, the protein or protein suprastructure may still be separated from intact organelles, including the mitochondria, chloroplast and other organelles, and beneficial results may still be obtained.

By "protein" or "protein of interest" (these terms are used interchangeably), it is meant a protein, or protein subunit encoded by a nucleotide sequence, or coding region, that is to be expressed within a plant or portion of the plant. Proteins may have a molecular weight from about 1 to about 100 kDa or any amount therebetween, for example, 1, 2, 4, 6, 8, 10, 12, 14, 16, 18, 20, 22, 24, 26, 28, 30, 35, 40, 45, 50, 55, 60, 65, 70, 75, 80, 85, 90, 95, 100 kDa, or any amount therebetween. A protein may be monomeric, dimeric, trimeric, or multimeric.

A protein suprastructure, also termed suprastructure protein, protein superstructure, or superstructure protein, is a protein structure comprised of two or more polypeptides. The polypeptides may be the same, or different; if different, they may be present in a ratio of about 1:1 to about 10:1 or greater. Suprastructure proteins, may include, but are not limited to protein rosettes, protein complexes, protein nanoparticles, glycoproteins, antibodies, polyclonal antibodies, monoclonal antibodies, single chain monoclonal antibodies, or virus like particles, proteasomes, metabolons, transcription complexes, recombination complexes, photosynthetic complexes, membrane transport complexes, nuclear pore complexes, chimeric proteins, chimeric protein complexes, chimeric protein nanoparticles, chimeric glycoproteins, chimeric antibodies, chimeric monoclonal antibodies, chimeric single chain monoclonal antibodies, or chimeric hemagglutinin (HA). If the protein suprastructure is a VLP, the VLP may be selected from the group of viral envelope proteins, viral structural proteins, viral capsid proteins, and viral coat proteins. The plant derived VLPs may comprise influenza (HA).

Typically a protein suprastructure (protein superstructure), when assembled, is large, for example having a molecular weight greater than 75 kDa, for example from about 75 to about 1500 kDa or any molecular weight therebetween. For example, the protein suprastructure may have a molecular weight from about 75, 80, 85, 90, 100, 110, 120, 130, 140, 150, 160, 170, 180, 200, 220, 240, 260, 280, 300, 320, 340, 360, 380, 400, 425, 450, 475, 500, 525, 550, 575, 600, 625, 650, 675, 700, 725, 750, 775, 800, 850, 900, 950, 1000, 1100, 1150, 1200, 1250, 1300, 1350, 1400, 1450, 1500 kDa, or any amount therebetween, Subunits that combine together to make up the protein suprastructure may be of a smaller molecular weight, for example each subunit having a molecular weight from about 1 kDa to about 500 kDa, or any amount therebetween. A protein suprastructure may comprise a protein exhibiting a secondary structure, with one or more amino acids hydrogen bonded, for example with residues in protein helices, a tertiary structure, having a 3-dimensional configuration, or a quaternary structure having an arrangement of multiple folded proteins or coiled protein molecules that form a multi-subunit complex.

A multiprotein complex (or a protein complex) may comprise a group of two or more associated polypeptide chains. If the different polypeptide chains contain different protein domains, then the resulting multiprotein complex can have multiple catalytic functions. The protein complex may also be a multienzyme polypeptide, comprising multiple catalytic domains within a single polypeptide chain. Protein complexes are typically in the form of quaternary structure. Examples of protein complexes that typically may not survive intact using standard protein isolation protocols, but that may be obtained using the methods described herein include proteasomes (for degradation of peptides and proteins), metabolons (for oxidative energy production), ribosomes (for protein synthesis; e.g. as described in Pereira-Leal, J. B.; et. al., 2006, Philos Trans R Soc Lond B Biol Sci., 361(1467):507-517), transcription complexes, recombination complexes, photosynthetic complexes, membrane transport complexes, nuclear pore complexes. The present method may be used to obtained protein complexes that are characterized as having stable or weaker protein domain-protein domain interactions.

Examples of a protein, or a protein suprastructure, include, for example but not limited to, an industrial enzyme for example, cellulase, xylanase, protease, peroxidase, subtilisin, a protein supplement, a nutraceutical, a value-added product, or a fragment thereof for feed, food, or both feed and food use, a pharmaceutically active protein, for example but not limited to growth factors, growth regulators, antibodies, antigens, and fragments thereof, or their derivatives useful for immunization or vaccination and the like. Additional proteins of interest may include, but are not limited to, interleukins, for example one or more than one of IL-1 to IL-24, IL-26 and IL-27, cytokines, Erythropoietin (EPO), insulin, G-CSF, GM-CSF, hPG-CSF, M-CSF or combinations thereof, interferons, for example, interferon-alpha, interferon-beta, interferon-gamma, blood clotting factors, for example, Factor VIII, Factor IX, or tPA hGH, receptors, receptor agonists, antibodies, neuropolypeptides, insulin, vaccines, growth factors for example but not limited to epidermal growth factor, keratinocyte growth factor, transformation growth factor, growth regulators, antigens, autoantigens, fragments thereof, or combinations thereof.

A non-limiting example of a protein suprastructure is an antibody. Antibodies are glycoproteins that have a molecular weight from about 100 to about 1000 kDa, or any amount therebetween. Antibodies comprise four polypeptide chains, two light chains and two heavy chains, which are connected by disulfide bonds. For example, which is not to be considered limiting, each light chain may have a molecular weight of approx. 25 kDa, for example from about 20 to about 30 kDa or any amount therebetween, or more for example from about 20 to about 300 kDa or any amount therebetween, and is composed of two domains, one variable domain ($V_L$) and one constant domain ($C_L$). Each heavy chain may have a molecular weight of approx. 50 kDa, for example from about 30 to about 75 kDa, or any amount therebetween, or more for example from about 30 to about 500 kDa or any amount therebetween, and consists of a constant and variable region. The heavy and light chains contain a number of homologous sections consisting of similar but not identical groups of amino acid sequences. These homologous units consist of about 110 amino acids and are called immunoglobulin domains. The heavy chain contains one variable domain ($V_H$) and either three or four constant domains ($C_H1$, $C_H2$, $C_H3$, and $C_H4$, depending on the antibody class or isotype). The region between the $C_H1$ and $C_H2$ domains is called the hinge region and permits flexibility between the two Fab arms of the Y-shaped antibody molecule, allowing them to open and close to accommodate binding to two antigenic determinants separated by a fixed distance.

Another non-limiting example of a protein suprastructure is a VLP. The VLP may comprise an HA0 precursor form, or the HA1 or HA2 domains retained together by disulphide bridges form. A VLP may have an average size of about 20 nm to 1 μm, or any amount therebetween, for example 60, 65, 70, 75, 80, 85, 90, 95, 100, 105, 110, 120, 130, 140, 150 160, 170, 180, 190, or 200 nm, or any amount therebetween, for example 100 nm, and may include a lipid membrane.

The proteins, or suprastructure proteins, may further comprise one or more lipids, phospholipids, nucleic acids, membranes or the like. Two or more polypeptides may be connected by a covalent bond, a disulfide bridge, charge interaction, hydrophobic attraction, van der waals forces, hydrogen bonds or the like. An example of a protein suprastructure is a monoclonal antibody, a chimeric monoclonal antibody, a single chain monoclonal antibody, or a virus like particle (VLP) which may be enveloped, or non-enveloped, for example, a viral envelope protein, a viral structural protein, a viral capsid protein, or a viral coat protein.

Proteins, or suprastructure proteins, may be produced in suitable host cells including plant host cells, and if desired further purified. While a chimeric monoclonal antibody, an influenza VLP, and chimeric influenza VLP are exemplified herein, the methods described herein may be used for any cytosolic plant-derived protein or suprastructure protein, or any plant-derived protein or suprastructure protein that localize in, or are secreted to, the apoplast.

The present invention also provides a method of preparing plant-derived proteins, or suprastructure proteins. The method involves obtaining a plant or plant matter comprising plant-derived proteins, or suprastructure proteins, localized within the apoplast; producing a protoplast/spheroplast fraction, and an apoplast fraction from the plant matter, the apoplast fraction comprising plant-derived proteins, or suprastructure proteins, and recovering the apoplast fraction. If desired, the plant derived proteins, or suprastructure proteins, may be purified from the apoplast fraction.

The present invention also provides a method of preparing a protein or suprastructure protein, wherein the protein or suprastructure protein comprises a plant derived lipid envelope, for example a VLP comprising a plant-derived lipid envelope. The method includes obtaining a plant, or plant matter comprising the suprastructure protein of interest, for example the VLP, treating the plant or plant matter with an enzyme composition to produce one or more than one apoplastic protein complex and a protoplast/spheroplast fraction, and separating the one or more than one apoplastic protein complex from the protoplast fraction. The one or more than one apoplastic protein complex comprises the suprastructure protein or VLP comprising a plant derived lipid envelope.

The present invention also provides a method of preparing plant derived proteins, or suprastructure proteins, comprising obtaining a plant or plant matter that comprise the plant-derived proteins, or suprastructure proteins, digesting the plant matter using a cell wall degrading enzyme composition to produced a digested fraction, and filtering the digested fraction to produced a filtered fraction and recovering the plant-derived proteins, or suprastructure proteins, from the filtered fraction. In this method, integrity of the protoplasts may not be required.

A protoplast is a plant cell that has had its cell wall completely or partially removed. A spheroplast may have partial removal of the cell wall. A protoplast, a spheroplast, or both a protoplast and spheroplast (protoplast/spheroplast) may be used as described herein, and the terms as used herein are interchangeable. The cell wall may be disrupted and removed mechanically (e.g. via homogenization, blending), the cell wall may be fully or partially digested enzymatically, or the cell wall may be removed using a combination of mechanical and enzymatic methods, for example homogenization followed by treatment with enzymes for digestion of the cell wall. Protoplasts may also be obtained from cultured plant cells, for example liquid cultured plant cells, or solid cultured plant cells.

Standard reference works setting forth the general principles of plant tissue culture, cultured plant cells, and production of protoplasts, spheroplasts and the like include: *Introduction to Plant Tissue Culture*, by M K Razdan 2$^{nd}$ Ed. (Science Publishers, 2003; which is incorporated herein by reference), or see for example, the following URL: molecular-plant-biotechnology.info/plant-tissue-culture/protoplast-isolation.htm. Methods and techniques relating to protoplast (or spheroplast) production and manipulation are reviewed in, for example, Davey M R et al., 2005 (Biotechnology Advances 23:131-171; which is incorporated herein by reference). Standard reference works setting forth the general methods and principles of protein biochemistry, molecular biology and the like include, for example Ausubel et al, Current Protocols In Molecular Biology, John Wiley & Sons, New York (1998 and Supplements to 2001; which is incorporated herein by reference); Sambrook et al, Molecular Cloning: A Laboratory Manual, 2d Ed., Cold Spring Harbor Laboratory Press, Plainview, New York, 1989 (which is incorporated herein by reference); Kaufman et al, Eds., Handbook Of Molecular And Cellular Methods In Biology And Medicine, CRC Press, Boca Raton, 1995 (which is incorporated herein by reference); McPherson, Ed., Directed Mutagenesis: A Practical Approach, IRL Press, Oxford, 1991 (which is incorporated herein by reference).

Enzymes useful for digesting or degrading plant cell walls for release or protoplasts or spheroplasts are known to one of skill in the art and may include cellulase (EC 3.2.1.4), pectinase (EC 3.2.1.15), xylanase (EC 3.2.1.8), chitinases (EC 3.2.1.14), hemicellulase, or a combination thereof. Non-limiting examples of suitable enzymes includes a multi-component enzyme mixture comprising cellulase, hemicellulase, and pectinase, for example MACEROZYME™ (containing approximately: Cellulase: 0.1 U/mg, Hemicellulase: 0.25 U/mg, and Pectinase: 0.5 U/mg). Other examples of commercial enzymes, enzyme mixtures and suppliers are listed in Table 1 (see: *Introduction to Plant Tissue Culture, by MK Razdan* 2$^{nd}$ Ed., Science Publishers, 2003).

Alternate names, and types of cellulases include endo-1, 4-β-D-glucanase; β-1,4-glucanase; β-1,4-endoglucan hydrolase; cellulase A; cellulosin AP; endoglucanase D; alkali cellulase; cellulase A 3; celludextrinase; 9.5 cellulase; avicelase; pancellase SS and 1,4-(1,3;1,4)-β-D-glucan 4-glucanohydrolase. Alternate names, and types of pectinases (polygalacturonases) include pectin depolymerase; pectinase; endopolygalacturonase; pectolase; pectin hydrolase; pectin polygalacturonase; endo-polygalacturonase; poly-α-1,4-galacturonide glycanohydrolase; endogalacturonase; endo-D-galacturonase and poly(1,4-α-D-galacturonide) glycanohydrolase. Alternate names, and types of xylanases include hemicellulase, endo-(1→4)-β-xylan 4-xylanohydrolase; endo-1,4-xylanase; xylanase; β-1,4-xylanase; endo-1,4-xylanase; endo-β-1,4-xylanase; endo-1,4-β-D-xylanase; 1,4-β-xylan xylanohydrolase; β-xylanase; β-1,4-xylan xylanohydrolase; endo-1,4-β-xylanase; 3-D-xylanase. Alternate names, and types of chitinases include chitodextrinase; 1,4-β-poly-N-acetylglucosaminidase; poly-β-glucosaminidase; β-1,4-poly-N-acetyl glucosamidinase; poly[1,4-(N-acetyl-β-D-glucosaminide)] glycanohydrolase.

TABLE 1

Non-limiting examples of commercially available enzymes for protoplast isolation

| Enzyme | Source | Supplier |
|---|---|---|
| Cellulases | | |
| Cellulase ONOZUKA R-10 | *Trichoderma viride* | Kinki Yakult Mfg. Col. Ltd. 8-12, Shinglkancho Nishinomiya, Japan |
| Cellulase ONOZUKA RS | *T. viride* | Yakult Honsha Co., Tokyo, Japan |
| Cellulase YC | *T. viride* | Seishin Pharma Co. Ltd. 9-500-1, Nagareyama Nagareyama-shi, Chiba-kan, Japan |
| Cellulase CEL | *T. viride* | Cooper Biomedical Inc. Malvern, PA, USA |
| Cellulysin | *T. viride* | Calbiochem, San Diego, CA, USA |
| Driselase | *Irpex locteus* | Kyowa Hakko Kogyo Co. Ltd., Tokyo, Japan |
| Melcelase P-1 | *T. viride* | Meiji Seiki Kaisha Ltd. No. 8, 2-Chome Kyobashi, Chou-Ku, Japan |
| Multifect CX GC | *T. viride* | Genencor |
| Multifect CX B | *T. viride* | Genencor |
| Hemicellulases | | |
| Hellcase | *Helix pomatia* | Industrie Biologique Francaise, Gennevilliers, France |
| Hemicellulase | *Aspergillus niger* | Sigma Chemical Co., St. Louis, MO, USA |
| Hemicellulase H-2125 | *Rhizopus* sp. | Sigma, Munchen |
| Rhozyme HP 150 | *Aspergillus niger* | Genencor Inc., South San Francisco, CA, USA |
| Pectinases | | |
| MACERASE | *Rhizopus arrhizus* | Calbiochem, San Diego, CA, USA |
| MACEROZYME R-10 | *R. arrhizus* | Yakult Honsha Co., Tokyo, Japan |
| Multifect Pectinase FE | *A. niger* | Genencor |
| PATE | *Bacillus polymyza* | Farbwerke-Hoechst AG, Frankfurt, FRG |

TABLE 1-continued

Non-limiting examples of commercially available enzymes for protoplast isolation

| Enzyme | Source | Supplier |
|---|---|---|
| Pectinol | *Aspergillus* sp. | Rohm and Haas Co. Independence Hall West, Philadelphia, PA 19105, USA |
| Pectolyase Y-23 | *Aspergillus joponicus* | Seishin Pharma Co. Ltd., Japan |
| Zymolyase | *Arthrobacter luteus* | Sigma Chemical Co., USA |

Choice of a particular enzyme or combination of enzymes, and concentration and reaction conditions may depend on the type of plant tissue used from which the protoplast and apoplast fraction comprising the VLPs is obtained. A mixture of cellulase, hemicellulase and pectinase, for example, a pectinase MACEROZYME™ or Multifect, may be used in a concentration ranging from 0.01% to 2.5% (v/v), for example 0.01, 0.02, 0.04, 0.06, 0.08, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, or 2.5% (v/v), or any amount therebetween. MACEROZYME™ or Multifect may be used alone, or in combination with other enzymes, e.g cellulase, pectinase, hemicellulase, or a combination thereof. Cellulase may be used in a concentration ranging from 0.1% to 5%, for example 0.1, 0.25, 0.5, 0.75, 1.0, 1.25, 1.5, 1.75, 2.0, 2.25, 2.5, 2.75. 3.0. 3.25, 3.5, 3.75, 4.0, 4.25, 4.5, 4.75, 5.0% (w/v) or any amount therebetween.

The enzyme solution (alternately referred to as a cell wall degrading composition, digesting solution) will generally comprise a buffer or buffer system, an osmoticum, and one or more than one salts, divalent cations or other additives. The buffer or buffer system is selected to maintain a pH in the range suitable for enzyme activity and the stability of the protein(s), or VLP, to purify, for example, within the range of about pH 5.0 to about 8.0, or any value therebetween. The selected pH used may vary depending upon the VLP to be recovered, for example the pH may be 5.0, 5.2, 5.4, 5.6, 5.8, 6.0, 6.2, 6.4, 6.6, 6.8, 7.0, 7.2, 7.4, 7.6, 7.8, 8.0, or any pH therebetween. Examples of buffers or buffer systems include, but are not limited to, MES, phosphate, citrate and the like. One or more buffers or buffer systems may be combined in an enzyme solution (digesting solution); the one or more buffers may be present at a concentration from 0 mM to about 200 mM, or any amount therebetween, for example 10, 20, 30, 40, 50, 60, 70, 80, 90, 100, 110, 120, 130, 140, 150, 160, 170, 180 or 190 mM or any amount therebetween. Depending on the suitability, an osmoticum component can be added if desired. The osmoticum and its concentration are selected to raise the osmotic strength of the enzyme solution. Examples of osmoticum include mannitol, sorbitol or other sugar alcohols, polyethylene glycol (PEG) of varying polymer lengths, and the like. Concentration ranges of osmoticum may vary depending on the plant species, the type of osmoticum used, and the type of plant tissue selected (species or organ of origin e.g. leaf or stem)—generally the range is from 0M to about 0.8 M, for example 0.05, 0.1, 0.15, 0.2, 0.25, 0.3. 0.35, 0.4, 0.5, 0.6, 0.7, or 0.75 M, or any amount therebetween, for example, 0, 50, 100, 150, 200, 250, 300, 350, 400, 450, 500, 550, 600 nM mannitol, or any amount therebetween. The concentration of osmoticum may also be expressed as a percentage (w/v). For some plant or tissue types, it may be beneficial to employ a slightly hypertonic preparation, which may facilitate separation of plant cell plasma membrane from the cell wall. The osmoticum can also be omitted during digestion.

Another parameter to set for the plant digestion is the temperature. Temperature may be controlled if desired during the digestion process. Useful temperature range should be between 4° C. and 40° C. or any temperature therebetween, for example from about 4° C. to about 15° C., or any amount therebetween, or from about 4° C. to about 22° C., or any temperature therebetween. Depending to the temperature chosen, the other digestion experimental parameters may be adjusted to maintain optimal extraction conditions.

Cations, salts or both may be added to improve plasma membrane stability, for example divalent cations, such as $Ca^{2+}$, or $Mg^{2+}$, at 0.5-50 mM, or any amount therebetween, salts, for example $CaCl_2$, NaCl, $CuSO_4$, $KNO_3$, and the like, from about 0 to about 750 mM, or any amount therebetween, for example 10, 20, 30, 40, 50, 100, 200, 300, 400, 500, 600, 700 or 750 mM. Other additives may also be added including a chelator for example, but not limited to, EDTA, EGTA, from about 0 to about 200 mM, or any amount therebetween, for example 5, 10, 15, 20, 25, 50, 75, 100, 125, 150, 175, 200 mM, or any amount therebetween, a reducing agent to prevent oxidation such as, but not limited to, sodium bisulfite or ascorbic acid, at 0.005-0.4% or any amount therebetween, for example 0.01, 0.02, 0.03, 0.04, 0.05, 0.06, 0.07, 0.08, 0.09, 0.1, 0.15, 0.2, 0.25, 0.3, 0.35, 0.4%, or any amount therebetween, specific enzyme inhibitors (see below), and if desired, an inhibitor of foliar senescence, for example, cycloheximide, kinetin, or one or more polyamines.

The digestion solution may also comprise one or more of mannitol from about 0 to about 600 mM, NaCl from about 0 to about 500 mM, EDTA from about 0 to about 50 mM, cellulase from about 1% to about 2% v/v, pectinase from about 0 to about 1% v/v, sodium metabisulfite from about 0.03 to about 0.04%, citrate from about 0 to about 125 mM or NaPO4 from about 0 to 75 mM.

The plant matter may be treated to enhance access of the enzymes or enzyme composition to the plant cell wall. For example, the epidermis of the leaf may be removed or 'peeled' before treatment with an enzyme composition. The plant matter may be cut into small pieces (manually, or with a shredding or cutting device such as an Urschel slicer); the cut up plant matter may be further infiltrated with an enzyme composition under a partial vacuum (Nishimura and Beevers 1978, Plant Physiol 62:40-43; Newell et al., 1998, J. Exp Botany 49:817-827). Mechanical perturbation of the plant matter may also be applied to the plant tissues (Giridhar et al., 1989. Protoplasma 151:151-157) before or during treatment with an enzyme composition. Furthermore, cultured plant cells, either liquid or solid cultures, may be used to prepare protoplasts or spheroplasts.

It may be desired to use an enzyme composition that lacks, or that has inactivated lipases or proteases. In some embodiments, one or more protease, or lipase inhibitors may be included in the enzyme composition. Examples of lipase inhibitors include RHC80267 (SigmaAldrich); examples of protease inhibitors include E-64, $Na_2EDTA$, Pepstatin, aprotinin, PMSF, Pefabloc, Leupeptin, bestatin and the like.

Any suitable method of mixing or agitating the plant matter in the enzyme composition may be used. For example, the plant matter may be gently swirled or shaken in a tray or pan or via a rotary shaker, tumbled in a rotating or oscillating drum. Precaution should be taken in order to minimize the protoplast (and/or spheroplast) damage until they are removed form the digestion soup. The digestion vessel should be selected accordingly.

As a non-limiting example, an enzyme composition comprising 1.5% cellulase (Onozuka R-10) and 0.375% MACEROZYME™ in 500 mM mannitol, 10 m $CaCl_2$ and 5 mM MES (pH 5.6) may be used for protoplast (or spheroplast) production from some Nicotiana tissues. As described herein, the concentration of mannitol may also be varied from about 0 to about 500 mM, or any amount therebetween. One of skill in the art, provided with the information disclosed herein, will be able to determine a suitable enzyme composition for the age and strain of the Nicotiana sp, or for another species used for production of VLPs.

Upon disruption of the cell wall, or partial digestion of the cell wall, a protoplast fraction (comprising protoplasts and/or spheroplasts), and an "apoplast fraction" are obtained. Alternatively, a "digested fraction" may be obtained. As noted below, integrity of the protoplast fraction may not be required to produce high yields of protein as described herein, therefore, an apoplast fraction or a digested fraction may be used for the extraction of proteins, for example, but not limited to, VLPs, viral envelope proteins, viral structural proteins, viral capsid proteins, viral coat proteins.

By "apoplast fraction" it is meant a fraction that is obtained following enzymatic digestion, or partial enzymatic digestion, using cell wall degrading enzymes of the plant matter in the presence of an osmoticum and/or other ingredients that may be used to assist in maintaining integrity of the protoplast. The apoplast fraction may comprise some components arising from disrupted protoplasts (or spheroplasts). For example, the apoplast fraction may comprise from about 0 to about 50% (v/v) or any amount therebetween, of the components from the protoplast fraction, or 0, 0.1, 0.5, 1, 5, 10, 15, 20, 25, 30, 35, 40, 45, or 50% (v/v) or any amount therebetween of the components from the protoplast fraction.

By a "digested fraction" it is meant the fraction that remains following enzymatic digestion, or partial enzymatic digestion, using cell wall degrading enzymes of the plant matter, however, integrity of the protoplast is not required, and the digested fraction may comprise intact, disrupted, or both intact and disrupted protoplasts. The composition comprising the cell wall degrading enzymes used to produce the digested fraction may comprise an osmoticum, or the osmoticum may be present at a reduced amount when compared to the amount present in standard procedures used to obtain protoplasts, or the osmoticum may be absent from the composition. The digested fraction comprises the apoplast fraction and the protoplast/spheroplast fraction, however, the protoplast/spheroplast fraction may or may not be intact. The digested fraction contains intracellular components and extracellular components. Intracellular components may be found in the form of protoplasts/spheroplasts if an osmoticum is used to maintain the protoplast/spheroplast intact. If no osmoticum is used in the digestion solution, then the protoplasts/spheroplasts may be disrupted and the intracellular and extracellular components may be combined in the digested fraction. As described herein, the proteins of interest, or protein suprastructures of interest, may be separated from components of the digested fraction using any suitable technique. Without wishing to be bound by theory, the step of cell wall digestion may loosen the polymeric components of the cells wall and assist in release of the proteins, or suprastructure proteins, otherwise trapped within the cell wall. This protocol also minimizes contamination of the proteins, or suprastructure proteins, with the intracellular components. The proteins or suprastructure proteins of interest may be separated from cellular debris following enzymatic digestion using low speed centrifugation followed by filtration, depth filtration, sedimentation, precipitation for example, but not limited to ammonium sulfate precipitation, or a combination thereof to obtain a separated fraction comprising the proteins or suprastructure proteins of interest.

If an osmoticum is used, the protoplast/spheroplast fraction, or fraction comprising protoplasts, may be separated from the apoplast fraction using any suitable technique, for example but not limited to, centrifugation, filtration, depth filtration, sedimentation, precipitation, or a combination thereof to obtain a separated fraction comprising the proteins or suprastructure proteins of interest and/or comprising protoplasts/spheroplasts that comprise the proteins or suprastructure proteins of interest.

The separated fraction may be for example a supernatant (if centrifuged, sedimented, or precipitated), or a filtrate (if filtered), and is enriched for proteins, or suprastructure proteins. The separated fraction may be further processed to isolate, purify, concentrate or a combination thereof, the proteins, or suprastructure proteins, by, for example, additional centrifugation steps, precipitation, chromatographic steps (e.g. size exclusion, ion exchange, affinity chromatography), tangential flow filtration, or a combination thereof. The presence of purified proteins, or suprastructure proteins, may be confirmed by, for example, native or SDS-PAGE, Western analysis using an appropriate detection antibody, capillary electrophoresis, or any other method as would be evident to one of skill in the art.

The apoplast is the portion of the plant cell outside the plasma membrane, and includes the cell wall and intercellular spaces of the plant. While it is preferred that the integrity of the protoplasts (and/or spheroplasts) be maintained during digestion and further processing, it is not required that the protoplasts remain intact in order to enrich for proteins, or suprastructure proteins.

During synthesis, proteins, or suprastructure proteins, may be secreted outside of the plasma membrane. If the suprastructure protein is a VLP, they are of an average size of about 20 nm to 1 μm, or any amount therebetween. If the suprastructure protein is an antibody, they are of a molecular weight from about 100 kDa to about 1000 kDa, or any amount therebetween. Due to their size, once synthesized, proteins, or suprastructure proteins, may remain trapped between the plasma membrane and cell wall and may be inaccessible for isolation or further purification using standard mechanical methods used to obtain plant proteins. In order to maximize yields, minimize contamination of the suprastructure protein fraction with cellular proteins, maintain the integrity of the proteins, or suprastructure proteins, and, where required, the associated lipid envelope or membrane, methods of disrupting the cell wall to release the proteins, or suprastructure proteins, that minimize mechanical damage to the protoplast and/or spheroplasts may be useful, such as the enzymatic methods described herein. However, it is not required that the integrity of all of the protoplasts be retained during the procedure.

A suprastructure protein, for example, a VLP produced in a plant may be complexed with plant-derived lipids. The plant-derived lipids may be in the form of a lipid bilayer, and may further comprise an envelope surrounding the VLP. The plant derived lipids may comprise lipid components of the plasma membrane of the plant where the VLP is produced, including, but not limited to, phosphatidylcholine (PC), phosphatidylethanolamine (PE), glycosphingolipids, phytosterols or a combination thereof. A plant-derived lipid may alternately be referred to as a 'plant lipid'. Examples of phytosterols are known in the art, and include, for example, stigmasterol, sitosterol, 24-methylcholesterol and cholesterol (Mongrand et al., 2004, J. Biol Chem 279:36277-86).

Polypeptide expression may be targeted to any intracellular or extracellular space, organelle or tissue of a plant as desired. In order to localize the expressed polypeptide to a particular location, the nucleic acid encoding the polypeptide may be linked to a nucleic acid sequence encoding a signal peptide or leader sequence. A signal peptide may alternately be referred to as a transit peptide, signal sequence, or leader sequence. Signal peptides or peptide sequences for directing localization of an expressed polypeptide to the apoplast include, but are not limited to, a native (with respect to the protein) signal or leader sequence, or a heterologous signal sequence, for example but not limited to, a rice amylase signal peptide (McCormick 1999, Proc Natl Acad Sci USA 96:703-708), a protein disulfide isomerase signal peptide (PDI) having the amino acid sequence:

```
MAKNVAIFGLLFSLLLLVPSQIFAEE;,    SEQ ID NO. 10
``` a plant pathogenesis related protein (PRP; Szyperski et al. PNAS 95:2262-2262), for example, Tobacco plant pathogenesis related protein 2 (PRP), a human monoclonal antibody signal peptide (SP, or leader sequence), or any signal peptide that is native with respect to the protein.

In some examples, an expressed polypeptide may accumulate in specific intercellular or extracellular space (such as the apoplast), organelle or tissue, for example when the polypeptide is expressed and secreted in the absence of a signal peptide or transit peptide.

The term "virus like particle" (VLP), or "virus-like particles" or "VLPs" refers to structures that self-assemble and comprise viral surface proteins, for example an influenza HA protein, or a chimeric influenza HA protein. VLPs and chimeric VLPs are generally morphologically and antigenically similar to virions produced in an infection, but lack genetic information sufficient to replicate and thus are non-infectious.

By "chimeric protein" or "chimeric polypeptide", it is meant a protein or polypeptide that comprises amino acid sequences from two or more than two sources, for example but not limited to, two or more influenza types or subtypes, that are fused as a single polypeptide. The chimeric protein or polypeptide may include a signal peptide that is the same (i.e. native) as, or heterologous with, the remainder of the chimeric protein or protein. The chimeric protein or chimeric polypeptide may be produced as a transcript from a chimeric nucleotide sequence, and remain intact, or if required, the chimeric protein or chimeric polypeptide may be cleaved following synthesis. The intact chimeric protein, or cleaved portions of the chimeric protein, may associate to form a multimeric protein. A chimeric protein or a chimeric polypeptide may also include a protein or polypeptide comprising subunits that are associated via disulphide bridges (i.e. a multimeric protein). For example, a chimeric polypeptide comprising amino acid sequences from two or more than two sources may be processed into subunits, and the subunits associated via disulphide bridges to produce a chimeric protein or chimeric polypeptide. A non-limiting example a chimeric protein is a chimeric monoclonal antibody, for example C2B8, or a chimeric VLP, for example but not limited to proteins and VLPs produced constructs numbered 690, 691, 696, 734, 737, 745 or 747 (Table 2) as described in U.S. provisional application U.S. 61/220,161 and PCT/CA2010/000983 (which are incorporated herein by reference).

The protein or suprastructure protein maybe a glycoprotein, and the method as described herein involving extraction by cell wall digestion can be applied to plants co-expressing a glycoprotein and one or more enzymes for modifying N-glycosylation profile as described in WO 20008/151440 (Modifying glycoprotein production in plants; which is incorporated herein by reference) for favoring the recovery of glycoproteins bearing modified mature N-glycans. For example, mature N-glycans could be exempt of xylose and fucose residues, or exhibit reduced fucosylated, xylosylated, or both, fucosylated and xylosylated, N-glycans. Alternatively, a protein of interest comprising a modified glycosylation pattern may be obtained, wherein the protein lacks fucosylation, xylosylation, or both, and comprises increased galactosylation.

The modified N-glycosylation profile may be obtained by co-expressing within a plant, a portion of a plant, or a plant cell, a nucleotide sequence encoding a first nucleotide sequence encoding a hybrid protein (GNT1-GalT), comprising a CTS domain (i.e. the cytoplasmic tail, transmembrane domain, stem region) of N-acetylglucosaminyl transferase (GNT1) fused to a catalytic domain of beta-1,4-galactosyl-transferase (GalT), the first nucleotide sequence operatively linked with a first regulatory region that is active in the plant, and a second nucleotide sequence for encoding the suprastructure protein of interest, the second nucleotide sequence operatively linked with a second regulatory region that is active in the plant, and co-expressing the first and second nucleotide sequences to synthesize a suprastructure protein of interest comprising glycans with the modified N-glycosylation profile, as described in WO 20008/151440.

The suprastructure protein may be influenza hemagglutinin (HA), and each of the two or more than two amino acid sequences that make up the polypeptide may be obtained from different HA's to produce a chimeric HA, or chimeric influenza HA. A chimeric HA may also include a amino acid sequence comprising heterologous signal peptide (a chimeric HA pre-protein) that is cleaved after synthesis. Examples of HA proteins that may be used in the invention described herein may be found in WO 2009/009876; WO 2009/076778; WO 2010/003225 (which are incorporated herein by reference). A nucleic acid encoding a chimeric polypeptide may be described as a "chimeric nucleic acid", or a "chimeric nucleotide sequence". A virus-like particle comprised of chimeric HA may be described as a "chimeric VLP". Chimeric VLPs are further described in PCT Application No. PCT/CA2010/000983 filed Jun. 25, 2010, and U.S. Provisional Application No. 61/220,161 (filed Jun. 24, 2009; which is incorporated herein by reference). VLPs can be obtained from expression of native or chimeric HA.

The HA of the VLPs prepared according to a method provided by the present invention, include known sequences and variant HA sequences that may be developed or identified. Furthermore, VLPs produced as described herein do not comprise neuraminidase (NA) or other components for example M1 (M protein), M2, NS and the like. However, NA and M1 may be co-expressed with HA should VLPs comprising HA and NA be desired.

Generally, the term "lipid" refers to a fat-soluble (lipophilic), naturally-occurring molecules. A chimeric VLP produced in a plant according to some aspects of the invention may be complexed with plant-derived lipids. The plant-derived lipids may be in the form of a lipid bilayer, and may further comprise an envelope surrounding the VLP. The plant derived lipids may comprise lipid components of the plasma membrane of the plant where the VLP is produced, including phospholipids, tri-, di- and monoglycerides, as well as fat-soluble sterol or metabolites comprising sterols. Examples include phosphatidylcholine (PC), phosphatidylethanolamine (PE), phosphatidylinositol, phosphatidylserine, glycosphingolipids, phytosterols or a combination thereof. A plant-derived lipid may alternately be referred to as a 'plant lipid'. Examples of phytosterols include campesterol, stigmasterol, ergosterol, brassicasterol, delta-7-stigmasterol, delta-7-avenasterol, daunosterol, sitosterol, 24-methylcholesterol, cholesterol or beta-sitosterol (Mongrand et al., 2004, J. Biol Chem 279:36277-86). As one of skill in the art will readily understand, the lipid composition of the plasma membrane of a cell may vary with the culture or growth conditions of the cell or organism, or species, from which the cell is obtained.

Cell membranes generally comprise lipid bilayers, as well as proteins for various functions. Localized concentrations of particular lipids may be found in the lipid bilayer, referred to as 'lipid rafts'. These lipid raft microdomains may be enriched in sphingolipids and sterols. Without wishing to be bound by theory, lipid rafts may have significant roles in endo and exocytosis, entry or egress of viruses or other infectious agents, inter-cell signal transduction, interaction with other structural components of the cell or organism, such as intracellular and extracellular matrices.

VLPs comprising a lipid envelope has been previously described in WO 2009/009876; WO 2009/076778, and WO 2010/003225 (which are incorporated herein by reference). With reference to influenza virus, the term "hemagglutinin" or "HA" as used herein refers to a structural glycoprotein of influenza viral particles. The HA of the present invention may be obtained from any subtype. For example, the HA may be of subtype H1, H2, H3, H4, H5, H6, H7, H8, H9, H10, H11, H12, H13, H14, H15, or H16, or of influenza types B or C. The recombinant HA of the present invention may also comprise an amino acid sequence based on the sequence of any hemagglutinin. The structure of influenza hemagglutinin is well-studied and demonstrates a high degree of conservation in secondary, tertiary and quaternary structure. This structural conservation is observed even though the amino acid sequence may vary (see, for example, Skehel and Wiley, 2000 Ann Rev Biochem 69:531-69; Vaccaro et al 2005; which is incorporated herein by reference). Nucleotide sequences encoding HA are well known, and are available for example, from the BioDefense and Public Health Database (now Influenza Research Database; Squires et al., 2008 Nucleic Acids Research 36:D497-D503) for example at URL: biohealthbase.org/GSearch/home.do?decorator=Influenza) or the databases maintained by the National Center for Biotechnology Information (NCBI; for example at URL: ncbi.nlm.nih.gov/sites/entrez?db=nuccore&cmd=search&term=influenza), both of which are incorporated herein by reference.

The present invention also pertains to methods of preparing, isolating, or both preparing and isolating VLPs, including influenza VLPs of viruses which infect humans, or host animals, for example primates, horses, pigs, birds, sheep, avian water fowl, migratory birds, quail, duck, geese, poultry, chicken, camel, canine, dogs, feline, cats, tiger, leopard, civet, mink, stone marten, ferrets, house pets, livestock, mice, rats, seal, whale and the like. Some influenza viruses may infect more than one host animal. Amino acid variation is tolerated in hemagglutinins of influenza viruses. This variation provides for new strains that are continually being identified. Infectivity between the new strains may vary. However, formation of hemagglutinin trimers, which subsequently form VLPs is maintained. The present invention also includes methods of preparing any plant-derived VLPs, regardless of the HA subtype or sequence, or chimeric HA comprising the VLP, or species of origin.

Correct folding of the suprastructure protein may be important for stability of the protein, formation of multimers, formation and function of the protein. Folding of a protein may be influenced by one or more factors, including, but not limited to, the sequence of the protein, the relative abundance of the protein, the degree of intracellular crowding, the availability of cofactors that may bind or be transiently associated with the folded, partially folded or unfolded protein, the presence of one or more chaperone proteins, or the like.

Heat shock proteins (Hsp) or stress proteins are examples of chaperone proteins, which may participate in various cellular processes including protein synthesis, intracellular trafficking, prevention of misfolding, prevention of protein aggregation, assembly and disassembly of protein complexes, protein folding, and protein disaggregation. Examples of such chaperone proteins include, but are not limited to, Hsp60, Hsp65, Hsp 70, Hsp90, Hsp100, Hsp20-30, Hsp10, Hsp100-200, Hsp100, Hsp90, Lon, TF55, FKBPs, cyclophilins, ClpP, GrpE, ubiquitin, calnexin, and protein disulfide isomerases (see, for example, Macario, A. J. L., Cold Spring Harbor Laboratory Res. 25:59-70. 1995; Parsell, D. A. & Lindquist, S. Ann. Rev. Genet. 27:437-496 (1993); U.S. Pat. No. 5,232,833). Chaperone proteins, for example but not limited to Hsp40 and Hsp70 may be used to ensure folding of a chimeric HA (PCT Application No. PCT/CA2010/000983 filed Jun. 25, 2010, and U.S. Provisional Application No. 61/220,161, filed Jun. 24, 2009; WO 2009/009876 and WO 2009/076778, all of which are incorporated herein by reference). Protein disulfide isomerase (PDI; Accession No. Z11499) may also be used.

Once recovered, proteins, or suprastructure proteins, may be assessed for structure, size potency or activity by, for example but not limited to, electron microscopy, light scattering, size exclusion chromatography, HPLC, Western blot analysis, electrophoresis, ELISA, activity based assays, e.g. hemagglutination assay, or any other suitable assay. These and other methods for assessing size, concentration, activity and composition of VLPs are known in the art.

For preparative size exclusion chromatography, a preparation comprising proteins, or suprastructure proteins, may be obtained by the methods described herein, and insoluble material removed by centrifugation. Precipitation with PEG or ammonium sulphate may also be of benefit. The recovered protein may be quantified using conventional methods (for example, Bradford Assay, BCA), and the extract passed through a size exclusion column, using for example SEPHACRYL™, SEPHADEX™, or similar medium, chromatography using an ion exchange column, or chromatography using an affinity column, and the active fractions collected. Protein complexes may also be obtained using affinity based magnetic separation for example, with Dynabeads™ (Invitrogen), and eluting the protein complex from the Dynabeads™. A combination of chromatographic and separation protocols may also be used. Following chromatography, or separation, fractions may be further analyzed by protein electrophoresis, immunoblot, ELISA, activity based assays as desired, to confirm the presence of the suprastructure protein.

If the suprastructure protein is a VLP, then a hemagglutination assay may be used to assess the hemagglutinating activity of the VLP-containing fractions, using methods well-known in the art. Without wishing to be bound by theory, the capacity of HA to bind to RBC from different animals is driven by the affinity of HA for sialic acids α2,3 or α2,3 and the presence of these sialic acids on the surface of RBC. Equine and avian HA from influenza viruses agglutinate erythrocytes from all several species, including turkeys, chickens, ducks, guinea pigs, humans, sheep, horses and cows; whereas human HAs will bind to erythrocytes of turkey, chickens, ducks, guinea pigs, humans and sheep (Ito T. et al, 1997, Virology, 227:493-499; Medeiros R et al, 2001. Virology 289:74-85).

A hemagglutination inhibition (HI, or HAI) assay may also be used to demonstrate the efficacy of antibodies induced by a vaccine, or vaccine composition comprising chimeric HA or chimeric VLP can inhibit the agglutination of red blood cells (RBC) by recombinant HA. Hemagglutination inhibitory antibody titers of serum samples may be evaluated by microtiter HAI (Aymard et al 1973). Erythrocytes from any of several species may be used—e.g. horse, turkey, chicken or the like. This assay gives indirect information on assembly of the HA trimer on the surface of VLP, confirming the proper presentation of antigenic sites on HAs.

Cross-reactivity HAI titres may also be used to demonstrate the efficacy of an immune response to other strains of virus related to the vaccine subtype. For example, serum from a subject immunized with a vaccine composition comprising a chimeric hemagglutinin comprising an HDC of a first influenza type or subtype may be used in an HAI assay with a second strain of whole virus or virus particles, and the HAI titer determined.

The influenza VLPs prepared by methods of the present invention may be used in conjunction with an existing influenza vaccine, to supplement the vaccine, render it more efficacious, or to reduce the administration dosages necessary. As would be known to a person of skill in the art, the vaccine may be directed against one or more than one influenza virus. Examples of suitable vaccines include, but are not limited to, those commercially available from Sanofi-Pasteur, ID Biomedical, Merial, Sinovac, Chiron, Roche, MedImmune, GlaxoSmithKline, Novartis, Sanofi-Aventis, Serono, Shire Pharmaceuticals and the like. If desired, the VLPs of the present invention may be admixed with a suitable adjuvant as would be known to one of skill in the art. Furthermore, the VLP produced according to the present invention may be co-expressed with other protein components or reconstituted with other VLPs or influenza protein components, for example, neuraminidase (NA), M1, and M2. It can also be co-expressed or reconstituted with other VLP made of vaccinal proteins such as malaria antigens, HIV antigens, respiratory syncytial virus (RSV) antigens, and the like.

Methods for transformation, and regeneration of transgenic plants, plant cells, plant matter or seeds comprising proteins, or suprastructure proteins, are established in the art and known to one of skill in the art. The method of obtaining transformed and regenerated plants is not critical to the present invention.

By "transformation" it is meant the interspecific transfer of genetic information (nucleotide sequence) that is manifested genotypically, phenotypically or both. The interspecific transfer of genetic information from a chimeric construct to a host may be heritable (i.e. integrated within the genome of the host) and the transfer of genetic information considered stable, or the transfer may be transient and the transfer of genetic information is not inheritable.

By the term "plant matter", it is meant any material derived from a plant. Plant matter may comprise an entire plant, tissue, cells, or any fraction thereof. Further, plant matter may comprise intracellular plant components, extracellular plant components, liquid or solid extracts of plants, or a combination thereof. Further, plant matter may comprise plants, plant cells, tissue, a liquid extract, or a combination thereof, from plant leaves, stems, fruit, roots or a combination thereof. Plant matter may comprise a plant or portion thereof which has not been subjected to any processing steps. A portion of a plant may comprise plant matter. Plants or plant matter may be harvested or obtained by any method, for example, the whole plant may be used, or the leaves or other tissues specifically removed for use in the described methods. Transgenic plants expressing and secreting VLPs may also be used as a starting material for processing as described herein.

The constructs of the present invention can be introduced into plant cells using Ti plasmids, Ri plasmids, plant virus vectors, direct DNA transformation, micro-injection, electroporation, infiltration, and the like. For reviews of such techniques see for example Weissbach and Weissbach, *Methods for Plant Molecular Biology*, Academy Press, New York VIII, pp. 421-463 (1988); Geierson and Corey, *Plant Molecular Biology,* 2d Ed. (1988); and Miki and Iyer, Fundamentals of Gene Transfer in Plants. In *Plant Metabolism,* 2d Ed. D T. Dennis, D H Turpin, D D Lefebrve, D B Layzell (eds), Addison-Wesley, Langmans Ltd. London, pp. 561-579 (1997). Other methods include direct DNA uptake, the use of liposomes, electroporation, for example using protoplasts, micro-injection, microprojectiles or whiskers, and vacuum infiltration. See, for example, Bilang, et al. (Gene 100: 247-250 (1991), Scheid et al. (Mol. Gen. Genet. 228: 104-112, 1991), Guerche et al. (Plant Science 52: 111-116, 1987), Neuhause et al. (Theor. Appl Genet. 75: 30-36, 1987), Klein et al., Nature 327: 70-73 (1987); Howell et al. (Science 208: 1265, 1980), Horsch et al. (Science 227: 1229-1231, 1985), DeBlock et al., Plant Physiology 91: 694-701, 1989), Methods for Plant Molecular Biology (Weissbach and Weissbach, eds., Academic Press Inc., 1988), Methods in Plant Molecular Biology (Schuler and Zielinski, eds., Academic Press Inc., 1989), Liu and Lomonossoff (J. Virol Meth, 105:343-348, 2002), U.S. Pat. Nos. 4,945,050; 5,036,006; 5,100,792; 6,403,865; 5,625,136, (all of which are hereby incorporated by reference).

Transient expression methods may be used to express the constructs of the present invention (see Liu and Lomonossoff, 2002, Journal of Virological Methods, 105:343-348; which is incorporated herein by reference). Alternatively, a vacuum-based transient expression method, as described in PCT Publications WO 00/063400, WO 00/037663 (incorporated herein by reference) may be used. These methods may include, for example, but are not limited to, a method of Agro-inoculation or Agro-infiltration, however, other transient methods may also be used as noted above. With either Agro-inoculation or Agro-infiltration, a mixture of *Agrobacteria* comprising the desired nucleic acid enter the intercellular spaces of a tissue, for example the leaves, aerial portion of the plant (including stem, leaves and flower), other portion of the plant (stem, root, flower), or the whole plant. After crossing the epidermis the *Agrobacterium* infect and transfer t-DNA copies into the cells. The t-DNA is episomally transcribed and the mRNA translated, leading to the production of the protein of interest in infected cells, however, the passage of t-DNA inside the nucleus is transient.

The sequences described herein are summarized below.

| SEQ ID NO: | Description | Figure |
|---|---|---|
| 1 | Nucleic acid sequence (construct 685) | 2A |
| 2 | Amino acid sequence encoded by SEQ ID NO: 1 | 2B |
| 3 | pBinPlus.2613c: AGGAAGGGAAGAAAGCGAAAGGAG | |
| 4 | Mut-ATG115.r: GTGCCGAAGCACGATCTGACAACGT TGAAGATCGCTCACGCAAGAAAGACAAGAGA | |
| 5 | Mut-ATG161.c: GTTGTCAGATCGTGCTTCGGCACCAGTACAA CGTTTTCTTTCACTGAAGCGA | |
| 6 | LC-05-1.110r: TCTCCTGGAGTCACAGACAGGGTGG | |
| 7 | ApaI-H5 (A-Indo).1c: TGTCGGGCCCATGGAGAAAATAGTGC TTCTTCTTGCAAT | |
| 8 | H5 (A-Indo)-StuI.1707r: AAATAGGCCTTTAAATGCAAATTC | |

| SEQ ID NO: | Description | Figure |
|---|---|---|
| | TGCATTGTAACGA | |
| 9 | nucleic acid sequence (construct 660) | 5 |
| 10 | PDI signal peptide: MAKNVAIFGLLFSLLLLVPSQIFAEE | |
| 11 | Plasto-443c | |
| 12 | supP19-plasto.r | |
| 13 | supP19-1c | |
| 14 | SupP19-SacI.r | |
| 15 | LC fragment of C2B8 | 9 |
| 16 | HC fragment of C2B8 | 10 |

The present invention will be further illustrated in the following examples. However it is to be understood that these examples are for illustrative purposes only, and should not be used to limit the scope of the present invention in any manner.

Assembly of Expression Cassettes

Constructs that may be used for the production of VLPs are described U.S. Provisional Application No. U.S. 61/220,161 and PCT/CA2010/000983 (which are incorporated herein by reference), WO 2009/009876, WO 2009/076778 and WO2010/003225 (all of which are incorporated herein by reference). Constructs may also include those listed in Table 2. Assembly of these constructs is described in WO 2009/009876, WO 2009/076778, WO2010/003225 and U.S. 61/220,161. However other constructs comprising known HA's, including but not limited to, those provided in Table 2, and combined with similar or different regulatory elements and promoters, may also be used for the production of VLPs as described herein.

TABLE 2

Non-limiting examples of constructs that can be used for hemagglutinin production.

| Cassette number | Corresponding HA | HA abbreviation |
|---|---|---|
| 540 | SpPDI-H1 from strain A/New Caledonia/20/99 (H1N1) | H1/NC |
| 560 | SpPDI-H1 A/California/4/2009 in 2X35S/CPMV-HT expression cassette | H1/Cal WT |
| 580 | SpPDI-H1 A/New Caledonia/20/99 in 2x35S/CPMV-HT expression cassette | H1/NC |
| 660 | H5 from strain A/Indonesia/5/2005 (H5N1) | H1/Indo |
| 663 | H5 A/Indonesia/5/2005 | H1/Indo |
| 685 | H5 A/Indonesia/5/2005 in CPMV-HT expression cassette | H1/Indo |
| 686 | SpPDI-H5 A/Indonesia/5/2005 in CPMV-HT expression cassette | H1/Indo |
| 690 | H1 A/Brisbane/59/07 receptor-binding (RB) domain in H5 A/Indonesia/5/05 backbone | H1/Bris |
| 691 | H1 A/Brisbane/59/07 esterase and receptor-binding domains (E1-RB-E2) in H5 A/Indonesia/5/05 backbone | H1/Bris |
| 696 | H5 A/Indonesia/5/05 receptor-binding (RB) domain in H1 A/New Caledonia/20/99 backbone | H1/Indo |
| 732 | H1 A/Brisbane/59/2007 in CPMV-HT expression cassette | H1/Bris |
| 733 | SpPDI-H1 A/Brisbane/59/2007 in CPMV-HT expression cassette | H1/Bris |
| 734 | H1 A/Brisbane/59/07 receptor-binding (RB) domain in H5 A/Indonesia/5/05 backbone in CPMV-HT expression cassette | H1/Bris |
| 735 | H3 A/Brisbane/10/2007 in CPMV-HT expression cassette | H3/Bris |

TABLE 2-continued

Non-limiting examples of constructs that can be used for hemagglutinin production.

| Cassette number | Corresponding HA | HA abbreviation |
|---|---|---|
| 736 | SpPDI-H3 A/Brisbane/10/2007 in CPMV-HT expression cassette | H3/Bris |
| 737 | Assembly of chimeric SpPDI-H3 A/Brisbane/10/2007 (ectodomain) + H5 A/Indonesia/5/2005 (TmD + Cyto tail) in CPMV-HT expression cassette | H3/Bris-H5/Indo chimera |
| 738 | HA B/Florida/4/2006 in CPMV-HT expression cassette | B/Flo |
| 739 | SpPDI-HA B/Florida/4/2006 in CPMV-HT expression cassette | B/Flo |
| 745 | SpPDI-HA B/Florida/4/2006 (ectodomain) + H5 A/Indonesia/5/2005 (TmD + Cyto tail) in CPMV-HT expression cassette | B/Flo |
| 747 | SpPDI-HA B/Florida/4/2006 + H5 A/Indonesia/5/2005 (TmD + Cyto tail) in 2X35S-CPMV-HT expression cassette | B/Flo |
| 774 | HA of A/Brisbane/59/2007 (H1N1) | H1/Bris |
| 775 | HA of A/Solomon Islands 3/2006 (H1N1) | H1/Solomon |
| 776 | HA of A/Brisbane 10/2007 (H3N2) | H3/Bris |
| 777 | HA of A/Wisconsin/67/2005 (H3N2) | H3/Wisc |
| 778 | HA of B/Malaysia/2506/2004 | B/Malaysia |
| 779 | HA of B/Florida/4/2006 | B/Flo |
| 780 | HA of A/Singapore/1/57 (H2N2) | H2/Sing |
| 781 | HA of A/Anhui/1/2005 (H5N1) | H5/Anhui |
| 782 | HA of A/Vietnam/1194/2004 (H5N1) | H5/Vietnam |
| 783 | HA of A/Teal/HongKong/W312/97 (H6N1) | H6/HongKong |
| 784 | HA of A/Equine/Prague/56 (H7N7) | H7/Prague |
| 785 | HA of A/HongKong/1073/99 (H9N2) | H9/HongKong |
| 787 | H1 A/Brisbane/59/2007 | H1/Bris |
| 790 | H3 A/Brisbane/10/2007 | H3/Bris |
| 798 | HA B/Florida/4/2006 | B/Flo |

CPMV-HT expression cassettes included the 35S promoter to control the expression of an mRNA comprising a coding sequence of interest flanked, in 5' by nucleotides 1-512 from the Cowpea mosaic virus (CPMV) RNA2 with mutated ATG at positions 115 and 161 and in 3', by nucleotides 3330-3481 from the CPMV RNA2 (corresponding to the 3' UTR) followed by the NOS terminator. Plasmid pBD-05-1LC, (Sainsbury et al. 2008; Plant Biotechnology Journal 6: 82-92 and PCT Publication WO 2007/135480), was used for the assembly of CPMV-HT-based hemagglutinin expression cassettes. The mutation of ATGs at position 115 and 161 of the CPMV RNA2 was done using a PCR-based ligation method presented in Darveau et al. (Methods in Neuroscience 26: 77-85 (1995)). Two separate PCRs were performed using pBD-05-1LC as template. The primers for the first amplification were pBinPlus.2613c (SEQ ID NO: 3) and Mut-ATG115.r (SEQ ID NO: 4). The primers for the second amplification were Mut-ATG161.c (SEQ ID NO: 5) and LC-05-1.110r (SEQ ID NO: 6). The two fragments were then mixed and used as template for a third amplification using pBinPlus.2613c (SEQ ID NO: 3) and LC-05-1.110r (SEQ ID NO: 6) as primers. The resulting fragment was digested with PacI and ApaI and cloned into pBD-05-1LC digested with the same enzyme. The expression cassette generated was named 828.

Assembly of H5 A/Indonesia/5/2005 in CPMV-HT Expression Cassette (Construct Number 685).

The assembly of this cassette is described in WO 2009/009876, WO 2009/076778 and WO2010/003325, which are incorporated herein by reference.

Briefly, the coding sequence of H5 from A/Indonesia/5/2005 was cloned into CPMV-HT as follows: restriction sites ApaI (immediately upstream of the initial ATG) and StuI (immediately downstream of a stop codon) were added to the hemagglutinin coding sequence by performing a PCR amplification with primers ApaI-H5 (A-Indo).1c (SEQ ID NO: 7) and H5 (A-Indo)-StuI.1707r (SEQ ID NO: 8) using construct number 660 (D'Aoust et al., Plant Biotechnology Journal 6:930-940 (2008)) as template. Construct 660 comprises an alfalfa plastocyanin promoter and 5' UTR, hemagglutinin coding sequence of H5 from A/Indonesia/5/2005 (Construct #660), alfalfa plastocyanin 3' UTR and terminator sequences (SEQ ID NO: 9; FIG. 5). The resulting fragment was digested with ApaI and StuI restriction enzymes and cloned into construct number 828, previously digested with the same enzymes. The resulting cassette was named construct number 685 (FIG. 1, 2).

Suppressors of Silencing.

Post-transcriptional gene silencing (PTGS) may be involved in limiting expression of transgenes in plants, and co-expression of a suppressor of silencing from the potato virus Y (HcPro) may be used to counteract the specific degradation of transgene mRNAs (Brigneti et al., 1998). Alternate suppressors of silencing are well known in the art and may be used as described herein (Chiba et al., 2006, Virology 346:7-14; which is incorporated herein by reference), for example but not limited to, TEV-p1/HC-Pro (Tobacco etch virus-p1/HC-Pro), BYV-p21, p19 of Tomato bushy stunt virus (TBSV p19), capsid protein of Tomato crinkle virus (TCV-CP), 2b of Cucumber mosaic virus; CMV-2b), p25 of Potato virus X (PVX-p25), p11 of Potato virus M (PVM-p11), p11 of Potato virus S (PVS-p11), p16 of Blueberry scorch virus, (BScV-p16), p23 of Citrus tristeza virus (CTV-p23), p24 of Grapevine leafroll-associated virus-2, (GLRaV-2 p24), p10 of Grapevine virus A, (GVA-p10), p14 of Grapevine virus B (GVB-p14), p10 of Heracleum latent virus (HLV-p10), or p16 of Garlic common latent virus (GCLV-p16). Therefore, a suppressor of silencing, for example, but not limited to, HcPro, TEV-p1/HC-Pro, BYV-p21, TBSV p19, TCV-CP, CMV-2b, PVX-p25, PVM-p11, PVS-p11, BScV-p16, CTV-p23, GLRaV-2 p24, GBV-p14, HLV-p10, GCLV-p16 or GVA-p10, may be co-expressed along with the nucleic acid sequence encoding the protein of interest to further ensure high levels of protein production within a plant.

The construction of p19 is described in described in WO 2010/0003225 (which is incorporated herein by reference). Briefly, the coding sequence of p19 protein of tomato bushy stunt virus (TBSV) was linked to the alfalfa plastocyanin expression cassette by the PCR-based ligation method presented in Darveau et al. (Methods in Neuroscience 26: 77-85 (1995)). In a first round of PCR, a segment of the plastocyanin promoter was amplified using primers Plasto-443c:

GTATTAGTAATTAGAATTTGGTGTC    (SEQ ID NO: 11)

and supP19-plasto.r (SEQ ID NO: 12)
CCTTGTATAGCTCGTTCCATTTTCTCTCAAGATG with construct 660 (described in WO 2010/0003225, which is incorporated herein by reference) as template. In parallel, another fragment containing the coding sequence of p19 was amplified with primers supP19-1c

ATGGAACGAGCTATACAAGG    (SEQ ID NO: 13)

and SupP19-SacI.r (SEQ ID NO: 14)
AGTCGAGCTCTTACTCGCTTTCTTTTTCGAAG using construct 35S:p19 as described in Voinnet et al. (The Plant Journal 33: 949-956 (2003)) as template. Amplification products were then mixed and used as template for a second round of amplification (assembling reaction) with primers Plasto-443c and SupP19-SacI.r. The resulting fragment was digested with BamHI (in the plastocyanin promoter) and SacI (at the end of the p19 coding sequence) and cloned into construct number 660, previously digested with the same restriction enzymes to give construct number R472. The plasmids were used to transform *Agrobacterium tumefaciens* (AGL1; ATCC, Manassas, VA 20108, USA) by electroporation (Mattanovich et al., 1989). The integrity of all *A. tumefaciens* strains were confirmed by restriction mapping. The *A. tumefaciens* strain comprising R472 (FIG. 11B) is termed "AGL1/R472".

HcPro construct (35HcPro) was prepared as described in Hamilton et al. (2002). All clones were sequenced to confirm the integrity of the constructs. The plasmids were used to transform *Agrobacterium tumefaciens* (AGL1; ATCC, Manassas, VA 20108, USA) by electroporation (Mattanovich et al., 1989). The integrity of all *A. tumefaciens* strains were confirmed by restriction mapping.

Preparation of Plant Biomass, Inoculum, Agroinfiltration, and Harvesting

*Nicotiana benthamiana* plants were grown from seeds in flats filled with a commercial peat moss substrate. The plants were allowed to grow in the greenhouse under a 16/8 photoperiod and a temperature regime of 25° C. day/20° C. night. Three weeks after seeding, individual plantlets were picked out, transplanted in pots and left to grow in the greenhouse for three additional weeks under the same environmental conditions. After six weeks, plants have an average weight of 80 g and 30 cm in height.

*Agrobacterium* strain AGL1 was transfected (electroporation) with constructs as identified below, using the methods described by D'Aoust et al 2008 (Plant Biotechnology Journal 6:930-940). Transfected *Agrobacterium* were grown in YEB medium supplemented with 10 mM 2-(N-morpholino)ethanesulfonic acid (MES), 20 μM acetosyringone, 50 μg/ml kanamycin and 25 μg/ml of carbenicillin pH5.6 to an $OD_{600}$ between 0.6 and 1.6. *Agrobacterium* suspensions were centrifuged before use and resuspended in infiltration medium (10 mM $MgCl_2$ and 10 mM MES pH 5.6).

Plants were agroinfiltrated as described in D'Aoust et al (supra). Briefly, for vacuum-infiltration, *A. tumefaciens* suspensions were centrifuged, resuspended in the infiltration medium and stored overnight at 4° C. On the day of infiltration, culture batches were diluted in 2.5 culture volumes and allowed to warm before use. Whole plants of *N. benthamiana* were placed upside down in the bacterial suspension in an air-tight stainless steel tank under a vacuum of 20-40 Torr for 2-min. Unless otherwise specified, all infiltrations were performed as co-infiltration with a bacterial transformed with R472 (strain AGL1/R472) at a 1:1 ratio. Following vacuum infiltration, plants were returned to the greenhouse for a 4-6 day incubation period until harvest.

Leaf Sampling and Total Protein Extraction (Mechanical Homogenization)

Following incubation of 4, 5, 6, 7 and 8 days, the aerial part of plants was harvested and used immediately. Total soluble proteins were extracted by homogenizing plant tissue in 3 volumes of cold 50 mM Tris pH 8.0, 0.15 M NaCl containing 1% Trition X-100 and 0.004% sodium metabisulfite. Plant tissue were mechanically homogenized using a POLYTRON™, grinding with mortar and pestle, or with a COMITROL™ in 1 volume of cold 50 mM Tris pH 8, 0.15 M NaCl. The buffer used with the COMITROL™ also contained 0.04% sodium metabisulfite. Following homogenization, the slurry of ground plant material was centrifuged at 5,000 g for 5 min at 4° C. and the crude extracts (supernatant) kept for analysis. The total protein content of clarified crude extracts was determined by the Bradford assay (Bio-Rad, Hercules, CA) using bovine serum albumin as the reference standard.

VLP Extraction by Cell Wall Digestion

Leaf tissue was collected from the *Nicotiana benthamiana* plants and cut into ~1 cm² pieces. The leaf pieces were soaked in 500 mM mannitol for 30 minutes at room temperature (RT). The mannitol solution was then removed and changed with the enzyme mix (mixture of cellulases from *Trichoderma viride* (Onozuka R-10; 3% v/v) and a mixture of pectinases from *Rhizopus* sp. (MACEROZYME™; 0.75% v/v; both from Yakult Pharmaceuticals) in protoplasting solution (500 mM mannitol, 10 mM $CaCl_2$ and 5 mM MES/KOH (pH 5.6)). The ratio used was 20 g of leaf pieces per 100 mL solution. This preparation was spread evenly into a shallow vessel (~11×18 cm) and incubated for 16 hours on a rotary shaker at 40 rpm and 26° C.

Alternately, VLP extraction may be performed as follows: plants were agroinfiltrated with AGL1/#685 as described in example 1. Leaf tissue was collected from the *N. benthamiana* plants at day 6 post-infiltration and cut into ~1 cm² pieces. Multifect Pectinase FE, Multifect CX CG and Multifect CX B (Genencor) were added to 1.0% each (v/v) in a 600 mM Mannitol, 75 mM Citrate, 0.04% sodium bisulfite pH 6.0 buffer using a ratio of 1:2.5 (w/v) fresh biomass; digestion buffer. The biomass was digested for 15 h at room temperature in a orbital shaker.

Following incubation, leaf debris was removed by filtration (nylon filter of 250 or 400 μm mesh). Protoplasts in suspension were collected by centrifugation at 200×g (15 min), followed by centrifugation of the supernatant at 5000×g (15 min) to further clarify the supernatant. Alternately, a single centrifugation step at 5000×g for 15 minutes may be employed. Seventy mL of the supernatant was then centrifuged at 70,000×g for 30 minutes. The resulting pellet was resuspended in 1.7 mL of PBS and analyzed immediately or frozen.

Protein Analysis

A hemagglutination assay for H5 was based on a method described by Nayak and Reichl (2004). Briefly, serial double dilutions of the test samples (100 μL) were made in V-bottomed 96-well microtiter plates containing 100 μL PBS, leaving 100 μL of diluted sample per well. One hundred microliters of a 0.25% turkey red blood cells suspension (Bio Link Inc., Syracuse, NY) were added to each well, and plates were incubated for 2 h at room temperature. The reciprocal of the highest dilution showing complete hemagglutination was recorded as hemagglutination activity. In parallel, a recombinant HA5 standard (A/Vietnam/1203/2004 H5N1) (Protein Science Corporation, Meriden, CT) was diluted in PBS and run as a control on each plate.

ELISA

HA5 standard was prepared with purified virus-like particles which were disrupted by treatment with 1% Triton X-100 followed by mechanical agitation in a Tissue Lyser™ (Qiagen) for 1 min. U-bottom 96-well microtiter plates were coated with 10 μg/mL of capture antibody (Immune Technology Corporation, #IT-003-0051) in 50 mM carbonate-bicarbonate coating buffer (pH 9.6) for 16-18 hours at 4° C. All washes were performed with 0.01 M PBS (phosphate-buffered saline), pH 7.4 containing 0.1% Tween-20. After incubation, plates were washed three times and blocked with 1% casein in PBS for 1 hour at 37° C. After the blocking step, plates were washed three times. The HA5 standard was diluted in a mock extract (prepared from leaf tissue infiltrated with AGL1/R472 alone) to generate a standard curve from 500 to 50 ng/mL. Samples to quantify were treated in 1% Triton X-100 prior to loading the microplate. Plates were further incubated for 1 hour at 37° C. After washing, sheep polyclonal antibody raised against HA5 (CBER/FDA) diluted 1:1000 was added and the plates were incubated for 1 hour at 37° C. After washing, horseradish peroxidase-conjugated rabbit anti-sheep antibody diluted 1:1000 was added and the plates were incubated for 1 hour at 37° C. After the final washes, the plates were incubated with SureBlue TMB peroxidase substrate (KPL) for 20 minutes at room temperature. Reaction was stopped by the addition of 1N HCl and $A_{450}$ values were measured using a Multiskan Ascent plate reader (Thermo Scientific).

Example 1

Enzymatic Extraction of Plant Tissue High Quantities of HA Having an Elevated Relative Activity The quantity and relative activity of HA obtained from the present enzymatic extraction method were compared with that of HA obtained from common mechanical extraction methods. *N. benthamiana* plants were infiltrated with AGL1/685 and the leaves were harvested after a five to six-day incubation period. Leaf homogenates were prepared as follows: Two grams of leaves were homogenized with a Polytron homogenizer; 4 g of leaves were ground with a mortar and a pestle; and 25 kg of leaves were homogenized with a COMITROL™ processor (Urschel Laboratories) in an extraction buffer (50 mM Tris, 150 mM NaCl pH 8.0, ratio of 1:1 w/v). Enzymatic extraction was carried as follow: Twenty grams of harvested leaves were subjected to digestion with Macroenzyme pectinases and Onozuka R-10 cellulases as described above. Following digestion, leaf debris were removed by filtration (nylon filter, 250 μm mesh). Protoplasts in suspension were removed by centrifugation at 200×g (15 min), and the supernatant further clarified by centrifugation at 5000×g (15 min).

The relative activity and quantity of HA in each of these plant extracts is shown in Table 3. The amount of HA released by enzymatic digestion of the cell wall is significantly superior when compared to the other techniques used.

TABLE 3

HA-VLP recovered form plant extract generated by different mechanical or enzymatic methods. For activity-based and ELISA comparisons, data was normalized according to the relative volume of liquid extract of fresh biomass. The protein obtained using Comitrol extraction was set at 100%, and the other methods compared to this value.

| Extraction method | Relative activity | Quantity* |
|---|---|---|
| Comitrol ™ extract | 100% | 100% |
| Polytron extract | 50% | 150% |
| Mortar extract | 100% | 220% |
| Digestion extract | 440% | 570% |

*Quantity was evaluated by ELISA analysis

Example 2

Enzymatic Digestion of Plant Tissue Releases HA Organized into VLPs

A combination of differential centrifugation and size exclusion chromatography (SEC) was used to demonstrate that the HA obtained by the enzymatic extraction method described herein were organized as VLPs. *N. benthamiana* plants were agroinfiltrated with AGL1/685 as described in Example 1. Leaves were collected from the plants 6 days post-infiltration and cut into ~1 $cm^2$ pieces then digested, coarse-filtered and centrifuged as described in Example 1.

The clarified samples were then centrifuged at 70,000×g to allow for segregation of VLPs. The centrifugation pellet, containing the VLPs, was gently resuspended in 1/50 volume of Phosphate buffered saline (PBS; 0.1M sodium phosphate, 0.15M NaCl pH 7.2) before being loaded on a SEC column.

SEC columns of 32 ml SEPHACRYL™ S-500 high resolution beads (S-500 HR: GE Healthcare, Uppsala, Sweden, Cat. No. 17-0613-10) were prepared with equilibration/elution buffer (50 mM Tris, 150 mM NaCl, pH8). SEC chromatography was performed with the loading of a 1.5 mL VLP sample onto the equilibrated column, and its elution with 45 mL of equilibration/elution buffer. The eluate was collected in fractions of 1.7 mL, and the protein content of each fraction was evaluated by mixing 10 μL of the eluate fraction with 200 μL of diluted Bio-Rad protein dye reagent (Bio-Rad, Hercules, CA). Each separation was preceded by a calibration with Blue Dextran 2000 (GE Healthcare Bio-Science Corp., Piscataway, NJ, USA). Comparison of the elution profiles of both Blue Dextran 2000 and host proteins was performed for each separation to ensure uniformity of the separations.

Protein Analysis of the SEC Eluted Fractions

Total protein content of clarified crude extracts was determined by the Bradford assay (Bio-Rad, Hercules, CA) using bovine serum albumin as the reference standard. Proteins present in SEC eluate fractions were precipitated with acetone (Bollag et al., 1996), resuspended in either 0.25 volume or 0.05 volume of denaturing sample loading buffer (0.1M Tris pH 6.8, 0.05% bromophenol blue, 12.5% glycerol, 4% SDS and 5% beta-mercaptoethanol) for SDS-PAGE analysis or immunoblot analysis, respectively. Separation by SDS-PAGE was performed under reducing conditions, and Coomassie Brilliant Blue R-250 was used for protein staining.

Hemagglutination assay for H5 was performed based on a method described by Nayak and Reichl (2004). Briefly, successive double dilutions of the test samples (100 µL) were made in V-bottomed 96-well microtiter plates containing 100 µL PBS, leaving 100 μL of diluted sample per well. One hundred microliters of a 0.25% turkey red blood cells suspension (Bio Link Inc., Syracuse, NY) were added to each well, and plates were incubated for 2 h at room temperature. The reciprocal of the highest dilution showing complete hemagglutination was recorded as hemagglutination activity. In parallel, a recombinant H5 standard (A/Vietnam/1203/2004 H5N1) (Protein Science Corporation, Meriden, CT) was diluted in PBS and run as a control on each plate.

FIG. 3A shows that the hemagglutination activity is concentrated in the fractions corresponding to the void volume of the column, confirming that the hemagglutination activity originates from a high molecular weight structural organization. SDS-PAGE analysis (FIG. 3B) revealed that those same void volume fractions (fractions 7-10) also present the highest HA content, with a band corresponding to the HA0 monomer being detectable at approximately 75 kDa.

Example 3

Enzymatic Digestion of Plant Tissue Releases HA-VLPs with Fewer Contaminants

*N. benthamiana* plants were agroinfiltrated with AGL1/685 as described in Example 1. Leaves were collected on day 6 post-infiltration, cut into ~1 $cm^2$ pieces, digested, coarse-filtered and centrifuged as described in Example 1.

The controlled enzymatic digestion of the leaves removed the cell walls, at least partially, thus allowing for the release of proteins and components presents in the space between the cell wall and the plasma membrane into the extraction medium. Since most intracellular proteins and components were still undamaged and contained within the mostly intact protoplasts, an initial centrifugation step allowed for their removal, thus providing a resulting solution comprising cell wall degrading enzymes, in addition of the extracellular plant proteins and components (apoplastic fraction), as shown in FIG. 4.

FIG. 4 shows a SDS-PAGE analysis of the resulting solution obtained following the controlled enzymatic digestion of leaves tissue as described previously, with lane 1 showing the enzyme mixture used and lane 2 showing the resulting solution following the enzymatic digestion. The protein content of a crude extract from Comitrol™ is provided on lane 3 for comparison. The biomass:buffer ratio for the extract presented in lane 2 was 1:5 (w/v) while it was 1:1 (w/v) for that in lane 3. Each of lanes 2 and 3 therefore contain proteins derived from an equivalent quantity of starting material. For approximately the same buffer:plant ratio, a mechanical plant extract contained a protein concentration of approximately 3.5-4 mg/ml, while the enzymatic plant extract obtained according to the present method presented a protein concentration of approximately 1 mg/ml.

The major contaminant present in lane 3 was found to be RubisCo (Ribulose-1,5-bisphosphate carboxylase oxygenase), which is made of two types of protein subunits: a large-chain (L, about 55 kDa) and a small-chain (S, about 13 kDa). A total of eight large-chain dimers and eight small-chains usually assemble with each other into a RubisCo 540 kDa larger complex. While this plant protein contaminant is found in large amount in plant extracts originating from mechanical extraction method (see arrow in FIG. 4), it is virtually absent in plant extracts obtained by the enzymatic digestion method described herein. Therefore, the present method allows for the elimination of this major plant protein contaminant, amongst others, at an early stage of the process.

Example 4

Enzymatic Digestion of Plant Tissue Releases HA-VLP in Conditions where it can be Directly Captured on a Cation Exchange Resin

*N. benthamiana* plants were agroinfiltrated with AGL1/685 as described in Example 1. Leaves were collected on day 6 post-infiltration, cut into ~1 $cm^2$ pieces and digested for 15 h at room temperature in an orbital shaker. The digestion buffer contained 1.0% (v/v) Multifect Pectinase FE, 1.0% (v/v) Multifect CX CG or and 1.0% (v/v) Multifect CX B (all from Genencor), each in a solution of 600 mM Mannitol, 75 mM Citrate, 0.04% sodium bisulfite pH 6.0 buffer using a biomass: digestion buffer ratio of 1:2.5 (w/v).

Following digestion, the apoplastic fraction was filtered through a 400 μm nylon filter to remove coarse undigested vegetal tissue (<5% of starting biomass). The filtered extract was then centrifuged at room temperature for 15 min at 5000×g to remove protoplasts and intracellular contaminants (proteins, DNA, membranes, vesicles, pigments, etc). Next, the supernatant was depth-filtered (for clarification) using a 0.65 μm glass fiber filter (Sartopore2/Sartorius Stedim) and a 0.45/0.2 μm filter, before being subjected to chromatography.

The clarified apoplastic fraction was loaded over a cation exchange column (Poros HS Applied Biosystems) equilibrated with an equilibration/elution buffer (50 mM $NaPO_4$, 100 mM NaCl, 0.005% Tween 80 pH 6.0). Once the UV was back to zero, the extract was step-eluted with the equilibration/elution buffer containing increasing concentrations of NaCl (500 mM). Where necessary, the chromatographic fractions were concentrated 10 times using Amicon™ devices equipped with 10 kDa MWCO. Protein analysis was performed as described in previous examples.

Under the above-mentioned conditions, most enzymes and plant proteins did not bind to the cation exchange resin whereas the HA-VLP did bind, thus providing a considerable enrichment in HA-VLPs in the eluted fraction (FIG. 6). In addition, as shown in FIG. 6, lane 4 and 5, the cellulases and pectinases did not bind to the cation exchange column at pH under 7. Consequently, recovery of HA-VLP, based on HA hemagglutination activity, was of 92% prior to loading on the cation exchange column, and of 66% in the eluted fraction. A purification factor of 194 was measured on the eluted fraction from the cation exchange resin.

Example 5

Addition of NaCl to the Digestion Buffer

*N. benthamiana* plants were agroinfiltrated with *Agrobacterium* AGL1 strains carrying a construct expressing a hemagglutinin of interest (H1/Cal WT, B/Flo, H5/Indo or H1/Cal X179A) as described in Example 1. Leaves were collected on day 6 post-infiltration, cut into ~1 cm² pieces and digested according to Example 4, except where noted below. Filtration, centrifugation and clarification were performed as described in Example 4.

NaCl was added to digestion buffer to evaluate its potential effect on the HA-VLP recovery rate. The suspected advantages were the potential prevention of non-specific association of HA with plant cells or with particle in suspension that are removed during clarification and potential effect on achievement and/or maintenance and/or improvement of colloidal stability of the HA-VLP.

Addition of 500 mM NaCl to the digestion buffer resulted in an increase of HA-VLP recovery yield per gram of biomass after removal of protoplasts and cellular debris by centrifugation. However, this increase was only noted with the for the H1/Cal WT and B/Flo strains, while the recovery yield for H5 was not significantly increased by this approach (Table 4).

TABLE 4

Effect of the addition of NaCl to the digestion step on the HA-VLP recovery yield (as measured by hemagglutination activity unit, dil: reciprocal of dilution)

| HA strain | Digestion conditions | Concentration in HA (dil/ml) | Yields (dil/g) | Yield increased (X-fold)[1] |
|---|---|---|---|---|
| H5 Indo/05 (#972) | Ø NaCl | 4608 | 12,430 | 1.2 |
| | 500 mM NaCl | 4608 | 14,921 | |
| H1 CA/07 WT (#604) | Ø NaCl | 384 | 1,206 | 2.1 |
| | 500 mM NaCl | 768 | 2,481 | |
| H1 CA/07 X-179A (#605) | Ø NaCl | 96 | 299 | 8.1 |
| | 500 mM NaCl | 768 | 2,419 | |
| B Flo/4 (475) | Ø NaCl | 16 | 52 | 7.5 |
| | 500 mM NaCl | 128 | 392 | |

[1]Yield (dil/g) with NaCl divided by Yield (dil/g) without NaCl

Addition of 500 mM NaCl during the digestion further resulted in an increase of the release of HA-VLP during digestion, which in turn resulted into increased recovery rate after clarification for both H1/Cal WT and H1/Cal X-179A strains (Table 5), but not for the H5/Indo strain.

TABLE 5

Effect of the addition of NaCl to the digestion step on the HA-VLP recovery yield (as measured by hemagglutination activity unit) after the clarification step.

| HA strain | Digestion conditions | Recovery after depth filtration[1] | Increase in recovery (X-fold) |
|---|---|---|---|
| H5/Indo (#972) | Ø NaCl | 100% | 1.0 |
| | 500 mM NaCl | 100% | |
| H1/Cal WT (#604) | Ø NaCl | 25% | 3.0 |
| | 500 mM NaCl | 75% | |
| H1/Cal X-179A (#605) | Ø NaCl | 50% | 2.0 |
| | 500 mM NaCl | 100% | |

[1]Recovery is expressed in percentage of hemagglutination activity obtained after depth filtration compared to the activity found in the centrifuged digested extract.

Figure 7A:
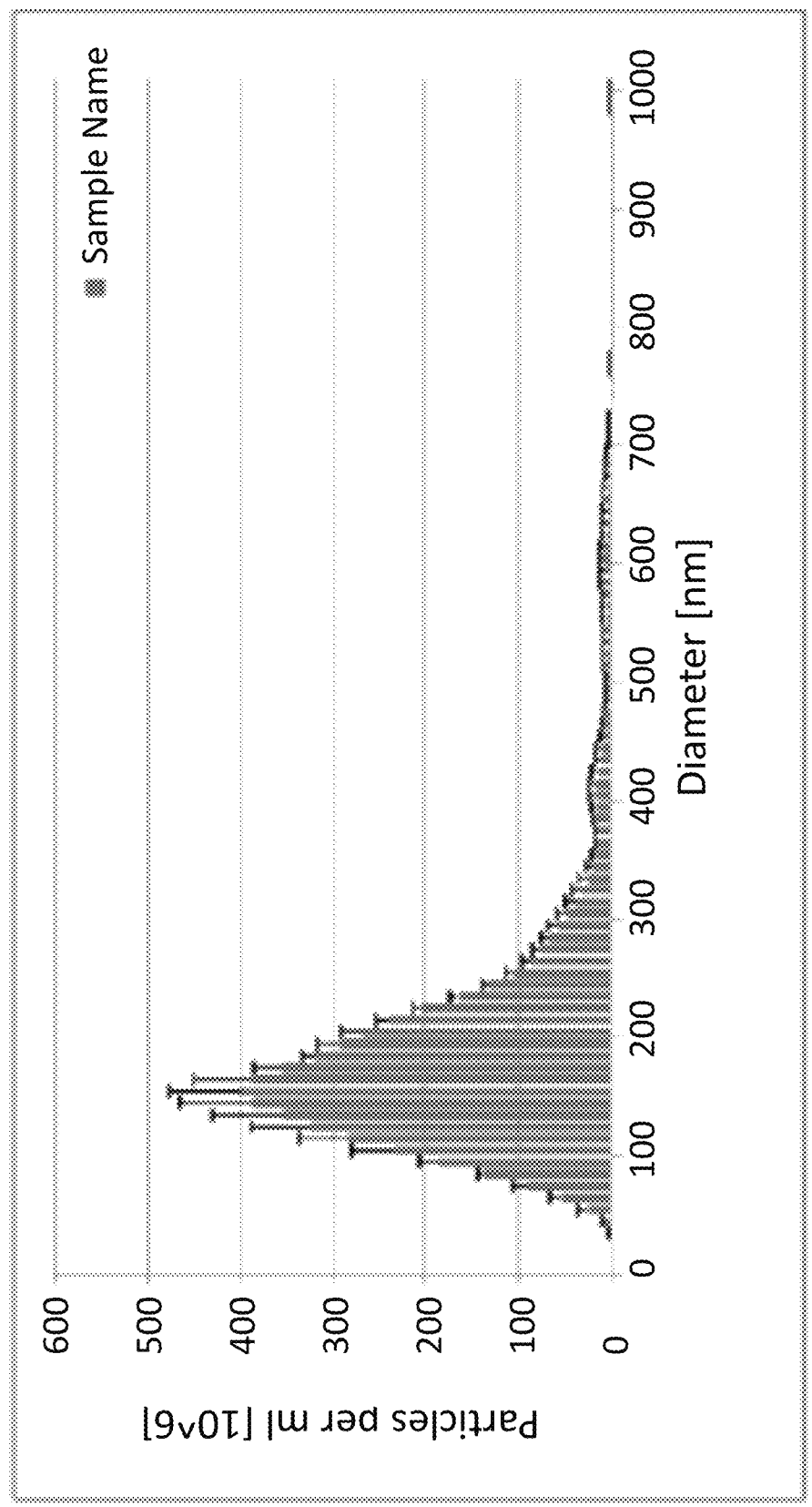
FIG. 7 shows the Nanoparticle Tracking analysis (NTA) profile of H5/Indo VLP (FIG. 7A) and H1/Cal VLP (FIG. 7B) after clarification without addition of NaCl to digestion buffer and of H1/Cal VLP (FIG. 7C) with this addition. NTA experiments were carried out with NanoSight LM20 (NanoSight, Amesbury, UK). The instrument is equipped with a blue laser (405 nm), a sample chamber and a Viton fluoroelastomer o-ring. Videos were recorded at room temperature and analysed using the NTA 2.0 software. The samples were recorded for 60 sec. The shutter and gain were manually chosen so that optimal particle resolution was obtained.
Figure 7B:
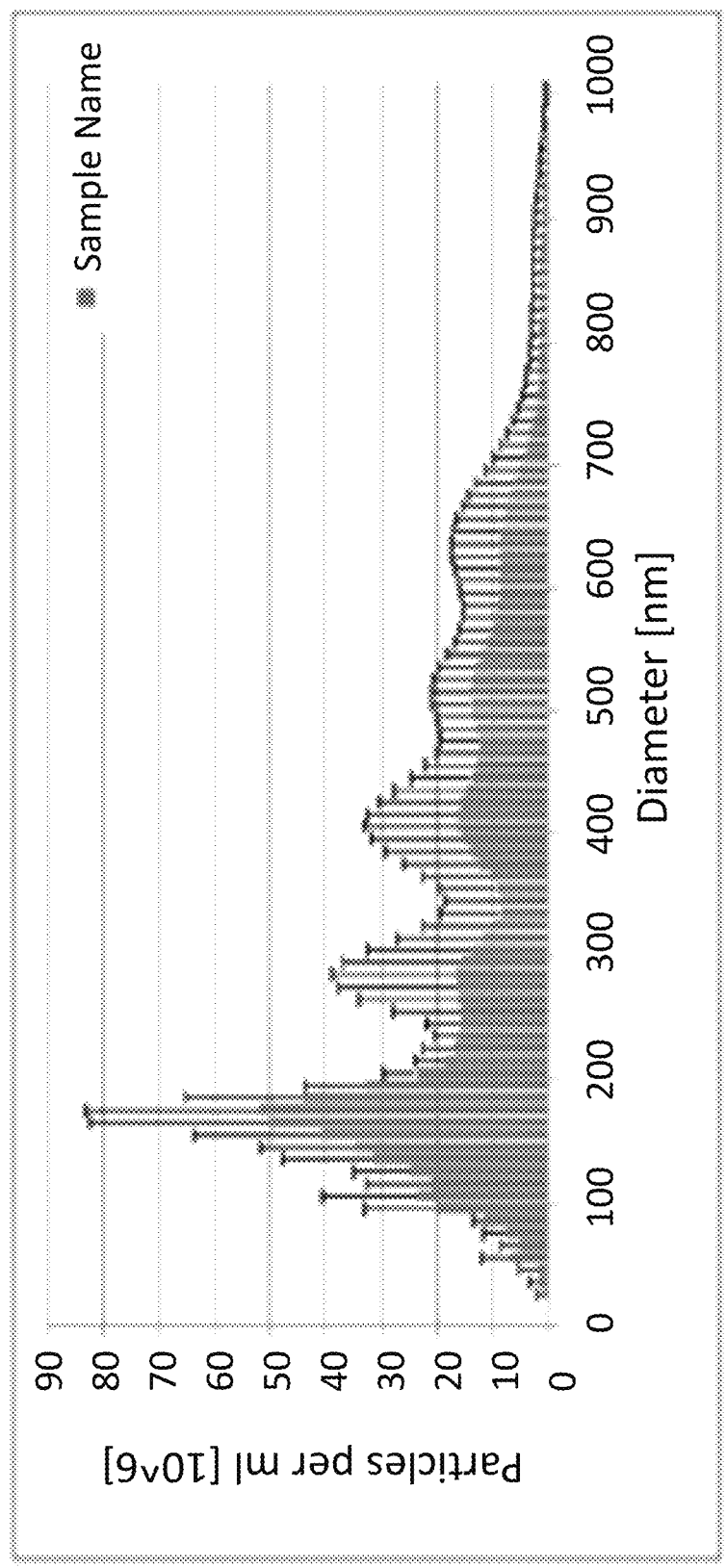
Figure 7C:
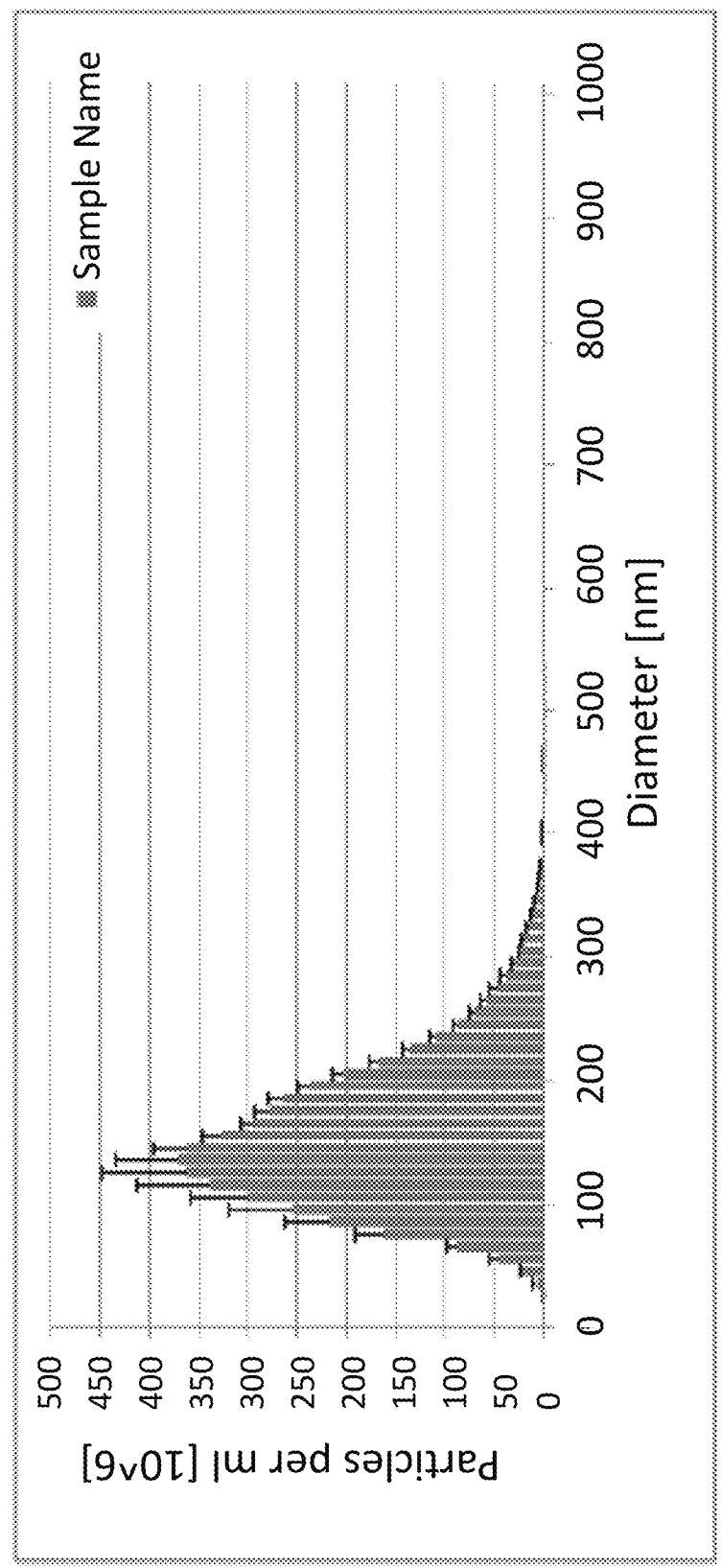
Figure 8:
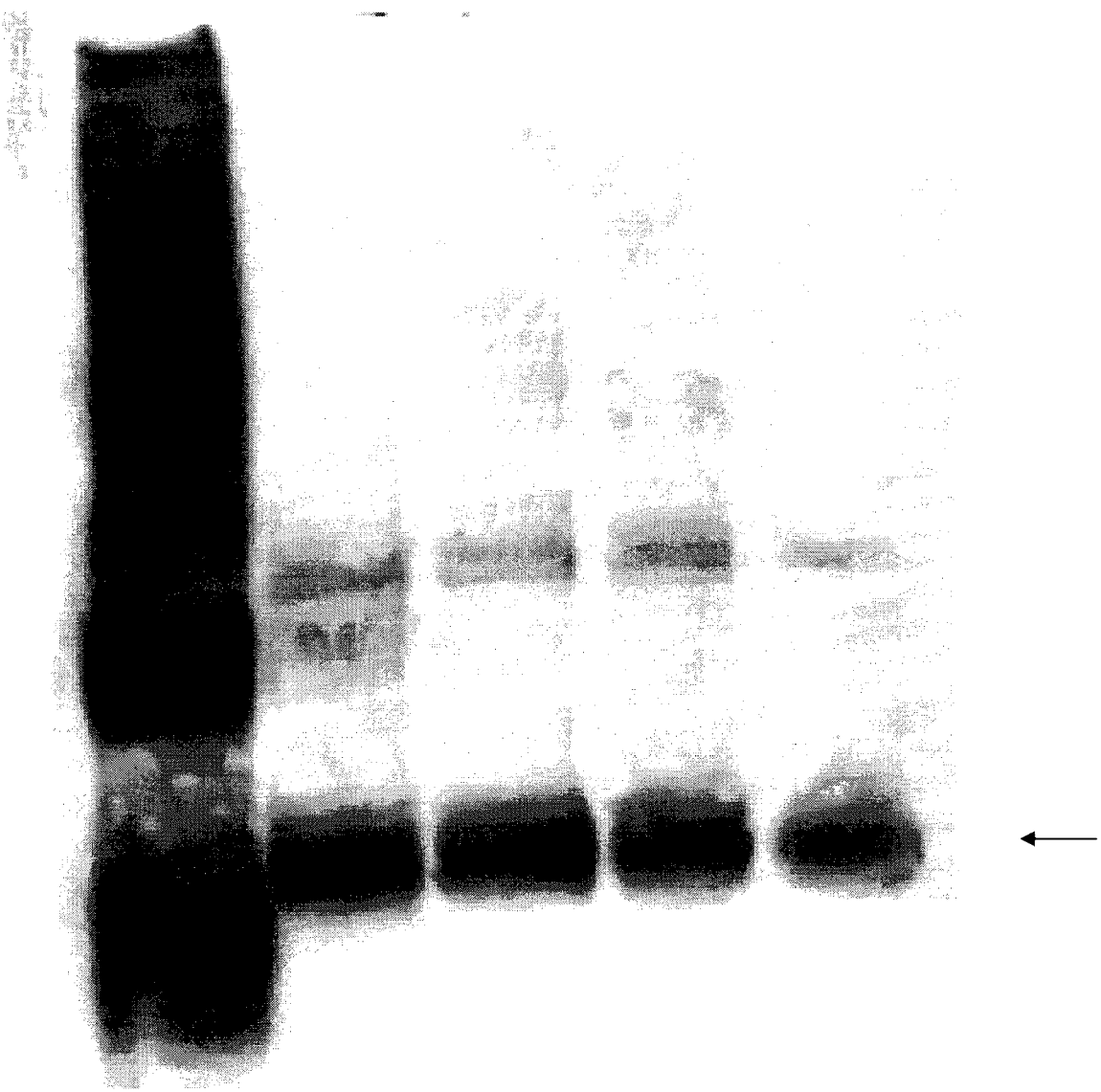
FIG. 8 shows a Western blot of extract of H3/Brisbane VLP generated by enzymatic digestion using different buffers. Lane 1) Pure recombinant HA standard (5 μg, from Immune Technology Corp. IT-003-0042p) Lane 2 to 5 contain 7 μl of centrifuged enzymatic extract performed in the following buffers: Lane 2) 600 mM Mannitol+125 mM citrate+75 mM NaPO$_4$+25 mM EDTA+0.04% bisulfite pH6.2, Lane 3) 600 mM Mannitol+125 mM citrate+75 mM NaPO$_4$+50 mM EDTA+0.04% bisulfite pH6.2, Lane 4) 200 mM Mannitol+125 mM citrate+75 mM NaPO$_4$+25 mM EDTA+0.03% bisulfite pH6.2, Lane 5) 200 mM Mannitol+ 125 mM citrate+75 mM NaPO$_4$+50 mM EDTA+0.03% bisulfite pH6.2. The arrow represents the immunodetection signal of HA0.

The association state of the HA-VLP, with and without the addition of NaCl during enzymatic digestion, was studied using Nanoparticle Tracking Analysis (NTA) for H5/Indo and H1/Cal WT (FIGS. 7A and 7B respectively). A monodisperse preparation of particles was observed for H5 when digestion was performed in absence of NaCl, while the H1/Cal preparation showed much larger array of particle species. The addition of NaCl to the digestion buffer reduced HA-VLP self-association for H1/Cal, as shown by the fairly monodisperse particle distribution found in FIG. 7C. The number of particles at 150 nm for H1/Cal WT-VLPs was enhanced (ca 5-fold) by the addition of 500 mM NaCl to the digestion buffer.

Example 6

Controlling Release of Pigments

*N. benthamiana* plants were agroinfiltrated with *Agrobacterium* AGL1 strains carrying a construct expressing a hemagglutinin of interest (H5/Indo) as described in Example 1. Leaves were collected on day 6 post-infiltration, cut into ~1 cm² pieces, and digested as described in Example 4, with addition of either 500 mM NaCl or 500 mM NaCl and 25 mM EDTA to the digestion buffer. Filtration, centrifugation and clarification were performed as described in Example 4.

Release of components having a green color during the enzymatic digestion step led to purified preparation of VLP having a greenish coloration. The composition of the cell wall digestion solution was therefore investigated and adjusted to obtain a VLP purified preparation having a reduced green coloration, and thus an increased purity. Without wishing to be bound by theory, since $Ca^{2+}$ plays a critical role in the retention of constituents of the cell wall's middle lamellae together, and given the fact that there is usually a high concentration of $Ca^{2+}$ in plant cell wall, the addition of $Ca^{2+}$-chelator EDTA could facilitate the enzymatic depolymerisation of the cell wall, thereby preserving intact intracellular organelles, such as chloroplasts, and preventing the release green-pigments components.

As shown in Table 6, the addition of 25 mM EDTA to the digestion buffer allowed for the reduction of the green coloration of the purified H5-VLP preparation, as evaluated by measuring the difference in absorption of the preparation ($OD_{677nm}-OD_{650nm}$). When the green constituents were released in high quantity, or not suitably removed, VLP preparation exhibited a $\Delta OD > 0.040$.

TABLE 6

Effect of the addition of 25 mM EDTA to the digestion buffer on green coloration of H5-VLP preparations.

| | $OD_{672nm}-OD_{650nm}$ |
|---|---|
| 0 mM NaCl, 0 mM EDTA | 0.071 ± 0.061 |
| 500 mM NaCl | 0.087 ± 0.060 |
| 500 mM NaCl + 25 mM EDTA | 0.010 ± 0.002 |

Example 7

Alternative Digestion Buffer Compositions

*N. benthamiana* plants were agroinfiltrated with *Agrobacterium* AGL1 strains carrying a construct expressing a hemagglutinin of interest (H5/Indo) as described in Example 1. Leaves were collected on day 6 post-infiltration, cut into ~1 cm² pieces and digested according to Example 4, with modification of digestion buffer to include 0%, 0.25%, 0.5%, 0.75% or 1% v/v Multifect Pectinase FE, Multifect CX-CG cellulase and Multifect CX B cellulase as noted in Tables 7-9. Filtration, centrifugation and clarification were as described in Example 4.

As shown in following tables 7 and 8, pectinase has been demonstrated to be non-essential in the digestion buffer. Similar levels of H5/Indo or H1/Cal WT VLP can be extracted with the present method either in the presence or absence of pectinase. Furthermore, it has been found that reducing the concentration of cellulase when compared to previous examples had no significant impact on the quality of extraction (Table 9).

TABLE 7

Release of H5/Indo VLP by digestion of *N. benthamiana* leaves. All conditions were tested in replicates. (Concentration in HA-VLP measured by hemagglutination activity, dil: reciprocal of dilution)

| Pectinase (% v/v) | Cellulase* (% v/v) | Concentration in H5 VLP (dil/ml) |
|---|---|---|
| 1 | 1 | 1152 |
| 0.5 | 1 | 6144 |
| 0 | 1 | 768 |
| 0 | 2 | 1536 |

*Multifect CX GC

TABLE 8

Release of H1/Cal WT VLP by digestion of *N. benthamiana* leaves. All conditions were tested in replicates. (Concentration in HA-VLP measured by hemagglutination activity, dil:reciprocal of dilution)

| Pectinase (% v/v) | Cellulase* (% v/v) | Concentration in H1 VLP (dil/ml) |
|---|---|---|
| 1 | 2 | 2304 |
| 0 | 2 | 3840 |

*1% each of Multifect CX GC and Multifect CX B

TABLE 9

Release of H1/Cal WT VLP by digestion of *N. benthamiana* leaves. All conditions were tested in replicates. (Concentration in HA-VLP measured by hemagglutination activity, dil:, reciprocal of dilution)

| Pectinase (% v/v) | Cellulase* (% v/v) | Concentration in H1 VLP (dil/ml) |
|---|---|---|
| 1.0 | 1 | 384 |
| 0.75 | 1 | 480 |
| 0.50 | 1 | 480 |
| 0.25 | 1 | 480 |

*Multifect CX GC

Example 8

Enzymatic Digestion in Conditions Near to Neutral pH

Controlling the pH during the digestion can be critical for the extraction of some VLPs. Taking into account that the depolymerisation of the cell wall occurring during the digestion step can release acid sugars that could acidify the solution (i.e. from pH 6 to 5) in the presence of appropriate buffers, and that some VLPs (such as those comprising H3/Bris and B/Flo HA) have already demonstrated a strong sensitivity to mildly acidic conditions, impact of such a potential acidification on the yield of VLP produced was investigated.

*N. benthamiana* plants were agroinfiltrated with *Agrobacterium* AGL1 strains carrying a construct expressing a hemagglutinin of interest (B/Flo, H5/Indo, H3/Bris) as described in Example 1. Leaves were collected on day 6 post-infiltration, cut into ~1 $cm^2$ pieces and digested according to Example 4, with modification of digestion conditions to include 500 mM NaCl; 25 or 50 mM EDTA; 0.03 or 0.04% sodium bisulfite; 0, 100, 200 or 600 mM mannitol, 75, 125 or 150 mM citrate; and/or 75 mM $NaPO_4$; with the pH of the digestion buffer adjusted as set out in Tables 10-14. Filtration, centrifugation and clarification were as described in Example 4.

Various digestion buffer compositions were tested to achieve a pH of approximately 5.5 by the end of the enzymatic digestion, including increased concentration of citrate (buffer effect between pH 3.0 and 5.4) and addition of sodium phosphate (buffer effect at pH above 6.0). Table 10 shows that VLPs from the B strain were extracted more efficiently when post-digestion pH was close to pH 6.0.

TABLE 10

Effect of the digestion buffer composition on the extraction yield of B/Flo VLPs.

| Buffer composition[1] | Concentration of B/Flo VLP (dil/ml) | Protein concentration (mg/ml) | pH post-digestion |
|---|---|---|---|
| 75 mM Citrate + 500 mM NaCl + 25 mM EDTA pH 6.0 | 1 | 0.92 | 5.0 |
| 75 mM Citrate pH 6.0 | 0 | 1.43 | 5.6 |
| 125 mM Citrate + 500 mM NaCl + 25 mM EDTA pH 6.0 | 1.5 | 1.07 | 5.4 |
| 150 mM Citrate + 500 mM NaCl + 25 mM EDTA pH 6.0 | 1.5 | 1.07 | 5.4 |
| 125 mM Citrate + 75 mM $NaPO_4$ + 500 mM NaCl + 25 mM EDTA pH 6.5 | 4 | 2.19 | 5.9 |

[1]All buffers contained 600 mM mannitol, sodium metabisulfite 0.04%

Next, the effect of initiating the digestion at a higher pH in order to reach final pH value close to pH 6.0 was tested. As shown in Table 11, the digestion of plant cell wall with such near-neutral conditions was possible, and did not impaired the extraction yield for H5/Indo VLPs.

TABLE 11

Effect of the initial pH of the digestion buffer on the extraction yield of H5/Indo VLPs.

| Initial pH of digestion solution[1] | Concentration of H5/Indo VLP (dil/ml) | Protein concentration (mg/ml) | pH post-digestion |
|---|---|---|---|
| 6.5 | 2304 | 2.79 | 6.08 |
| 6.4 | 1536 | 2.31 | 5.93 |
| 6.3 | 2304 | 2.40 | 5.81 |
| 6.2 | 2304 | 2.09 | 5.73 |
| 6.1 | 2304 | 1.72 | 5.61 |

[1]All digestion buffers contained 600 mM mannitol, sodium metabisulfite 0.04%, 125 mM Citrate + 75 mM $NaPO_4$ + 500 mM NaCl + 25 mM EDTA Other components of the digestion solution were also shown to be modifiable without negatively affecting the extraction yield of VLPs. Table 12 illustrates modifications that can be applied to the digestion solution in order to enhance the extraction yield of B/Flo VLPs, while obtaining a post-digestion pH of 5.4-5.7. Such modifications include increasing the concentration of citrate and adding a $PO_4$ buffer. It has been found that increasing the concentration of EDTA generally led to a more acidified extract and to lower VLP extraction yields.

TABLE 12

Effect of various digestion buffer components on the extraction yield of B/Flo VLPs.

| Buffer composition[1] | | | | | Concentration of B VLP (dil/ml) | Protein concentration (mg/ml) | pH post-digestion |
|---|---|---|---|---|---|---|---|
| Mannitol (mM) | Citrate (mM) | $PO_4$ (mM) | EDTA (mM) | pH | | | |
| 600 | 75 | 0 | 25 | 6.1 | 2 | 1.07 | 5.0 |
| 600 | 125 | 0 | 25 | 6.1 | 192 | 0.83 | 5.7 |
| 600 | 125 | 75 | 25 | 6.2 | 192 | 1.81 | 5.5 |
| 600 | 125 | 75 | 50 | 6.2 | 96 | 1.26 | 5.4 |
| 200 | 125 | 75 | 25 | 6.2 | 384 | 1.05 | 5.7 |
| 200 | 125 | 75 | 50 | 6.2 | 96 | 1.04 | 5.4 |
| 200 | 125 | 75 | 75 | 6.2 | 96 | 1.55 | 5.4 |

[1]All buffers contained 500 mM NaCl, and sodium metabisulfite 0.04%.

Buffer composition was further modified to improve the extraction yield of H3/Brisbane VLPs (Table 13)

TABLE 13

Effect of the concentrations of mannitol and sodium bisulfite in the digestion solution on the extraction yield of H3/Bris VLPs.

| Buffer composition | | | | Protein concentration (mg/ml) | pH post-digestion |
|---|---|---|---|---|---|
| Mannitol (mM) | Sodium bisulfite (%) | EDTA (mM) | pH | | |
| 600 | 0.04 | 25 | 6.2 | 1.87 | 5.7 |
| 600 | 0.04 | 50 | 6.2 | 1.62 | 5.6 |
| 200 | 0.03 | 25 | 6.2 | 1.89 | 5.7 |
| 200 | 0.03 | 50 | 6.2 | 1.24 | 5.6 |

[1]All buffers containing 125 mM Citrate, 75 mM $NaPO_4$, 500 mM NaCl,

As shown in Tables 12 and 13, mannitol concentration could be reduced to 200 mM without significantly affecting VLPs extraction yield. Further reduction of mannitol concentrations to 100 mM, and even the total omission of mannitol from the digestion solution, did not significantly affect the level of HA-VLP obtained (Table 14).

TABLE 14

Released of H5/Indo VLP from digestion of biomass performed in buffers with different concentration of mannitol.

| Mannitol concentration of the digestion solution[1] | Concentration of H5/Indo VLP (dil/ml) | Protein concentration (mg/ml) |
|---|---|---|
| Trial[2] 1: without mannitol | 2304 | 1.62 |
| Trial[2] 1: with 600 mM mannitol | 3072 | 1.73 |
| Trial[2] 2: with 100 mM mannitol | 4608 | 1.77 |
| Trial[2] 2: with 600 mM mannitol | 4608 | 2.0 |

[1]All buffers containing 75 mM Citrate pH 6.0 + sodium metabisulfite 0.04%.
[2]Two trials were were performed to compare the extraction yields of VLPs without mannitol (Trial 1) and with 100 mM mannitol (Trial 2) versus 600 mM mannitol.

Example 9

Suitability of Enzymatic Digestion to a Broad Variety of HA-VLPs

The enzymatic digestion method for plant biomass described herein has the potential to be applied to extracting of a broad variety of HA-VLPs. Adding to the extraction of HA-VLPs comprising H5/Indo, H1/Cal WT VLP, H3/Bris and B/Flo shown in previous examples, the method described herein was also shown to be suitable for the extraction of HA-VLPs from seasonal H1/Bris and H1/NC, as shown in Table 15.

TABLE 15

Release of seasonal H1/Bris and H1/NC VLP from digestion of agroinfiltrated *N. benthamiana* leaves. (concentration in HA measured by hemagglutination activity, dil: reciprocal of dilution)

| HA strain | Concentration in HA (dil/ml) |
|---|---|
| H1/Bri | 1536 |
| H1/NC | 384 |

Example 10

Antibody Preparation, Expression and Analysis

Assembly of C2B8 expression cassette (construct #595) C2B8 is a chimeric (mouse/human) monoclonal antibody directed against the B-cell-specific antigen CD20 expressed on non-Hodgkin's lymphomas (NHL). C2B8 mediates complement and antibody-dependent cell-mediated cytotoxicity and has direct antiproliferative effects against malignant B-cell lines in vitro (N Selenko et. al., Leukemia, Oct. 2001, 15 (10); 1619-1626).

A DNA fragment comprising 84 bp of the alfalfa plastocyanin promoter, the complete C2B8 light chain coding sequence and the complete alfalfa plastocyanin terminator was synthesized (LC fragment). The LC fragment was flanked by a DraIII restriction site (found in the plastocyanin promoter) and a EcoRI site downstream of the plastocyanin terminator. The sequence of LC fragment is presented in FIG. 9 (SEQ ID NO:15). The plasmid containing LC fragment was digested with DraIII and EcoRI and cloned into construct #660 (D'Aoust et al., Plant Biotechnol. J. 2008, 6: 930-940), previously digested with the same enzymes. The resulting plasmid was named construct number 590. A second DNA fragment was synthesized which comprises 84 bp of the alfalfa plastocyanin promoter, the complete C2B8 heavy chain coding sequence and the complete alfalfa plastocyanin terminator (HC fragment). The HC fragment was flanked by a DraIII restriction site (found in the plastocyanin promoter) and a EcoRI site downstream of the plastocyanin terminator. The sequence of HC fragment is presented in FIG. 16 (SEQ ID NO:16). The plasmid containing HC fragment was digested with DraIII and EcoRI and cloned into construct #660 (D'Aoust et al., Plant Biotechnol. J. 2008, 6: 930-940), previously digested with the same enzymes. The resulting plasmid was named construct number 592. The *A. tumefaciens* strain comprising 592, is termed "AGL1/592".

Figure 11A:
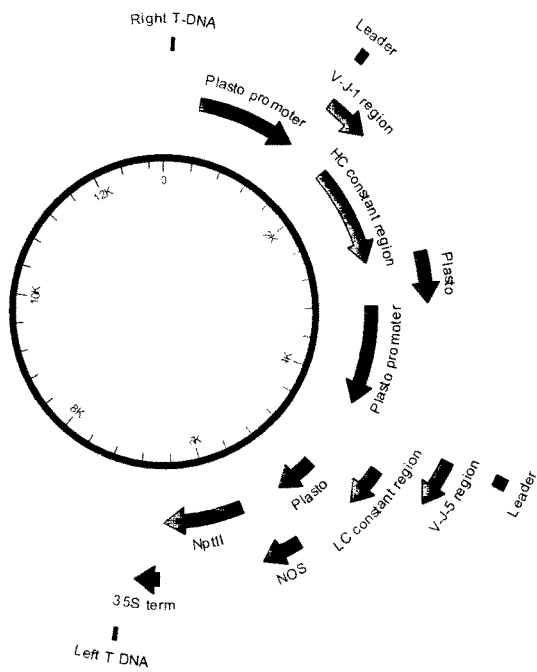
FIG. 11A and FIG. 11B show schematic representations of constructs #595 (FIG. 11A) and #R472 (FIG. 11B), respectively.
Figure 11B:
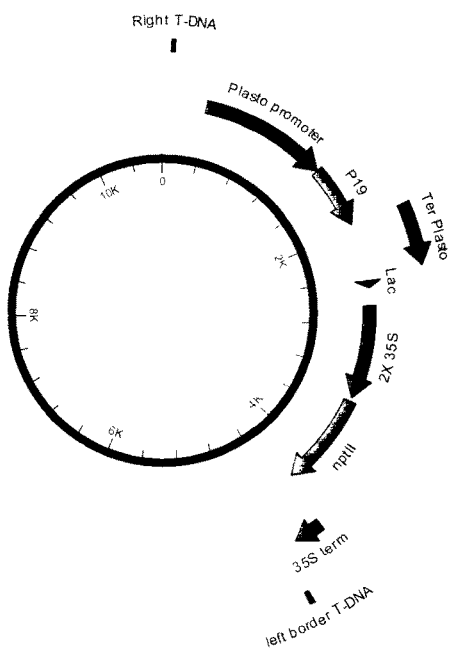

The plasmid comprising a dual expression cassette for C2B8 expression (construct #595) was assembled as follows. Construct number 592 was digested with EcoRI, treated with Klenow fragment to generate blunt-ends and digested with SbfI. The resulting fragments, comprising the complete cassette for the expression of C2B8 heavy chain flanked by a SbfI site and a blunt-end, was inserted into construct #590 previously digested with SbfI and SmaI. FIG. 11A presents a schematic representation of construct #595 used for the expression of C2B8 in plants.

Assembly of P19 Expression Cassette (Construct #R472)

The construct R472, encoding p19 protein is described above ("Suppressors of silencing"; see FIG. 11B)

Preparation of Plant Biomass, Bacterial Inoculum, Agroinfiltration, and Harvesting

*Nicotiana benthamiana* plants were grown as described above ("Preparation of plant biomass, inoculum, agroinfiltration, and harvesting") in a greenhouse under a 16/8 photoperiod and a temperature regime of 25° C. day/20° C. night. Three weeks after seeding, individual plantlets were picked out, transplanted in pots and left to grow in the greenhouse for three additional weeks under the same environmental conditions.

*Agrobacteria* bearing construct #595 or #R472 were grown in BBL Select APS LB broth medium supplemented with 10 mM 2-[N-morpholino]ethanesulfonic acid (MES), 50 μg/ml kanamycin and 25 μg/ml of carbenicillin pH5.6 until they reached an $OD_{600}>2.0$. *Agrobacterium* suspensions were centrifuged before use and resuspended in infiltration medium (10 mM $MgCl_2$ and 10 mM MES pH 5.6) and stored overnight at 4° C. On the day of infiltration, culture batches were diluted in 6.7 culture volumes and allowed to warm before use. Whole plants of *N. benthamiana* were placed upside down in the bacterial suspension in an air-tight stainless steel tank under a vacuum of 20-40 Torr for 1 min. Following infiltration, plants were returned to the greenhouse for a 5 day incubation period until harvest. Infiltrations were performed as co-infiltration with strains AGL1/595 and AGL1/R472 in a 1:1 ratio.

Leaf Sampling and Total Protein Extraction (Mechanical Extraction)

Following incubation, the aerial part of plants was harvested and used immediately. Total soluble proteins were extracted by homogenizing plant tissue in a domestic blender for 3 min. with 1.5 volumes of cold 20 mM $NaPO_4$ pH 6.0, 0.15 M NaCl and 2 mM sodium metabisulfite. Following homogenization, the slurry of ground plant material was filtered on Miracloth to remove large insoluble debris. The pH of the extract was adjusted to 4.8 by addition of 1M HCl and the non-soluble materials were removed by centrifugation 18 000 g for 15 min (4° C.). The supernatant was collected and the pH was adjusted to 8.0 with Tris base 2M. The insoluble materials were removed by centrifugation at 18 000 g for 15 min at 4° C. and the crude extract (supernatant) was collected. The total protein content of clarified crude extracts was determined by the Bradford assay (Bio-Rad, Hercules, CA) using bovine serum albumin as the reference standard.

Protein Extraction by Cell Wall Digestion

Leaf tissue was collected from the *Nicotiana benthamiana* plants and cut into ~1 $cm^2$ pieces. Leaf pieces were placed in 2.425 volumes of digestion solution (75 mM citrate pH 6.9, 600 mM mannitol, 1% Multifect Pectinase FE, 1% Multifect CXG, 1% Multifect B). This preparation was spread evenly into a shallow vessel and incubated for 16 hours on an orbital shaker at 120 rpm and 18° C. Following incubation, leaf debris were removed by filtration on a nylon filter (250 μm mesh). The extract was centrifuged at 5 000 g for 15 min. (22° C.) and the supernatant was collected and filtered on 0.65 μm glass fiber. The extract was adjusted to pH 6.0 with 0.5 M Tris base and filtered on PES membrane 0.45/0.22 μm.

Ammonium Sulfate Precipitation and Antibody Purification

Ammonium sulfate was slowly added to protein extracts to reach 45% saturation. The extract was kept on ice for 60 min and centrifuged at 18 000 g for 20 min. (4° C.). The supernatant was discarded and the pellet was kept frozen (−80° C.) until use.

The frozen protein pellet was thawed and resuspended in 1/10 volume (compared to the volume prior to precipitation) of protein resuspension solution (50 mM Tris pH 7.4, 150 mM NaCl). The protein solution was centrifuged at 12 000 g for 20 min. (4° C.) to remove non-solubilised materials. The protein solution was loaded onto MabSelect Sure resin (GE Healthcare, Baie d'Urfé, Canada). The column was washed with 10 CV of 50 mM Tris pH 7.4, 150 mM NaCl and the antibody was eluted with 6 CV of 100 mM sodium citrate pH 3.0. The elution volume was collected in 1 CV fractions in tubes containing 1/10 CV of 2 M Tris pH 7.4, NaCl 150 mM. Elution fractions were selected based on their protein content (measured by Bradford) and selected fractions were pooled and kept frozen (−80° C.) prior to analysis.

Protein Quantification and SDS-Page Analysis

Total protein content was determined by the Bradford assay (Bio-Rad, Hercules, CA) using either bovine serum albumin (for crude protein extracts) or commercial rituximab (Rituxan®, Hoffmann-La Roche, Mississauga, Canada) (for purified antibodies) as the reference standard. Coomassie-stained SDS-PAGE was performed as described by Laemmli (Nature 1970, 227: 680-685).

C2B8 Quantification by ELISA

Multiwell plates (Immulon 2HB, ThermoLab System, Franklin, MA) were coated with 2.0 μg/ml of monoclonal mouse anti-human IgG (Abcam, Ab9243) in 50 mM carbonate buffer (pH 9.6) at 4° C. for 16-18 h. Multiwell plates were then blocked through a 1 h incubation in 1% casein in phosphate-buffered saline (PBS) (Pierce Biotechnology, Rockford, Il) at 37° C. A standard curve was generated with dilutions of Rituximab (Rituxan®, Hoffmann-La Roche, Mississauga, Canada). When performing the immunoassays, all dilutions (control and samples) were performed in a plant extract obtained from plant tissue infiltrated and incubated with a mock inoculum (AGL1/R472 only) to eliminate matrix effect. Plates were incubated with protein samples and standard curve dilutions for 1 h at 37° C. After three washes with 0.1% Tween-20 in PBS (PBS-T), the plates were incubated with a peroxidase-conjugated dunkey anti-human IgG antibody (1/4000 dilution in blocking solution) (Jackson ImmunoResearch 709-035-149) for 1 h at 37° C.

The washes with PBS-T were repeated and the plates were incubated with a 3,3', 5,5'-Tetramethylbenzidine (TMB) Sure Blue peroxidase substrate (KPL, Gaithersburg, MD). The reaction was stopped by adding 1N HCl and the absorbance was read at 450 nm. Each sample was assayed in triplicate and the concentrations were interpolated in the linear portion of the standard curve.

N-Glycan Analysis

Samples comprising C2B8 (Rituxan™; 50 µg) were separated on 15% SDS/PAGE. Heavy and light chains were revealed with Coomassie blue and the protein band corresponding to the heavy chain was excised and cut into small fragments. Fragments were washed 3 times with 600 µL of a solution of 0.1M NH4HCO3/CH3CN (1/1) for 15 minutes each time and dried.

Reduction of disulfide bridges occurred by incubation of the gel fragments in 600 µL of a solution of 0.1M DTT in 0.1M NH4HCO3, at 56° C. for 45 minutes. Alkylation was carried out by adding 600 µL of a solution of iodoacetamide 55 mM in 0.1M NH4HCO3, at room temperature for 30 minutes. Supernatants were discarded and polyacrylamide fragments were washed once again in NH4HCO3 0.1M/CH3CN (1/1).

Proteins were then digested with 7.5 µg of trypsin (Promega) in 600 µL of 0.05M NH4HCO3, at 37° C. for 16 h. Two hundred µL of CH3CN were added and the supernatant was collected. Gel fragments were then washed with 200 µL of 0.1M NH4HCO3, then with 200 µL CH3CN again and finally with 200 µL formic acid 5%. All supernatants were pooled and lyophilized.

Glycopeptides were separated from peptides by chromatography on a Sep-Pack C18 cartridge. Glycopeptides were specifically eluted with 10% CH3CN in water and then analyzed by MALDI-TOF-MS on a Voyager DE-Pro MALDI-TOF instrument (Applied Biosystems, USA) equipped with a 337-nm nitrogen laser. Mass spectra were performed in the reflector delayed extraction mode using dihydrobenzoic acid (Sigma-Aldrich) as matrix.

Example 11

Comparison of C2B8 Antibody Extraction Yields

Enzymatic digestion was compared to mechanical extraction for the extraction of C2B8 antibody. *N. benthamiana* plants were agroinfiltrated with AGL1/595 and AGL1/R472. After 6 days of incubation, the leaves were harvested and proteins were extracted by enzymatic digestion or mechanical extraction. Extractions were performed twice and the resulting extracts were compared for volume, protein concentration and antibody (C2B8) content. Results are presented in Table 16.

From 700 g of biomass, the mechanical extraction generated a average of 1440 ml of protein extract whereas the digestion generated 2285 ml of protein extract. The percentage of C2B8 antibody was higher in the extract from digestion (average value of 479% of extracted proteins) than in the extract produced in the blender (average value of 3.49% of extracted protein). Together, the higher volume of extract and the higher concentration of antibody found in the extract result in an 37% higher extraction yield for the digestion (240.75 mg C2B8/kg fresh weight) than the mechanical extraction (175.95 mg C2B8/kg fresh weight).

Example 13

Comparison of Purified C2B8 Antibody (Protein Content)

Figure 12:
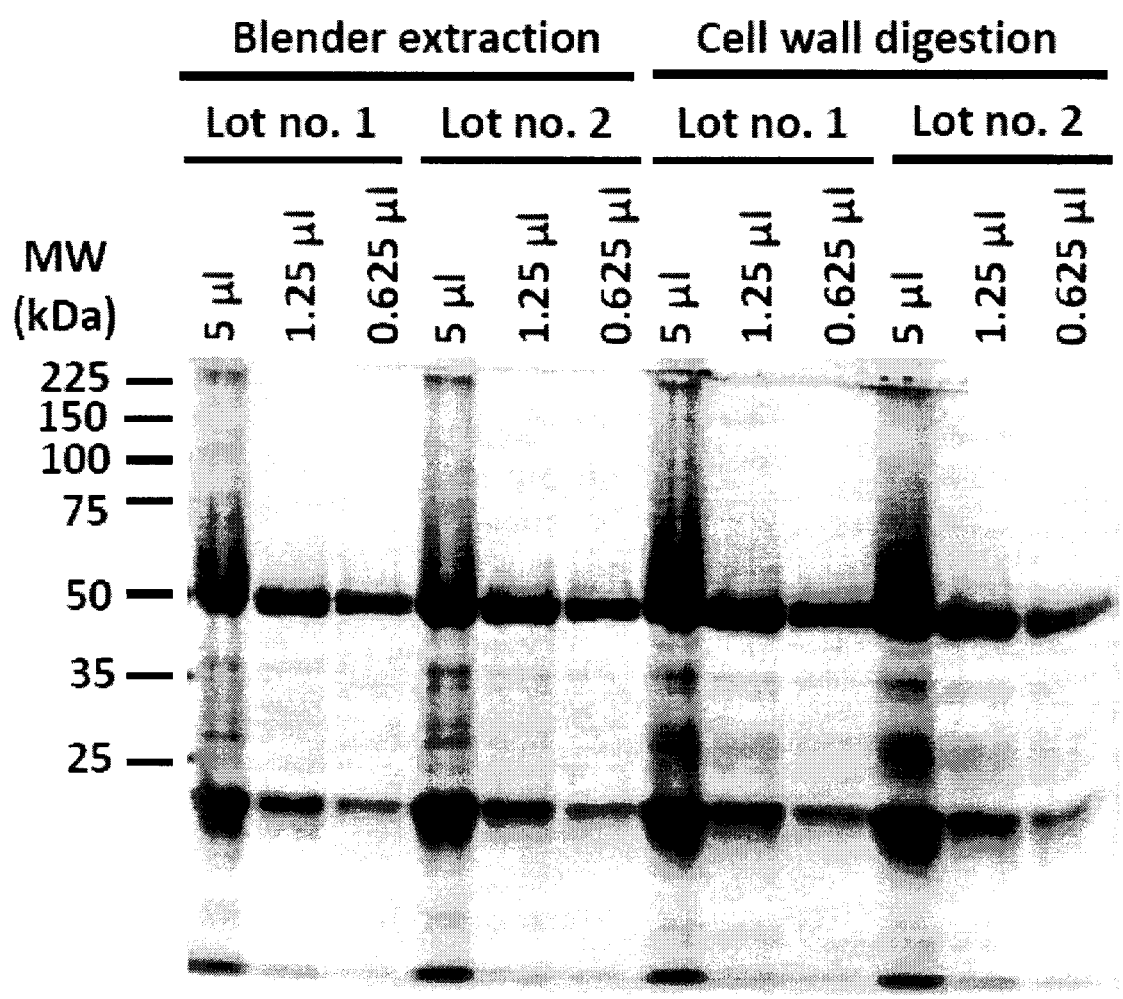
FIG. 12 SDS-PAGE comparison of antibodies purified from extracts produced by mechanical disruption (blender extraction) and enzymatic digestion of cell walls. For each extraction methods, two lots were processed and purified independently.

The C2B8 antibody was purified from the extracts by affinity chromatography on protein A as described in Example 10. The products purified from extracts obtained by mechanical extraction or digestion were compared on the basis of their protein content. The electrophoretic profile of the antibodies purified from each extraction lot is shown in FIG. 12. The results show that the profiles of the products purified from either blender extraction or cell wall digestion are similar.

Example 14

Comparison of Purified C2B8 Antibody (N-Glycosylation)

N-glycosylation of proteins consist in the addition of a complex glycan structure on the asparagine of secreted proteins bearing the N-X-S/T sequence, where N is the asparagine, X is any amino acid except a proline and S/T is a serine or a threonine. A precursor glycan is added early in the endoplasmic reticulum during the translation of the protein and, during their transit across the secretion pathway, N-glycans are subject to maturation. From a high-mannose type N-glycan in the endoplasmic reticulum (ER), N-glycan maturation in plants includes the addition and removal of glucose residues, the removal of mannoses in distal positions and the addition of N-acetylglucosamine, xylose, fucose and galactose residues. N-glycan maturation in plants is described by Gomord et al. in Post-translational modification of therapeutic proteins in plants (Curr. Opin. Plant Biol. 2004, 7: 171-181). Enzymes of the N-glycosylation pathway are positioned at precise locations in each compartment of the secretion pathway, namely the endoplasmic reticulum, the cis-Golgi, the medial Golgi and the trans-Golgi. Therefore, the N-glycosylation pattern of a protein

TABLE 16

Comparison of extraction yield for mechanical disruption (blender extraction) and enzymatic digestion of cell walls.

| Extraction lot | Biomass treated (g) | Crude extract volume (ml) | Protein concentration in the extract (mg/ml) | C2B8 concentration (% TSP) | C2B8 extraction yield (mg C2B8/kg FW) |
|---|---|---|---|---|---|
| Blender, lot no. 1 | 700 | 1400 | 2.42 | 3.33% | 161.4 |
| Blender, lot no. 2 | 700 | 1480 | 2.47 | 3.65% | 190.5 |
| Digestion, lot no. 1 | 700 | 2337 | 1.45 | 4.89% | 236.6 |
| Digestion, lot no. 2 | 700 | 2233 | 1.64 | 4.68% | 244.9 | will differ depending on its position at the moment of extraction. We have previously observed that a certain proportion of an antibody produced using agroinfiltration of *N. benthamiana* bore immature N-glycans of high mannose-type despite being targeted to the apoplast (Vézina et al., Plant Biotechnol. J. 2009 7: 442-455). A similar observation was reported elsewhere (Sriraman et al., Plant Biotechnol. J. 2004, 2, 279-287). In both cases, the presence of immature N-glycans on a certain proportion of antibodies was interpreted as the consequence of the presence of antibodies in early compartments of the secretion pathway at the moment of extraction.

The following study examined whether extraction of secreted glycoproteins by cell wall digestion was preferably extracting recombinant proteins bearing complex N-glycan. Antibodies and other glycoproteins secreted into the apoplast are expected to bear N-glycans having completed their maturation. Mature N-glycans most commonly bear terminal N-acetylglucosamine or galactose residues and are also named complex N-glycans. In contrast, immature N-glycans, mostly found on proteins en route in the secretory pathway, comprise terminal mannose residues. High mannose content of N-glycans on C2B8 (Rituxan™) has been associated with reduced half life in the blood stream (Kanda et al., Glycobiology 2006, 17: 104-118). In this context, an extraction method capable of favoring the extraction of apoplastic glycoproteins bearing complex N-glycans from plants would be desirable.

Figure 13B:
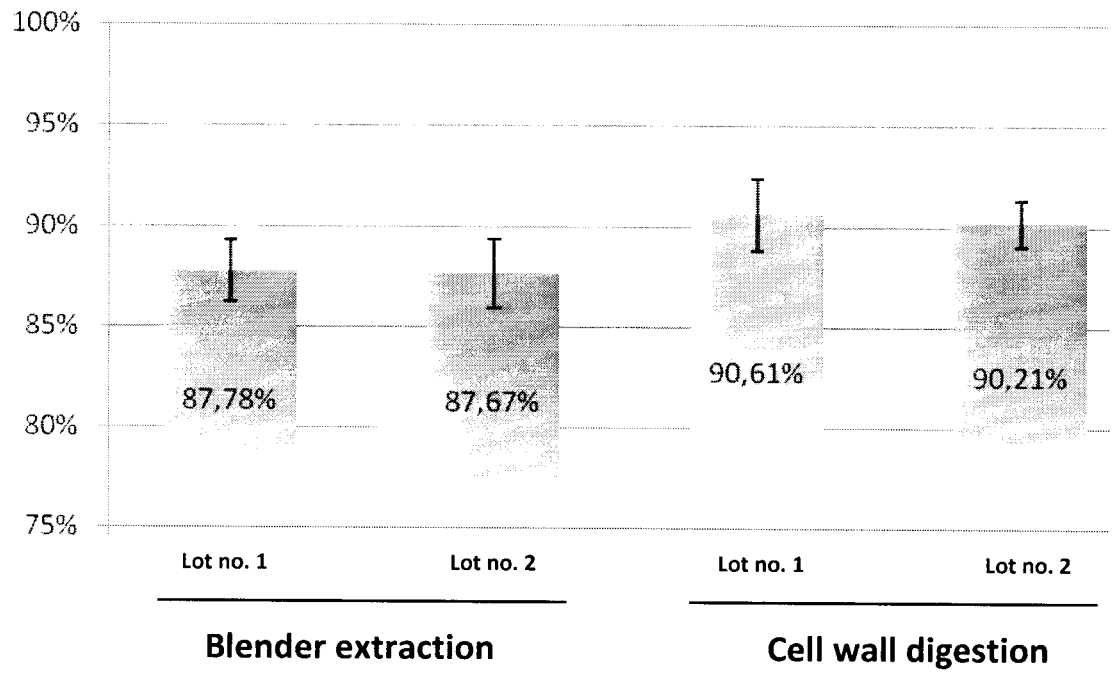
FIG. 13B shows a comparison of the proportion of complex N-glycans on C2B8 purified by mechanical disruption (blender extraction) and enzymatic digestion of cell walls.

A comparative analysis of N-glycosylation on purified C2B8 antibodies was carried out as described in Example 10. The results demonstrate that the antibodies purified from digested biomass bore a significantly lower proportion of oligomannosidic N-glycans (FIG. 13A) and, as a corollary, a significantly higher proportion of complex N-glycans (FIG. 13B).

Extraction by cell wall digestion could also be applied to plants co-expressing a glycoprotein and one or more enzymes for modifying N-glycosylation profile as described in WO 20008/151440 (Modifying glycoprotein production in plants; which is incorporated herein by reference) for favoring the recovery of glycoproteins bearing modified mature N-glycans. For example, mature N-glycans could be reduced, or exempt of xylose and fucose residues.

The method to modify N-glycosylation may involve co-expressing the protein of interest along with a nucleotide sequence encoding beta-1.4galactosyltransferase (GalT; provided as SEQ ID NO:14 of WO 20008/151440), for example, but not limited to mammalian GalT, or human GalT however GalT from another sources may also be used. The catalytic domain of GalT (for example nucleotides 370-1194 of SEQ ID NO:14 as described in WO 20008/151440), may also be fused to a CTS domain of N-acetyl-glucosaminyl transferase (GNT1; for example, comprising nucleotides 34-87 of SEQ ID NO:17 as provided in WO 20008/151440), to produce a GNT1-GalT hybrid enzyme. The hybrid enzyme may be co-expressed with a sequence encoding the suprastructure protein of interest. Additionally, the sequence encoding the suprastructure of interest may be co-expressed with a nucleotide sequence encoding N-acetyl-glucosaminyltrasnferase III (GnT-III; SEQ ID NO:16 as described in WO 20008/151440). A mammalian GnT-III or human GnT-III, GnT-III from other sources may also be used. Additionally, a GNT1-GnT-III hybrid enzyme (SEQ ID NO:26; as described in WO 20008/151440), comprising the CTS of GNT1 fused to GnT-III may also be used.

All citations are herein incorporated by reference, as if each individual publication was specifically and individually indicated to be incorporated by reference herein and as though it were fully set forth herein. Citation of references herein is not to be construed nor considered as an admission that such references are prior art to the present invention.

One or more currently preferred embodiments of the invention have been described by way of example. The invention includes all embodiments, modifications and variations substantially as hereinbefore described and with reference to the examples and figures. It will be apparent to persons skilled in the art that a number of variations and modifications can be made without departing from the scope of the invention as defined in the claims. Examples of such modifications include the substitution of known equivalents for any aspect of the invention in order to achieve the same result in substantially the same way.

What is claimed is:

1. A method of preparing plant derived antibodies, the method comprising:
   a. obtaining a *Nicotiana benthamiana* plant or plant matter comprising apoplast-localized antibodies, wherein a nucleic acid comprising a nucleotide sequence encoding the antibodies has been introduced into the *Nicotiana benthamiana* plant in a transient manner, and wherein the *Nicotiana benthamiana* plant matter consists of plant leaves, leaf pieces, shredded leaves, or a combination thereof;
   b. producing a digested fraction, wherein the digested fraction comprises an apoplast fraction, a protoplast fraction and plant debris, by extraction from the plant or plant matter, wherein the extraction consists of an enzymatic extraction, with a cell wall degrading enzyme mixture, wherein the cell wall degrading enzyme mixture comprises one or more than one cellulase and one or more than one pectinase, wherein a concentration of the one or more than one pectinase is about 1% (v/v) and a concentration of the one or more than one cellulase is about 1% (v/v), about 600 mM mannitol, about 75 mM citrate, and a buffer or buffer system which maintains a pH of about 6.9, at room temperature—with agitation for about 16 hours, wherein substantially all of the protoplasts in the protoplast fraction are disrupted protoplasts; and
   c. separating the plant debris from the digested fraction using filtration with a mesh size of more than 250 μm, centrifuging at about 5,000 g for about 15 minutes at room temperature to remove organelles, and to produce a supernatant, and recovering the plant-derived antibodies from the supernatant.

2. The method of claim 1 wherein in the step of obtaining (step a), the plant is grown and the plant or plant matter is harvested.

3. The method of claim 1 wherein the nucleic acid encodes a monoclonal antibody, a polyclonal antibody, a single chain monoclonal antibody, a chimeric antibody, a chimeric monoclonal antibody or a chimeric single chain monoclonal antibody.

4. The method of claim 1 further comprising a step of d) purifying the plant derived proteins, or protein suprastructures, from the supernatant.

5. The method of claim 4, wherein the step of purifying comprises filtering the supernatant using depth filtration to produce a clarified extract, followed by chromatography of the clarified extract using size exclusion chromatography, cation exchange resin or affinity chromatography, or a combination thereof.

6. A method of preparing plant derived antibodies, the method comprising:
   a. obtaining a *Nicotiana benthamiana* plant or plant matter comprising apoplast-localized antibodies, wherein a nucleic acid comprising a nucleotide sequence encoding the antibodies has been introduced into the *Nicotiana benthamiana* plant in a transient manner, and wherein the *Nicotiana benthamiana* plant matter consists of plant leaves, leaf pieces, shredded leaves or a combination thereof;
   b. digesting the plant matter using a cell wall degrading enzyme mixture comprising one or more than one cellulase and one or more than one pectinase, wherein a concentration of the one or more than one pectinase is about 1% (v/v) and a concentration of the one or more than one cellulase is about 1% (v/v), about 600 mM mannitol, about 75 mM citrate, and a buffer or buffer system which maintains a pH of about 6.9, at room temperature, with agitation for about 16 hours, to produce a digested fraction, the digested fraction comprising an apoplast fraction, a protoplast fraction and plant debris, wherein substantially all of the protoplasts in the protoplast fraction are disrupted protoplasts; and
   c. separating the plant debris from the digested fraction using filtration with a mesh size of more than 250 μm, centrifuging at about 5,000 g for about 15 minutes at room temperature to remove organelles, and to produce a supernatant, and recovering the plant-derived antibodies from the supernatant.

7. The method of claim 6, wherein the nucleic acid encodes a monoclonal antibody, a polyclonal antibody, a single chain monoclonal antibody, a chimeric antibody, a chimeric monoclonal antibody or a chimeric single chain monoclonal antibody.

8. The method of claim 6, further comprising the step of d) purifying the plant derived proteins or protein suprastructures, from the supernatant.

9. The method of claim 8, wherein the step of purifying comprises depth filtration of the supernatant to produce a clarified extract, followed by chromatography of the clarified extract using a cation exchange resin, a size exclusion resin, an affinity resin, or a combination thereof.

10. The method of claim 1, wherein the cell wall degrading enzyme mixture further comprises about 5 mM to about 200 mM EDTA or EGTA.

11. The method of claim 6, wherein the cell wall degrading enzyme mixture further comprises about 5 mM to about 200 mM EDTA or EGTA.

* * * * *